United States Patent
Birks et al.

(10) Patent No.: US 9,663,566 B2
(45) Date of Patent: May 30, 2017

(54) SOLUBLE HYBRID FCγ RECEPTORS AND RELATED METHODS

(71) Applicant: ZymoGenetics, Inc., Princeton, NJ (US)

(72) Inventors: Carl W Birks, Seattle, WA (US); Brian A Fox, Seattle, WA (US); Mark W Rixon, Seattle, WA (US); Jeff L Ellsworth, Lexington, MA (US)

(73) Assignee: ZymoGenetics, Inc., Seattle, WA (US)

( * ) Notice: Subject to any disclaimer, the term of this patent is extended or adjusted under 35 U.S.C. 154(b) by 440 days.

(21) Appl. No.: 14/109,165

(22) Filed: Dec. 17, 2013

(65) Prior Publication Data
US 2014/0107034 A1    Apr. 17, 2014

Related U.S. Application Data

(62) Division of application No. 12/999,564, filed as application No. PCT/US2009/049013 on Jun. 29, 2009, now Pat. No. 8,658,766.

(60) Provisional application No. 61/076,392, filed on Jun. 27, 2008, provisional application No. 61/163,526, filed on Mar. 26, 2009.

(51) Int. Cl.
| | | |
|---|---|---|
| *C07K 14/705* | (2006.01) | |
| *C07K 14/735* | (2006.01) | |
| *C07K 1/00* | (2006.01) | |
| *A61K 39/00* | (2006.01) | |
| *A61K 38/00* | (2006.01) | |

(52) U.S. Cl.
CPC .. *C07K 14/70503* (2013.01); *C07K 14/70535* (2013.01); *A61K 38/00* (2013.01)

(58) Field of Classification Search
None
See application file for complete search history.

(56) References Cited

U.S. PATENT DOCUMENTS 8,658,766 B2 * 2/2014 Birks .................... 424/184.1
2008/0219978 A1 9/2008 Ellsworth

FOREIGN PATENT DOCUMENTS

WO   WO 91/06570   5/1991
WO   WO 2008/091682   7/2008

OTHER PUBLICATIONS

Allen, Janet M., et al., "Isolation and Expression of Functional High-Affinity Fc Receptor Complementary DNAs", Science, 1989, vol. 243, pp. 378-381.
Davis, W., et al., "Two distinct regions of FcγRI initiate separate signalling pathways involved in endocytosis and phagocytosis", The EMBO Journal, 1995, vol. 14, No. 3, pp. 432-441.
Harrison, Patrick T., et al., "High affinity IgG binding by FcγRI (CD64) is modulated by two distinct IgSF domains and the transmembrane domain of the receptor", Protein Engineering, 1998, vol. 11, No. 3, pp. 225-232.
Sondermann, et al., "Characterization and Crystallization of Soluble Human Fcγ Receptor II (CD32) Isoforms Produced in Insect Cells", Biochemistry 1999, vol. 38, pp. 8469-8477.
Teillaud, et al., "Soluble CD16 Binds Peripheral Blood Mononuclear Cells and Inhibits Pokeweed-Mitogen-Induced Responses", Blood, Nov. 15, 1993, vol. 82, pp. 3081-3090.
Ellsworth, J.L. et al., "Targeting Immune Complex-Mediated Hypersensitivity with Recombinant Soluble Human FcγRIA (CD64A)", The Journal of Immunology, vol. 180, pp. 580-589 (2008).
Hulett, M.D. et al., "The second and third extracellular domains of FcγRI (CD64) confer the unique high affinity binding of IgG2a", Molecular Immunology, vol. 35, pp. 989-996 (1998).
Ierino, F.L. et al., "Recombinant Soluble Human FcγRII: Production, Characterization, and Inhibition of the Arthus Reaction", J. Exp. Med., vol. 178, pp. 1617-1628 (1993).
Raghavan M. et al., "Fc Receptors and their Interactions with Immunoglobulins", Annu. Rev. Cell Dev. Biol., vol. 12, pp. 181-220 (1996).
International Search Report in International Application No. PCT/US09/49013, Jan. 5, 2011 (9 pages).
Woof et a I. Nature Review Immunology 2004, 4:1-11.
Skolnick et a I. Trends in Biotech. 2000; 18(1):34-39.

* cited by examiner

*Primary Examiner* — Chun Dahle
(74) *Attorney, Agent, or Firm* — Nickki L. Parlet

(57) ABSTRACT

Disclosed are soluble hybrid Fcγ receptor (FcγR) polypeptide compositions and related methods of using such polypeptides to treat IgG-mediated and immune complex-mediated inflammation. Also disclosed are related compositions and methods for producing the soluble hybrid FcγR polypeptides.

3 Claims, 19 Drawing Sheets

Figure 6A

CTTGGAGACAACATGTGGTTCTTGACAACTCTGCTCCTTTGGGTTCCAGTTGATGGGCAAGTGGACAC
CACAAAGGCAGTGATCACTTTGCAGCCTCCATGGGTCAGCGTGTTCCAAGAGGAAACCGTAACCTTGC
ATTGTGAGGTGCTCCATCTGCCTGGGAGCAGCTCTACACAGTGGTTTCTCAATGGCACAGCCACTCAG
ACCTCGACCCCCAGCTACAGAATCACCTCTGCCAGTGTCAATGACAGTGGTGAATACAGGTGCCAGAG
AGGTCTCTCAGGGCGAAGTGACCCCATACAGCTGGAAATCCACAGAGGCTGGCTACTACTGCAGGTCT
CCAGCAGAGTCTTCACGGAAGGAGAACCTCTGGCCTTGAGGTGTCATGCGTGGAAGGATAAGCTGGTG
TACAATGTGCTTTACTATCGAAATGGCAAAGCCTTTAAGTTTTTCCACTGGAATTCTAACCTCACCAT
TCTGAAAACCAACATAAGTCACAATGGCACCTACCATTGCTCAGGCATGGGAAAGCATCGCTACACAT
CAGCAGGAATATCTGTCACTGTGAAAGAGCTATTTCCAGCTCCAGTGCTGAATGCATCTGTGACATCC
CCACTCCTGGAGGGGAATCTGGTCACCCTGAGCTGTGAAACAAAGTTGCTCTTGCAGAGGCCTGGTTT
GCAGCTTTACTTCTCCTTCTACATGGGCAGCAAGACCCTGCGAGGCAGGAACACATCCTCTGAATACC
AAATACTAACTGCTAGAAGAGAAGACTCTGGGTTATACTGGTGCGAGGCTGCCACAGAGGATGGAAAT
GTCCTTAAGCGCAGCCCTGAGTTGGAGCTTCAAGTGCTTGGCCTCCAGTTACCAACTCCTGTCTGGTT
TCATGTCCTTTTCTATCTGGCAGTGGGAATAATGTTTTTAGTGAACACTGTTCTCTGGGTGACAATAC
GTAAAGAACTGAAAAGAAAGAAAAAGTGGGATTTAGAAATCTCTTTGGATTCTGGTCATGAGAGAAG
GTAATTTCCAGCCTTCAAGAAGACAGACATTTAGAAGAAGAGCTGAAATGTCAGGAACAAAAAGAAGA
ACAGCTGCAGGAAGGGGTGCACCGGAAGGAGCCCCAGGGGGCCACGTAGCAGCGGCTCAGTGGGTGGC
CATCGATCTGGACCGTCCCCTGCCCACTTGCTCCCGTGAGCACTGCGTACAAACATCCAAAAGTTCA
ACAACACCAGAACTGTGTGTCTCATGGTATGTAACTCTTAAAGCAAATAAATGAACTGACTTCAACTG
GGATACATTTGGAAATGTGGTCATCAAAGATGACTTGAAATGAGGCCTACTCTAAAGAATTCTTGAAA
AACTTACAAGTCAAGCCTAGCCTGATAATCCTATTACATAGTTTGAAAAATAGTATTTTATTTCTCAG
AACAAGGTAAAAAGGTGAGTGGGTGCATATGTACAGAAGATTAAGACAGAGAAACAGACAGAAAGAGA
CACACACACAGCCAGGAGTGGGTAGATTTCAGGGAGACAAGAGGGAATAGTATAGACAATAAGGAAGG
AAATAGTACTTACAAATGACTCCTAAGGGACTGTGAGACTGAGAGGGCTCACGCCTCTGTGTTCAGGA
TACTTAGTTCATGGCTTTTCTCTTTGACTTTACTAAAAGAGAATGTCTCCATACGCGTTCTAGGCATA
CAAGGGGGTAACTCATGATGAGAAATGGATGTGTTATTCTTGCCCTCTCTTTTGAGGCTCTCTCATAA
CCCCTCTATTTCTAGAGACAACAAAAATGCTGCCAGTCCTAGGCCCCTGCCCTGTAGGAAGGCAGAAT
GTAACTGTTCTGTTTGTTTAACGATTAAGTCCAAATCTCCAAGTGCGGCACTGCAAAGAGACGCTTCA
AGTGGGGAGAAGCGGCGATACCATAGAGTCCAGATCTTGCCTCCAGAGATTTGCTTTACCTTCCTGAT
TTTCTGGTTACTAATTAGCTTCAGGATACGCTGCTCTCATACTTGGGCTGTAGTTTGGAGACAAAATA
TTTTCCTGCCACTGTGTAACATAGCTGAGGTAAAAACTGAACTATGTAAATGACTCTACTAAAAGTTT
AGGGAAAAAAAACAGGAGGAGTATGACACA

Figure 6B

MWFLTTLLLWVPVDGQVDTTKAVITLQPPWVSVFQEETVTLHCEVLHLPGSSSTQWFLNGTATQTSTP
SYRITSASVNDSGEYRCQRGLSGRSDPIQLEIHRGWLLLQVSSRVFTEGEPLALRCHAWKDKLVYNVL
YYRNGKAFKFFHWNSNLTILKTNISHNGTYHCSGMGKHRYTSAGISVTVKELFPAPVLNASVTSPLLE
GNLVTLSCETKLLLQRPGLQLYFSFYMGSKTLRGRNTSSEYQILTARREDSGLYWCEAATEDGNVLKR
SPELELQVLGLQLPTPVWFHVLFYLAVGIMFLVNTVLWVTIRKELKRKKKWDLEISLDSGHEKKVISS
LQEDRHLEEELKCQEQKEEQLQEGVHRKEPQGAT

Figure 6C

QVDTTKAVITLQPPWVSVFQEETVTLHCEVLHLPGSSSTQWFLNGTATQTSTPSYRITSASVNDSGEY
RCQRGLSGRSDPIQLEIHRGWLLLQVSSRVFTEGEPLALRCHAWKDKLVYNVLYYRNGKAFKFFHWNS
NLTILKTNISHNGTYHCSGMGKHRYTSAGISVTVKELFPAPVLNASVTSPLLEGNLVTLSCETKLLLQ
RPGLQLYFSFYMGSKTLRGRNTSSEYQILTARREDSGLYWCEAATEDGNVLKRSPELELQVLGLQLPT
PVWFH

Figure 6D

FCG1_HUMAN     Swiss Prot entry     (same as pFCGR1A - CloneTrack Entry)
FCG1_a is the "a isoform"                [Matches CloneTrack 101536]

```
                          |  16  |                                          50
FCG1_a        MWFLTTLLLW VPVDGQVDTT KAVITLQPPW VSVFQEETVT LHCEVLHLPG
              |          |

100
FCG1_a        SSSTQWFLNG TATQTSTPSY RITSASVNDS GEYRCQRGLS GRSDPIQLEI
                                              Ig 1

|                                                       150
FCG1_a        HRGWLLLQVS SRVFTEGEPL ALRCHAWKDK LVYNVLYYRN GKAFKFFHWN
              |                          Ig 2
FCG1_b1       ..........  ....M..... .......... .......... ..........
FCG1_c        ....P.....  .......... .......... .......... ..........

200
FCG1_a        SNLTILKTNI SHNGTYHCSG MGKHRYTSAG IS-VTVKELFP APVLNASVTS

FCG1_b1       .......... .......... .......... ..QY...... ..........
FCG1_c        .......... .......... K...H..... ..QY...... ..........

250
FCG1_a        PLLEGNLVTL SCETKLLLQR PGLQLYFSFY MGSKTLRGRN TSSEYQILTA
                                       Ig 3
FCG1_b1       .......... .......... ...*
FCG1_c        ...GGIWSP*

▼
                                             |                            300
FCG1_a        RREDSGLYWC EAATEDGNVL KRSPELELQV LGLQLPTPVW FHVLFYLAVG
                                             |

350
FCG1_a        IMFLVNTVLW VTIRKELKRK KKWDLEISLD SGHEKKVISS LQEDRHLEEE
FCG1_b2       .......... .......... .......... ..GQALEAPT QGCA*

374
FCG1_a        LKCQEQKEEQ LQEGVHRKEP QGAT*                                   X
              intron location
```

SOLUBLE HYBRID FCγ RECEPTORS AND RELATED METHODS

BACKGROUND OF THE INVENTION

Immune system diseases are significant health-care problems that are growing at epidemic proportions. As such, they require novel, aggressive approaches to the development of new therapeutic agents. Standard therapy for autoimmune disease has been high dose, long-term systemic corticosteroids and immunosuppressive agents. The drugs used fall into three major categories: (1) glucocorticoids, such as prednisone and prednisolone; (2) calcineurin inhibitors, such as cyclosporine and tacrolimus; and (3) antiproliferative/antimetabolic agents such as azathioprine, sirolimus, and mycophenolate mofetil. Although these drugs have met with high clinical success in treating a number of autoimmune conditions, such therapies require lifelong use and act nonspecifically to suppress the entire immune system. The patients are thus exposed to significantly higher risks of infection and cancer. The calcineurin inhibitors and steroids are also nephrotoxic and diabetogenic, which has limited their clinical utility (Haynes and Fauci in *Harrison's Principles of Internal Medicine*, 16$^{th}$ edition, Kasper et al., eds (2005), pp 1907-2066).

In addition to the conventional therapies for autoimmune disease, monoclonal antibodies and soluble receptors that target cytokines and their receptors have shown efficacy in a variety of autoimmune and inflammation diseases such as rheumatoid arthritis, organ transplantation, and Crohn's disease. Some of the agents include infliximab (REMICADE®) and etanercept (ENBREL®) that target tumor necrosis factor (TNF), muromonab-CD3 (ORTHOCLONE OKT3) that targets the T cell antigen CD3, and daclizumab (ZENAPAX®) that binds to CD25 on activated T cells, inhibiting signaling through this pathway. While efficacious in treating certain inflammatory conditions, use of these drugs has been limited by side effects including the "cytokine release syndrome" and an increased risk of infection (Krensky et al., in *Goodman and Gilman's The Pharmacological Basis of Therapeutics*, 10$^{th}$ edition, Hardman and Limbird, eds, (2001), pp 1463-1484).

Passive immunization with intravenous immunoglobulin (IVIG) was licensed in the United States in 1981 for replacement therapy in patients with primary antibody deficiencies. Subsequent investigation showed that IVIG was also effective in ameliorating autoimmune symptoms in Kawasaki's disease and immune thrombocytopenia purpura (Lemieux et al., *Mol. Immunol.*, 42:839-848, 2005; Ibanez and Montoro-Ronsano *Curr. Pharm. Biotech.*, 4:239-247, 2003; Clynes, *J. Clin. Invest.*, 115:25-27, 2005). IVIG has also been shown to reduce inflammation in adult dermatomyositis, Guillian-Barre syndrome, chronic inflammatory demyelinating polyneuropathies, multiple sclerosis, vasculitis, uveitis, myasthenia gravis, and in the Lambert-Eaton syndrome (Lemieux et al., supra; Ibanez and Montoro-Ronsano, supra).

IVIG is obtained from the plasma of large numbers (10,000-20,000) of healthy donors by cold ethanol fractionation. Commonly used IVIG preparations include Sandoglobulin, Flebogamma, Gammagard, Octagam, and Vigam S. In general, efficacy is seen when only large amounts of IVIG are infused into a patient, with an average dose of 2 g/kg/month used in autoimmune disease. The common (1-10%) of patients) side effects of IVIG treatment include flushing, fever, myalgia, back pain, headache, nausea, vomiting, arthralgia, and dizziness. Uncommon (0.1-1% of patients) side effects include anaphylaxis, aseptic meningitis, acute renal failure, haemolytic anemia, and eczema. Although IVIG is generally considered safe, the pooled human plasma source is considered to be a risk factor for transfer of infectious agents. Thus, the use of IVIG is limited by its availability, high cost ($100/gm, including infusion cost), and the potential for severe adverse reactions (Lemieux et al., supra; Ibanez and Montoro-Ronsano, supra; Clynes, *J. Clin. Invest.*, 115:25-27, 2005).

Numerous mechanisms have been proposed to explain the mode of action of IVIG, including regulation of Fc gamma receptor expression, increased clearance of pathogenic antibodies due to saturation of the neonatal Fc receptor FcRn, attenuation of complement-mediated damage, and modulation of T and B cells or the reticuloendothelial system (Clynes, supra). Since Fc domains purified from IVIG are as active as intact IgG in a number of in vitro and in vivo models of inflammation, it is well accepted that the anti-inflammatory properties of IVIG reside in the Fc domain of the IgG (Debre et al., *Lancet*, 342:945-949, 1993) or a sialylated subfraction (Kaneko et al., *Science*, 313:670-673, 2006).

Fc receptors for IgG (FcγR) play a unique role in mammalian biology by acting as a bridge between the innate and the acquired immune systems (Dijstelbloem et al., *Trends Immunol.* 22:510-516, 2001; Takai, *Nature* 2: 580-592, 2002; Nimmerjahn and Ravetch, *Immunity* 24: 19-28, 2006). By virtue of their binding to the Fc region of IgG (Woof and Burton, *Nature Rev. Immunol.*, 4:1-11, 2004), FcγR regulate a variety of effector functions in ADCC, complement-mediated cell lysis, type III hypersensitivity reactions, tolerance, phagocytosis, antigen presentation, and the processing and clearance of immune complexes (Dijstelbloem et al., supra; Takai, supra; Nimmerjahn and Ravetch, supra).

The FcγR comprise three major gene families in humans including FcγRI (CD64), FcγRII (CD32), and FcγRIII (CD16) (Dijstelbloem et al., supra; Takai, supra). FcγRI is a high affinity receptor for monomeric IgG ($10^8$-$10^9$ M$^{-1}$) where FcγRII and FcγRIII exhibit low affinities for monomeric IgG ($10^7$ M$^{-1}$) but bind to IgG immune complexes with greatly increased avidities. The FcγRII subfamily is composed of two major classes of genes, FcγRIIa and FcγRIIb, which after binding IgG transmit opposing signals to the cell interior. FcγRIIa contains an immunoreceptor tyrosine-activating motif (ITAM) within its short cytoplasmic tail, while FcγRIIIb transmits inhibitory signals through an immunoreceptor tyrosine inhibitory motif (ITIM) within its cytoplasmic domain. FcγRIII subfamily also contains two distinct receptor genes, FcγRIIIa and FcγRIIIb. FcγRIIIa is a heterodimeric signaling receptor that after binding IgG immune complexes transmits activating signals through its associated ITAM-containing common γ chain. FcγRIIIb is bound to the cell membrane through a GPI linker and lacks intrinsic signaling capacity. FcγRI also lacks an intrinsic signaling capacity but similar to FcγRIIIa, associates with the common γ chain to transmit activating signals upon Fc binding. Signaling through FcγR involves kinase mediated phosphorylation/dephosphorylation events within the ITAM/ITIM sequences (Dacron, *Intern. Rev. Immunol.*, 16: 1-27, 1997).

Consistent with their reported roles in immune biology, the human FcγR exhibit different affinities for subclasses of monomeric IgG: FcγRI binds IgG1≥IgG3>IgG4>>IgG2; FcγRIIa binds IgG3≥IgG1, IgG2>>IgG4; FcγRIIb binds IgG3≥IgG1>IgG4>IgG2; FcγRIIIa and FcγRIIIb bind IgG1, IgG3>>IgG2, IgG4 (Dijstelbloem et al., supra; Takai, supra).

In addition to differences in structure and signaling capacities, the FcγR also exhibit differences in cellular expression patterns. In humans, FcγRI is expressed predominantly on macrophages, monocytes, and neutrophils but can also be found on eosinophils and dendritic cells. FcγRIIa is the most widely expressed FcγR in humans and is expressed on platelets, macrophages, neutrophils, eosinophils, dendritic cells and Langerhans cells. FcγRIIb is the only FcγR expressed on B cells but is also expressed by mast cells, basophils, macrophages, eosinophils, neutrophils, dendritic and langerhan cells. FcγRIIIa is the only FcγR expressed on human NK cells and is widely expressed, found on macrophages, monocytes, mast cells, eosinophils, dendritic and langerhan cells. The expression of FcγRIIIb, on the other hand is largely restricted to neutrophils and eosinophils (Dijstelbloem et al., supra; Takai, supra).

Mice express FcγR that function similarly to the receptors in humans such as the orthologs of human high affinity FcγRI and the inhibitory receptor FcγRIIb (Nimmerjahn and Ravetch, *Immunity*, 24:19-28, 2006). The murine orthologs of human FcγRIIa and IIIa are thought to be FcγRII and FcγRIV, respectively. Mice do not appear to express FcγRIIIb (Nimmerjahn and Ravetch, supra). Although some differences in cellular expression patterns have been noted, FcγR gene expression in humans and their orthologs in mice are generally similar.

Gene targeting in mice has suggested the importance of FcγR in the mammalian immune system (see generally Dijstelbloem et al., supra; Takai, supra; Nimmerjahn and Ravetch, supra). Deletion of the common γ chain, the signaling subunit of FcγRI, FcγRIII, and FcγRIV, abolishes signaling through all activating FcγR and renders mice resistant to a variety of autoimmune and inflammatory conditions. Mice deficient in the γ-chain exhibit attenuated immune complex-alveolitis, vasculitis, glomerulonephritis, Arthus reaction, and autoimmune hemolytic anemia. Similar data have been described for deletion of the α-chains of FcγRII and FcγRI. FcγRIII−/− mice exhibit reduced immune complex-induced alveolitis, reduced sensitivity to autoimmune hemolytic anemia and an attenuated Arthus reaction. FcγRI−/− mice show impaired phagocytic function of macrophages, decreased cytokine release, attenuated ADCC and antigen presentation, reduced arthritis, enhanced antibody responses, and impaired hypersensitivity. Deletion of the inhibitory receptor, FcγRIIb, in contrast, results in augmented inflammation and autoimmune responses. FcγRIIb−/− mice show enhanced collagen-induced arthritis, spontaneous development of glomerulonephritis on a C57BL/6 background, enhanced Arthus reaction, enhanced alveolitis, enhanced IgG-induced systemic anaphylaxis, and enhanced anti-GBM induced glomerulonephritis. Thus, the FcγR play key roles in immune system homeostasis.

There is a need for Fc receptor antagonists, including FcγRI antagonsists, useful in treating a variety of autoimmune diseases. Specifically, such antagonists would function to regulate the immune and hematopoietic systems, since disturbances of such regulation may be involved in disorders relating to inflammation, hemostasis, arthritis, immunodeficiency, and other immune and hematopoietic system anomalies. Therefore, there is a need for identification and characterization of such antagonists that can be used to prevent, ameliorate, or correct such disorders.

BRIEF SUMMARY OF THE INVENTION

In one aspect, the present invention provides a soluble hybrid Fcγ receptor (FcγR) polypeptide comprising an amino acid sequence that is at least 70%, at least 80%, at least 90%, at least 95%, at least 96%, at least 97%, at least 98%, or at least 99% or more identical to amino acid residues 35-301, 36-301, or 39-301 of SEQ ID NO:40; amino acid residues 43-310 or 48-310 of SEQ ID NO:42; amino acid residues 18-286, 21-286, or 24-286 of SEQ ID NO:44; or amino acid residues 18-286, 21-286, or 24-286 of SEQ ID NO:46, wherein the isolated polypeptide is capable of specifically binding to the Fc domain of IgG (e.g., human IgG such as, for example, human IgG1). As described herein, soluble hybrid FcγR polypeptides of the invention are capable of neutralizing IgG- or immune-complex-mediated signaling in immune cells. In some embodiments, the hybrid FcγR polypeptide comprises amino acid residues 35-301, 36-301, 39-301, 1-301, 35-311, 36-311, 39-311, or 1-311 of SEQ ID NO:40; amino acid residues 43-310, 48-310, 1-310, 43-320, 48-320, or 1-320 of SEQ ID NO:42; amino acid residues 18-286, 21-286, 24-286, 1-286, 18-296, 21-296, 24-296, or 1-296 of SEQ ID NO:44; or amino acid residues 18-286, 21-286, 24-286, 1-286, 18-296, 21-296, 24-296, or 1-296 of SEQ ID NO:46.

In another aspect, the present invention provides an isolated polynucleotide that encodes a soluble hybrid FcγR polypeptide as described herein. Generally, an isolated polynucleotide of the invention encodes a soluble FcγR polypeptide comprising an amino acid sequence that is at least 70%, at least 80%, at least 90%, at least 95%, at least 96%, at least 97%, at least 98%, or at least 99% or more identical to amino acid residues 35-301, 36-301, or 39-301 of SEQ ID NO:40; amino acid residues 43-310 or 48-310 of SEQ ID NO:42; amino acid residues 18-286, 21-286, or 24-286 of SEQ ID NO:44; or amino acid residues 18-286, 21-286, or 24-286 of SEQ ID NO:46, wherein the encoded polypeptide is capable of specifically binding to the Fc domain of IgG (e.g., human IgG such as, for example, human IgG1). In some embodiments, the encoded polypeptide comprises amino acid residues 35-301, 36-301, or 39-301, 1-301, 35-311, 36-311, 39-311, or 1-311 of SEQ ID NO:40; amino acid residues 43-310, 48-310, 1-310, 43-320, 48-320, or 1-320 of SEQ ID NO:42; amino acid residues 18-286, 21-286, 24-286, 1-286, 18-296, 21-296, 24-296, or 1-296 of SEQ ID NO:44; or amino acid residues 18-286, 21-286, 24-286, 1-286, 18-296, 21-296, 24-296, or 1-296 of SEQ ID NO:46. In specific variations, the nucleic acid comprises nucleotide residues 103-903, 106-903, 115-903, 1-903, 103-933, 106-933, 115-933, or 1-933 of SEQ ID NO:39; nucleotide residues 127-930, 142-930, 1-930, 127-960, 142-960, or 1-960 of SEQ ID NO:41; nucleotide residues 52-858, 61-858, 70-858, 1-858, 52-888, 61-888, 70-888, or 1-888 of SEQ ID NO:43; or nucleotide residues 52-858, 61-858, 70-858, 1-858, 52-888, 61-888, 70-888, or 1-888 of SEQ ID NO:45.

Within another aspect, the present invention provides an expression vector comprising the following operably linked elements: (a) a transcription promoter; a first DNA segment encoding a soluble FcγR polypeptide comprising an amino acid sequence that is at least 70%, at least 80%, at least 90%, at least 95%, at least 96%, at least 97%, at least 98%, or at least 99% or more identical to amino acid residues 35-301, 36-301, or 39-301 of SEQ ID NO:40; amino acid residues 43-310 or 48-310 of SEQ ID NO:42; amino acid residues 18-286, 21-286, 24-286 of SEQ ID NO:44; or amino acid residues 18-286, 21-286, or 24-286 of SEQ ID NO:46, wherein the encoded polypeptide is capable of specifically binding to the Fc domain of IgG (e.g., human IgG such as, for example, human IgG1); and a transcription terminator. In certain embodiments, the expression vector disclosed above further comprises a secretory signal sequence operably linked to the first DNA segment (e.g., a DNA sequence encoding amino acid residues 1-34 or 1-35 of SEQ ID NO:40, amino acid residues 1-42 of SEQ ID NO:42, amino acid residues 1-17 or 1-20 of SEQ ID NO:44; amino acid residues 1-17 or 1-20 of SEQ ID NO:46, amino acid residues 1-35 of SEQ ID NO:60, amino acid residues 1-16 of SEQ ID NO:62, amino acid residues 1-19 of SEQ ID NO:64, or amino acid residues 1-23 of SEQ ID NO:66). In some embodiments, the encoded polypeptide comprises amino acid residues 35-301, 36-301, 39-301, 1-301, 35-311, 36-311, 39-311, or 1-311 of SEQ ID NO:40; amino acid residues 43-310, 48-310, 1-310, 43-320, 48-320, or 1-320 of SEQ ID NO:42; amino acid residues 18-286, 21-286, 24286, 1-286, 18-296, 21-296, 24-296, or 1-296 of SEQ ID NO:44; amino acid residues 18-286, 21-286, 24-286, 1-286, 18-296, 21-296, 24-296, or 1-296 of SEQ ID NO:46; amino acid residues 36-301 or 1-301 of SEQ ID NO:60; or amino acid residues 24-289 or 1-289 of SEQ ID NO:66. In specific variations, the DNA segment encoding the polypeptide comprises nucleotide residues 103-903, 106-903, 115-903, 1-903, 103-933, 106-933, 115-933, or 1-933 of SEQ ID NO:39; nucleotide residues 127-930, 142-930, 1-930, 127-960, 142-960, or 1-960 of SEQ ID NO:41; nucleotide residues 52-858, 61-858, 70-858, 1-858, 52-888, 61-888, 70-888, or 1-888 of SEQ ID NO:43; nucleotide residues 52-858, 61-858, 70-858, 1-858, 52-888, 61-888, 70-888, or 1-888 of SEQ ID NO:45; nucleotide residues 106-903 or 1-903 of SEQ ID NO:59; or nucleotide residues 70-867 or 1-867 of SEQ ID NO:65.

Within another aspect, the present invention provides a cultured cell comprising an expression vector as disclosed above, wherein the cell expresses the soluble FcγR polypeptide encoded by the DNA segments. In another embodiment, the cultured cell is as disclosed above, wherein the cell secretes a soluble FcγR polypeptide. In another embodiment, the cultured cell is as disclosed above, wherein the cell secretes a soluble FcγR polypeptide that binds IgG or antagonizes IgG activity, where the IgG is present in a monomeric form or as a multimeric immune complex. In particular variations, the cultured cell is a mammalian cell such as, for example, a Chinese Hamster ovary (CHO) cell.

Within another aspect, the present invention provides a method of producing a soluble hybrid FcγR polypeptide comprising the following steps: (a) culturing a cell as disclosed above; and (b) isolating the soluble FcγR polypeptide produced by the cell. In some embodiments, the method comprises culturing a cell into which has been introduced an expression vector as above, wherein the cell expresses the polypeptide encoded by the DNA segment, and recovering the expressed polypeptide. In certain variations, the expression vector further includes a secretory signal sequence operably linked to the DNA segment, wherein the cell expresses the polypeptide encoded by the DNA segment, and wherein the polypeptide is secreted from the cell and recovered.

Within another aspect, the present invention provides pharmaceutical compositions comprising a pharmaceutically acceptable carrier and a soluble hybrid FcγR polypeptide of the invention.

Within another aspect, the present invention also provides fusion proteins comprising a soluble hybrid FcγR polypeptide and a heterologous polypeptide segment. Particularly suitable heterologous polypeptide segments include immunoglobulin moieties. In certain variations, the immunoglobulin moiety is an immunoglobulin heavy chain constant region, such as a human Fc fragment. The present invention further includes isolated nucleic acid molecules that encode such fusion proteins.

Within another aspect, the present invention provides a method for inhibiting IgG- or immune complex-induced proliferation of hematopoietic cells and hematopoietic cell progenitors comprising culturing bone marrow or peripheral blood cells with a composition comprising an amount of soluble FcγR sufficient to reduce proliferation of the hematopoietic cells in the bone marrow or peripheral blood cells as compared to bone marrow or peripheral blood cells cultured in the absence of soluble receptor. In one embodiment, the method is as disclosed above, wherein the hematopoietic cells and hematopoietic progenitor cells are lymphoid cells. In one embodiment, the method is as disclosed above, wherein the lymphoid cells are macrophages, B cells, or T cells. Within another aspect, the present invention provides a method for inhibiting antigen presentation by cells of the myeloid lineage such as macrophages or monocytes with a composition comprising an amount of soluble FcγR sufficient to reduce antigen presentation by myeloid-derived cells. In another embodiment, the method is as disclosed wherein the cells are B cells.

Within another aspect, the present invention provides a method of reducing IgG-mediated or immune-complex-mediated inflammation comprising administering to a mammal with inflammation an amount of a composition of a soluble FcγR sufficient to reduce inflammation.

Within another aspect, the present invention provides a method of suppressing an immune response in a mammal comprising administering a composition comprising a soluble FcγR polypeptide in an acceptable pharmaceutical vehicle.

Moreover, blocking the interaction between cell surface FcγR and the IgG Fc domains of immune complexes would attenuate the cellular response to the immune complexes and thus reduce inflammation. As such, the soluble FcγR polypeptides of the present invention, which as shown herein are effective in blocking IgG- and immune-complex-mediated immune responses, are useful in therapeutic treatment of inflammatory diseases such as, for example, arthritis (e.g., rheumatoid arthritis or psoriatic arthritis), adult respiratory disease (ARD), endotoxemia, septic shock, multiple organ failure, inflammatory lung injury (e.g., asthma or bronchitis), bacterial pneumonia, psoriasis, eczema, atopic and contact dermatitis, inflammatory bowel disease (IBD) (e.g., ulcerative colitis or Crohn's disease), and aberrant immune responses to bacterial or viral infection.

These and other aspects of the invention will become evident upon reference to the following detailed description. In addition, various references are identified herein are incorporated by reference in their entirety.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

In the polypeptide context, the term "fragment" refers to a portion of a polypeptide typically having at least 20 contiguous or at least 50 contiguous amino acids of the polypeptide. A "variant" includes a polypeptide or fragment thereof having amino acid substitutions (e.g., conservative amino acid substitutions) relative to a second polypeptide; or a polypeptide or fragment thereof that is modified by covalent attachment of a second molecule such as, e.g., by attachment of a heterologous polypeptide, or by glycosylation, acetylation, phosphorylation, and the like. Further included within the definition of "polypeptide" is, for example, polypeptides containing one or more analogs of an amino acid (e.g., unnatural amino acids and the like), polypeptides with unsubstituted linkages, as well as other modifications known in the art, both naturally and non-naturally occurring.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces a soluble hybrid FcγR from an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of an FcγR polypeptide fused with a polypeptide that binds an affinity matrix. Such a fusion protein provides a means to isolate large quantities of FcγRIA using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear, monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

A "soluble receptor" is a receptor polypeptide that is not bound to a cell membrane. Soluble receptors are most commonly ligand-binding receptor polypeptides that lack transmembrane and cytoplasmic domains, and other linkage to the cell membrane such as via glycophosphoinositol (gpi). Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Soluble receptors can be monomeric, homodimeric, heterodimeric, or multimeric, with multimeric receptors generally not comprising more than 9 subunits, preferably not comprising more than 6 subunits, and most preferably not comprising more than 3, subunits. Receptor polypeptides are said to be substantially free of transmembrane and intracellular polypeptide segments when they lack sufficient portions of these segments to provide membrane anchoring or signal transduction, respectively. Moreover, one of skill in the art using the genetic code can readily determine polynucleotides that encode such soluble receptor polyptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and the like, as well as synthetic analogs of these molecules.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See generally Ford et al., *Protein Expression and Purification* 2:95 (1991). DNA molecules encoding affinity tags are available from commercial suppliers (e.g., Pharmacia Biotech, Piscataway, N.J.).

In the context of Fcγ receptor polypeptides or polypeptide regions, "correspondence" to another sequence (e.g., regions, fragments, nucleotide or amino acid positions, or the like) is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to an "amino acid position corresponding to amino acid position [X]" of a specified Fcγ receptor protein represents, in addition to referral to amino acid positions of the specified Fcγ receptor protein, referral to a collection of equivalent positions in other recognized Fcγ receptor proteins and structural homologues and families.

The terms "identical" or "percent identity," in the context of two or more nucleic acids or polypeptide sequences, refer to two or more sequences or subsequences that are the same or have a specified percentage of nucleotides or amino acid residues that are the same (e.g., at least 60% identity, optionally at least 65%, at least 70%, at least 75%, at least 80%, at least 85%, at least 90%, or at least 95% identity over a specified region), when compared and aligned for maximum correspondence over a comparison window, or designated region as measured using one of the following sequence comparison algorithms or by manual alignment and visual inspection. Sequences are "substantially identical" to each other if they are at least 70%, at least 80%, at least 90%, at least 95%, at least 96%, at least 97%, at least 98%, or at least 99% identical. These definitions also refer to the complement of a test sequence. Optionally, the identity exists over a region that is at least about 50 nucleotides in length, or more typically over a region that is 100 to 500 or 1000 or more nucleotides in length.

Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art. (See, e.g., Peruski and Perusdi, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two nucleotide or amino acid sequences are considered to have "substantially similar sequence identity" or "substantial sequence identity" if the two sequences have at least 80%, at least 90%, or at least 95% sequence identity relative to each other.

Percent sequence identity is determined by conventional methods. See, e.g., Altschul et al., *Bull. Math. Bio.* 48:603, 1986, and Henikoff and Henikoff, *Proc. Natl. Acad. Sci. USA* 89:10915, 1992. For example, two amino acid sequences can be aligned to optimize the alignment scores using a gap opening penalty of 10, a gap extension penalty of 1, and the "BLOSUM62" scoring matrix of Henikoff and Henikoff, supra, as shown in Table 1 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 1

BLOSUM62 Scoring Matrix

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and a second amino acid sequence. The FASTA algorithm is described by Pearson and Lipman, *Proc. Nat'l Acad. Sci. USA* 85:2444, 1988, and by Pearson, *Meth. Enzymol.* 183:63, 1990. Briefly, FASTA first characterizes sequence similarity by identifying regions shared by the query sequence (e.g., residues 39-301 of SEQ ID NO:40, residues 48-310 of SEQ ID NO:42, residues 24-286 of SEQ ID NO:44, or residues 24-286 of SEQ ID NO:46) and a test sequence that have either the highest density of identities (if the ktup variable is 1) or pairs of identities (if ktup-2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63, 1990.

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

"Conservative amino acid substitution" generally refers to an amino acid substitution represented by a BLOSUM62 value of greater than -1. The BLOSUM62 table (Table 1, supra) is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915, 1992). Accordingly, the BLOSUM62 substitution frequencies can be used to define conservative amino acid substitutions that may be introduced into a particular amino acid sequence. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

"Corresponding to," when used in reference to a nucleotide or amino acid sequence, indicates the position in a second sequence that aligns with the reference position when two sequences are optimally aligned.

With regard to FcγR polypeptides as described herein, reference to amino acid residues corresponding to those specified by SEQ ID NO includes post-translational modifications of such residues. For example, reference to a glutamine at a position corresponding to position 16 of SEQ ID NO:2 encompasses a post-translational modification of this glutamine to pyro-glutamic acid.

"Immune complex," as used herein, refers to a complex that forms upon binding of an IgG antibody to its cognate antigen. The term "immune complex" as used herein encompasses all stoichiometries of antigen:antibody complexes. For example, an immune complex may comprise a single IgG antibody (monomeric IgG) bound to antigen or may comprise multiple IgG antibodies bound to antigen (multimeric immune complex).

"IgG-mediated inflammation," as used herein, refers to an inflammatory response mediated at least in part by the binding of an immune complex to an Fcγ receptor via the Fc region of an IgG antibody contained within the immune complex. "IgG-mediated inflammation" also encompasses the activation of the complement pathway by IgG immune complexes.

"Immune complex-mediated inflammation," as used herein, refers to IgG-mediated inflammation characterized at least in part by the deposition of immune complexes within one or more tissues.

"IgG-mediated disease" or "IgG-mediated inflammatory disease," as used herein, refers to an inflammatory disease mediated at least in part by the binding of an immune complex to an Fcγ receptor via the Fc region of an IgG antibody contained within the immune complex. "IgG-mediated disease" or "IgG-mediated inflammatory disease" also encompasses diseases characterized at least in part by the activation of the complement pathway by IgG immune complexes.

"Autoimmune disease," as used herein, refers to an IgG-mediated inflammatory disease characterized at least in part by the presence of IgG autoantibodies, i.e., IgG antibodies specific for one or more self-antigens. Autoimmune diseases include, for example, diseases associated with autoantibody production as well as the deposition of immune complexes in one or more tissues; such diseases include, e.g., systemic lupus erythematosus (SLE), rheumatoid arthritis (RA), and mixed connective tissue disease. Autoimmune diseases also include those diseases associated with autoantibody production although not clearly associated with deposition of immune complexes, such as, for example, idiopathic thrombocytopenia purpura (ITP), Sjogren's Syndrome, antiphospholipid antibody syndrome, dermatomyositis, Guillain-Barre Syndrome, and Goodpasture's Syndrome. Other autoimmune diseases include, e.g., inflammatory bowel disease (IBD), psoriasis, atopic dermatitis, myasthenia gravis, type I diabetes, and multiple sclerosis.

"Immune complex-mediated disease," as used herein, refers to an IgG-mediated inflammatory disease characterized at least in part by the deposition of immune complexes within one or more tissues. Immune complex-mediated diseases include, for example, mixed cryoglubulinemia; systemic lupus erythematosus (SLE); rheumatoid arthritis (RA); mixed connective tissue disease; and diseases associated with exonegous antigens such as, e.g., HBV-associated polyarteritis nodosa.

Due to the imprecision of standard analytical methods, molecular weights and lengths of polymers are understood to be approximate values. When such a value is expressed as "about" X or "approximately" X, the stated value of X will be understood to be accurate to 110%.

BRIEF DESCRIPTION OF THE DRAWINGS

FIGS. 6A-6D depict FcγRI sequences. FIG. 6A shows a polynucleotide sequence encoding FcγRIA (FcγRI isoform a) (SEQ ID NO:1). FIG. 6B shows the polypeptide sequence of FcγRIA (SEQ ID NO:2). FIG. 6C shows the polypeptide sequence of the extracellular domain of FcγRIA (SEQ ID NO:3). FIG. 6D shows a comparison of FcγRIA polypeptide sequence with FcγRI isoforms b1 (SEQ ID NO:4) and c (SEQ ID NO:5) polypeptide sequences. The vertical lines in FIG. 6D indicate where the introns are located in the corresponding gene; the triangle indicates the C-terminal amino acid of a particular embodiment of soluble FcγRIA or, alternatively, a C-terminal fusion site for certain tagged variations of soluble FcγRIA (e.g., His6-tagged FcγRIA). "16" above glutamine (Q) at amino acid position 16 in FIG. 6D indicates the amino terminal start site for the mature FcγRIA protein.

FIGS. 16A and 16B), or one of the soluble hybrid receptors, FcγRIIA/IA-CH6 ("FCGR2A 1A"; FIG. 16A) and FcγRIIIA/IA-CH6 ("FCGR3A IA"; FIG. 16B), and neutrophil infiltration was assessed by measuring myeloperoxidase activity in the punch biopsy samples. Each point represents the mean±SD for n=6 animals per group. Difference significant, *p<0.001 by ANOVA, **p<0.001 by the Mann-Whitney test.

DESCRIPTION OF THE INVENTION

I. Overview

Figure 1:
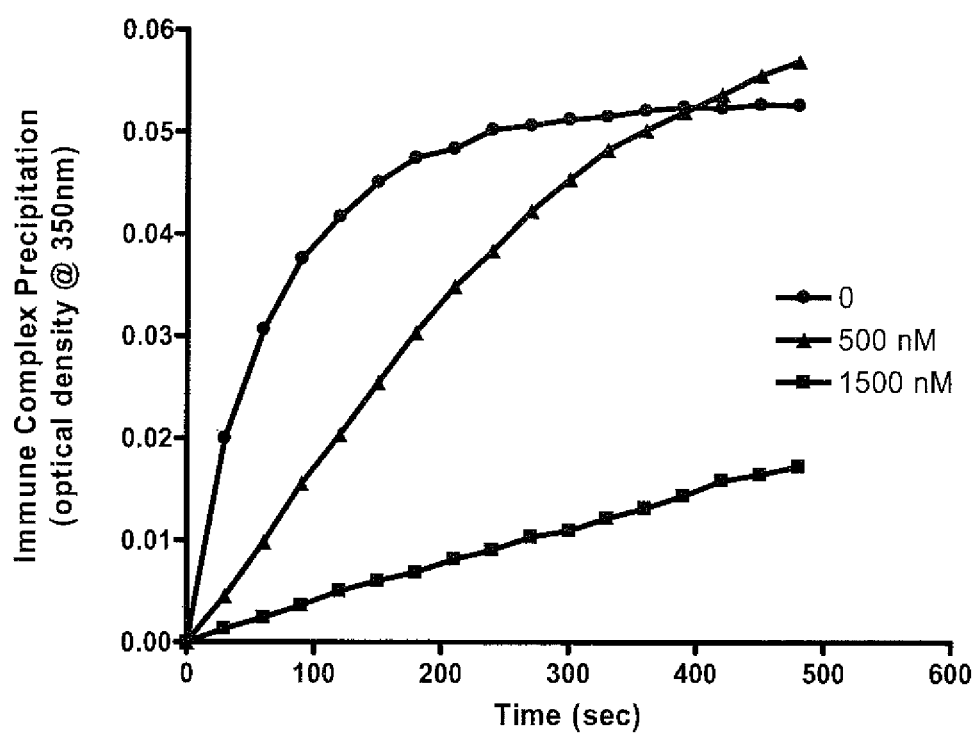
FIG. 1 depicts blocking of immune complex precipitation in vitro with FcγRIA-CH6. Anti-OVA/OVA immune complex precipitation assays were carried out as described in Example 9, infra. Each point represents the mean values of three separate experiments performed in duplicate. Circles: anti-OVA+OVA; triangles: anti-OVA+OVA+500 nM FcγRIA-CH6; squares: anti-OVA+OVA+1500 nM FcγRIA-CH6.

The present invention fills a need for novel therapeutics for treating IgG- and immune complex-mediated disease by providing Fcγ receptor antagonists. In particular, Fcγ receptor antagonists in accordance with the present invention are soluble hybrid receptors comprising a modified extracellular domain of FcγRIA in which the first Ig domain (D1) is substituted with the first Ig domain of FcγRIIA, FcγRIIB, FcγRIIA, or FcγRIIIB. Such hybrid receptors maintain the high affinity binding of the native FcγRIA and may be used in methods for reducing IgG-mediated inflammation, including inflammatory processes mediated by immune complex precipitation.

It was discovered that soluble FcγRIA, but not soluble FcγRIIA or FcγRIIA, blocked inflammation in the cutaneous Arthus reaction (see Examples 9 and 10). Additionally, it was discovered that soluble FcγRIA also blocked the binding and signaling of immune complexes (described in detail in the Examples below) through cellular FcγR. The findings that soluble FcγRIA blocked inflammation in the cutaneous Arthus reaction, in the collagen antibody-induced model of arthritis, and in collagen-induced arthritis in mice were surprising, since FcγRIA, as a high affinity receptor for IgG Fc, is expected to be saturated with monomeric IgG in the circulation and hence generally less available for binding to immune complexes. These findings show that soluble FcγRIA is a potent therapeutic that can be used to treat autoimmune disease and inflammation. Further, these results support the use of other soluble, high-affinity receptors for Fcγ, including the hybrid Fcγ receptors as described herein, for treating such conditions.

Accordingly, the soluble Fcγ receptor polypeptides described herein are useful to antagonize or block signaling of IgG and immune complexes in immune cells (e.g., lymphocytes, monocytes, leukocytes, macrohages and NK cells) for the treatment of IgG- and immune complex-mediated diseases such as, for example, autoimmune diabetes, multiple sclerosis (MS), systemic Lupus erythematosus (SLE), myasthenia gravis, Wegener's granulomatosis, Churg-Strauss syndrome, hepatitis-B-associated polyarteritis nodosa, microscopic polyangiitis, Henoch-Schonlein purpura, rheumatoid arthritis (RA), Lambert-Eaton syndrome, inflammatory bowel disease (IBD), essential mixed cryoglobulinemia, hepatitis-C-associated cryoglobulinemia, mixed connective tissue disease, autoimmune thrombocytopenias (ITP and TTP), adult dermatomyositis, Guillian-Barre syndrome, Sjogren's syndrome, Goodpasture's syndrome, chronic inflammatory demyelinating polyneuropathies, anti-phospholipid antibody syndrome, vasculitis, uveitis, serum sickness, pemphigus (e.g., pemphigus vulgaris), and diseases associated with exogenous antigens, such as viral and bacterial infections. Asthma, allergy, and other atopic disease may also be treated with the soluble Fcγ receptor polypeptides of the invention to inhibit the immune response or to deplete offending cells. Blocking or inhibiting signaling of IgG and immune complexes via Fcγ receptors, by using the soluble Fcγ receptor polypeptides of the present invention, may also benefit diseases of the pancreas, kidney, pituitary, and neuronal cells. The soluble Fcγ receptor polypeptides of the present invention are useful as antagonists of IgG and immune complexes. Such antagonistic effects can be achieved by direct neutralization or binding of the Fc domains IgG and immune complexes.

II. Soluble Hybrid Fcγ Receptors and Methods and Materials for Making Them

Accordingly, in one aspect, the present invention provides isolated, soluble hybrid Fcγ receptor (FcγR) polypeptides capable of neutralizing IgG- or immune-complex-mediated signaling in immune cells. The hybrid Fcγ receptors generally comprise polypeptide regions corresponding to the extracellular Ig domains of at least two different Fcγ receptor subfamilies and are substantially free of transmembrane and intracellular polypeptide segments. In particular, a soluble hybrid Fcγ receptor of the present invention generally comprises a modified extracellular domain of human FcγRIA in which the first Ig domain (D1) is substituted with a polypeptide region corresponding to the first Ig domain of human FcγRIIA, FcγRIIB, FcγRIIIA, or FcγRIIIB.

An illustrative nucleotide sequence that encodes human FcγRIA (isoform a of FcγRI) is provided by SEQ ID NO:1. SEQ ID NO:1 contains an open reading frame encoding 374 amino acids (SEQ ID NO:2) comprising an extracellular Fcγ-binding domain of approximately 277 amino acid residues (residues 16-292 of SEQ ID NO:2; SEQ ID NO:3). FcγRI also includes isoforms b1 and c, both of which are depicted in FIG. 6D as compared to FcγRIA (SEQ ID NO:2). The extracellular domain of isoforms b1 and c comprise only two Ig domains, as opposed to that of isoform a, which comprises three Ig domains. The first, second, and third Ig domains of FcγRIA correspond approximately to amino acid residues 22-101, 104-184, and 190-250 of SEQ ID NO:2, respectively.

An illustrative nucleotide sequence that encodes an extracellular domain of human FcγRIIA (isoform a of FcγRII) is provided by SEQ ID NO:6. SEQ ID NO:6 contains an open reading frame encoding 211 amino acids (SEQ ID NO:7) comprising a secretory signal sequence of approximately 34 or 35 amino acid residues (residues 1-34 or 1-35 of SEQ ID NO:7) and an extracellular Fcγ-binding domain of approximately 177 or 176 amino acid residues (residues 35-211 or 36-211 of SEQ ID NO:7). The extracellular domain of FcγRIIA comprises two Ig domains, corresponding approximately to amino acid residues 39-119 and 122-204 of SEQ ID NO:7, respectively.

An illustrative nucleotide sequence that encodes an extracellular domain of human FcγRIIB (isoform b of FcγRII) is provided by SEQ ID NO:8. SEQ ID NO:8 contains an open reading frame encoding 216 amino acids (SEQ ID NO:9) comprising a secretory signal sequence of approximately 42 amino acid residues (residues 1-42 of SEQ ID NO:9) and an extracellular Fcγ-binding domain of approximately 174 amino acid residues (residues 43-216 of SEQ ID NO:9). The extracellular domain of FcγRIIB comprises two Ig domains, corresponding approximately to amino acid residues 48-129 and 132-213 of SEQ ID NO:9, respectively.

An illustrative nucleotide sequence that encodes an extracellular domain of human FcγRIIIA (isoform a of FcγRIII) is provided by SEQ ID NO:10. SEQ ID NO:10 contains an open reading frame encoding 195 amino acids (SEQ ID NO:11) comprising a secretory signal sequence of approximately 17 or 20 amino acid residues (residues 1-17 or 1-20 of SEQ ID NO:11) and an extracellular Fcγ-binding domain of approximately 178 or 175 amino acid residues (residues 18-195 or 21-195 of SEQ ID NO:11). The extracellular domain of FcγRIIIA comprises two Ig domains, corresponding approximately to amino acid residues 24-105 and 108-189 of SEQ ID NO:11, respectively.

An illustrative nucleotide sequence that encodes an extracellular domain of human FcγRIIIB (isoform b of FcγRIII) is provided by SEQ ID NO:12. SEQ ID NO:12 contains an open reading frame encoding 195 amino acids (SEQ ID NO:13) comprising a secretory signal sequence of approximately 17 or 20 amino acid residues (residues 1-17 or 1-20 of SEQ ID NO:13) and an extracellular Fcγ-binding domain of approximately 178 or 175 amino acid residues (residues 18-195 or 21-195 of SEQ ID NO:13). The extracellular domaino of FcγRIIIB comprises two Ig domains, corresponding approximately to amino acid residues 24-105 and 108-189 of SEQ ID NO:13, respectively.

In certain embodiments, a soluble FcγR polypeptide of the invention comprises an amino acid sequence that is at least 70%, at least 80%, at least 90%, at least 95%, at least 96%, at least 97%, at least 98%, or at least 99% or more identical to amino acid residues 35-301, 36-301, or 39-301 of SEQ ID NO:40; amino acid residues 43-310 or 48-310 of SEQ ID NO:42; amino acid residues 18-286, 21-286, or 24-286 of SEQ ID NO:44; or amino acid residues 18-286, 21-286, or 24-286 of SEQ ID NO:46, wherein the isolated polypeptide is capable of specifically binding to the Fc domain of IgG (e.g., human IgG such as, for example, human IgG1). A soluble FcγR polypeptide of the invention specifically binds if it binds to monomeric human IgG (e.g., human IgG1) with a binding affinity ($K_a$) of at least $10^6$ $M^{-1}$, preferably at least $10^7$ $M^{-1}$, more preferably at least $10^8$ $M^{-1}$, and most preferably at least $10^9$ $M^{-1}$. In certain embodiments, a soluble FcγR polypeptide of the invention binds to monomeric human IgG with a binding affinity ($K_a$) of between $10^8$ $M^{-1}$ and $10^9$ $M^{-1}$. The binding affinity of a soluble FcγR polypeptide can be readily determined by one of ordinary skill in the art, for example, by Scatchard analysis (Scatchard, *Ann. NY Acad. Sci.* 51:660, 1949). In addition to determining an affinity constant ($K_a$), an alternative means of measuring affinity is the equilibrium constant ($K_d$), where a decrease would be observed with the improvement in affinity. In certain embodiments, a soluble FcγR polypeptide of the invention binds to human IgG1 with an equilibrium dissociation constant ($K_d$) of less than $10^{-8}$ M, preferably less than $10^{-9}$ M, and more preferably less than $10^{-10}$ M. In a specific variation, a soluble FcγR polypeptide of the invention binds to human IgG1 with an equilibrium dissociation constant ($K_d$) of about $1.7 \times 10^{-10}$ M. In some embodiments, a soluble FcγR polypeptide of the invention comprises amino acid residues 35-301, 36-301, or 39-301 of SEQ ID NO:40; amino acid residues 43-310 or 48-310 of SEQ ID NO:42; amino acid residues 18-286, 21-286, or 24-286 of SEQ ID NO:44; or amino acid residues 18-286, 21-286, or 24-286 of SEQ ID NO:46. In other embodiments, a soluble FcγR polypeptide of the invention comprises an amino acid sequence selected from (i) an amino acid sequence as shown in SEQ ID NO:40 from amino acid x to amino acid 301, wherein x is an integer from 35 to 39, inclusive; (ii) an amino acid sequence as shown in SEQ ID NO:42 from amino acid x to amino acid 310, wherein x is an integer from 43 to 48, inclusive; (iii) an amino acid sequence as shown in SEQ ID NO:44 from amino acid x to amino acid 286, wherein x is an integer from 18 to 24, inclusive; and (iv) an amino acid sequence as shown in SEQ ID NO:46 from amino acid x to amino acid 286, wherein x is an integer from 18 to 24, inclusive.

In some embodiments in which the amino acid sequence of the soluble hybrid FcγRI polypeptide shares at least 70%, at least 80%, at least 90%, at least 95%, at least 96%, at least 97%, at least 98%, or at least 99% or more identity with amino acid residues 35-301, 36-301, or 39-301 SEQ ID NO:40; amino acid residues 43-310 or 48-310 of SEQ ID NO:42; amino acid residues 18-286, 21-286, or 24-286 of SEQ ID NO:44; or amino acid residues 18-286, 21-286, or 24-286 of SEQ ID NO:46, any difference between the amino acid sequence of the FcγR polypeptide and the corresponding amino acid sequence of SEQ ID NO:40, SEQ ID NO:42, SEQ ID NO:44, or SEQ ID NO:46 is due to one or more conservative amino acid substitutions.

Polypeptides having substantial sequence identity relative to a reference polypeptide as shown in SEQ ID NO:40, 42, 44, or 46 are generally characterized as having one or more amino acid substitutions, deletions or additions relative to the reference polypeptide. These changes are preferably of a minor nature, that is conservative amino acid substitutions (see, e.g., Table 2, infra, which lists some exemplary conservative amino acid substitutions) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), or other antigenic epitope or binding domain. (See generally Ford et al., *Protein Expression and Purification* 2:95-107, 1991.) DNAs encoding affinity tags are available from commercial suppliers (e.g., Pharmacia Biotech, Piscataway, N.J.).

TABLE 2

| Conservative amino acid substitutions | |
| --- | --- |
| Basic: | arginine |
|  | lysine |
|  | histidine |
| Acidic: | glutamic acid |
|  | aspartic acid |
| Polar: | glutamine |
|  | asparagine |
| Hydrophobic: | leucine |
|  | isoleucine |
|  | valine |
| Aromatic: | phenylalanine |
|  | tryptophan |
|  | tyrosine |
| Small: | glycine |
|  | alanine |
|  | serine |
|  | threonine |
|  | methionine |

Essential amino acids in the receptor polypeptides of the present invention can be identified according to procedures known in the art, such as site-directed mutagenesis or alanine-scanning mutagenesis (Cunningham and Wells, *Science* 244:1081-1085, 1989; Bass et al., *Proc. Natl. Acad. Sci. USA* 88:4498-4502, 1991). In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-receptor interaction can also be determined by analysis of crystal structure as determined by such techniques as nuclear magnetic resonance, crystallography or photoaffinity labeling. (See, e.g., de Vos et al., *Science* 255:306-312, 1992; Smith et al., *J. Mol. Biol.* 224:899-904, 1992; Wlodaver et al., *FEBS Lett.* 309:59-64, 1992.) The identities of essential amino acids can also be inferred from analysis of homologies with related receptors.

Multiple amino acid substitutions can be made and tested using known methods of mutagenesis and screening, such as those disclosed by Reidhaar-Olson and Sauer *Science* 241: 53-57, 1988 or Bowie and Sauer *Proc. Natl. Acad. Sci. USA* 86:2152-2156, 1989. Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display e.g., Lowman et al., *Biochem.* 30:10832-10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis methods as disclosed above can be combined with high-throughput screening methods to detect activity of cloned, mutagenized receptors in host cells.

Preferred assays in this regard include cell proliferation assays and biosensor-based ligand-binding assays, which are described below. Mutagenized DNA molecules that encode active receptors or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that comprise a soluble FcγR polypeptide that is substantially identical to a reference polypeptide of amino acid residues 35-301, 36-301, or 39-301 of SEQ ID NO:40; amino acid residues 43-310 or 48-310 of SEQ ID NO:42; amino acid residues 18-286, 21-286, or 24-286 of SEQ ID NO:44; or amino acid residues 18-286, 21-286, or 24-286 of SEQ ID NO:46 and that retains the ligand-binding properties (i.e. IgG binding properties) of the reference polypeptide. Assay systems for determining ligand-binding properties of receptor polypeptides are generally known in the art and are readily adaptable for use in determining the Fcγ-binding properties of a soluble hybrid FcγR as described herein. Exemplary assays are further described herein.

For example, a preferred assay system employs a commercially available biosensor instrument (BIAcore™, Pharmacia Biosensor, Piscataway, N.J.), wherein a receptor polypeptide is immobilized onto the surface of a receptor chip. Use of this instrument is disclosed by Karlsson (*J. Immunol. Methods* 145:229-240, 1991) and Cunningham and Wells (*J. Mol. Biol.* 234:554-563, 1993). For use in accordance with the present invention, a soluble hybrid FcγR polypeptide is covalently attached, using amine or sulfhydryl chemistry, to dextran fibers that are attached to gold film within the flow cell. A test sample is passed through the cell. If ligand (e.g., IgG) is present in the sample, it will bind to the immobilized hybrid FcγR, causing a change in the refractive index of the medium, which is detected as a change in surface plasmon resonance of the gold film. This system allows the determination of on- and off-rates, from which binding affinity can be calculated, and assessment of stoichiometry of binding.

The soluble hybrid FcγR polypeptides can also be used within other assay systems known in the art. Such systems include Scatchard analysis for determination of binding affinity (see Scatchard, *Ann. NY Acad. Sci.* 51: 660-672, 1949) and calorimetric assays (see Cunningham et al., *Science* 253:545-548, 1991; Cunningham et al., *Science* 254:821-825, 1991).

Soluble hybrid FcγR polypeptides in accordance with the present invention may also include one or more additional polypeptide segment(s) that are not derived from a native FcγR. Accordingly, in some embodiments, a soluble hybrid FcγR polypeptide is a fusion protein further comprising a polypeptide segment heterologous to a Fcγ receptor. Particularly suitable heterologous polypeptides are dimerizing proteins as disclosed, e.g., in U.S. Pat. Nos. 5,155,027 and 5,567,584. Preferred dimerizing proteins in this regard include immunoglobulin constant region domains, e.g., IgGγ1, and the human κ light chain. Immunoglobulin-soluble FcγR polypeptide fusions can be expressed in genetically engineered cells to produce a variety of such receptor analogs. In certain variations, the dimerizing protein is an immunoglobulin heavy chain constant region, typically an Fc fragment, which contains two constant region domains and a hinge region but lacks the variable region (See Sledziewski et al., U.S. Pat. Nos. 6,018,026 and 5,750,375). Such fusions are typically secreted as multimeric molecules, wherein the dimerizing proteins are bonded to each other (e.g., via disulfide bonding) and two polypeptides are arrayed in closed proximity to each other.

Auxiliary domains can be fused to a soluble hybrid FcγR polypeptide to target the polypeptide to specific cells, tissues, or macromolecules (e.g., collagen, or cells expressing other Fc receptors). In some embodiments, an affinity tag (e.g., maltose protein; an immunoglobulin domain; or a polyhistidine tag such as that shown, for example, in SEQ ID NO: 18) is fused to a soluble hybrid FcγR polypeptide to facilitate purification. In some variations, a soluble hybrid FcγR polypeptide is fused to two or more moieties, such as an affinity tag for purification and a targeting domain. Polypeptide fusions can also comprise one or more cleavage sites, particularly between domains. See, e.g., Tuan et al., *Connective Tissue Research* 34:1-9, 1996.

The present invention also provides polynucleotide molecules, including DNA and RNA molecules, that encode the soluble hybrid Fcγ receptor polypeptides disclosed herein. The polynucleotides of the present invention include both single-stranded and double-stranded molecules. Illustrative DNA sequences encoding soluble hybrid Fcγ receptors are disclosed herein. Additional DNA sequences encoding soluble hybrid Fcγ receptors of the present invention can be readily generated by those of ordinary skill in the art based on the genetic code. Counterpart RNA sequences can be generated by substitution of U for T. Those skilled in the art will readily recognize that, in view of the degeneracy of the genetic code, considerable sequence variation is possible among polynucleotide molecules encoding a given polypeptide.

Accordingly, in another aspect, the present invention provides an isolated polynucleotide that encodes a soluble hybrid FcγR polypeptide as described herein. Generally, an isolated polynucleotide of the invention encodes a soluble FcγR polypeptide comprising an amino acid sequence that is at least 70%, at least 80%, at least 90%, at least 95%, at least 96%, at least 97%, at least 98%, or at least 99% or more identical to amino acid residues 35-301, 36-301, or 39-301 of SEQ ID NO:40; amino acid residues 43-310 or 48-310 of SEQ ID NO:42; amino acid residues 18-286, 21-286, or 24-286 of SEQ ID NO:44; or amino acid residues 18-286, 21-286, or 24-286 of SEQ ID NO:46, wherein the encoded polypeptide is capable of specifically binding to the Fc domain of IgG (e.g., human IgG such as, for example, human IgG1). In some embodiments, the encoded polypeptide comprises amino acid residues 35-301, 36-301, or 39-301 of SEQ ID NO:40; amino acid residues 43-310 or 48-310 of SEQ ID NO:42; amino acid residues 18-286, 21-286, or 24-286 of SEQ ID NO:44; or amino acid residues 18-286, 21-286, or 24-286 of SEQ ID NO:46. In other embodiments, the encoded polypeptide comprises an amino acid sequence selected from (i) an amino acid sequence as shown in SEQ ID NO:40 from amino acid x to amino acid 301, wherein x is an integer from 35 to 39, inclusive; (ii) an amino acid sequence as shown in SEQ ID NO:42 from amino acid x to amino acid 310, wherein x is an integer from 43 to 48, inclusive; (iii) an amino acid sequence as shown in SEQ ID NO:44 from amino acid x to amino acid 286, wherein x is an integer from 18 to 24, inclusive; and (iv) an amino acid sequence as shown in SEQ ID NO:46 from amino acid x to amino acid 286, wherein x is an integer from 18 to 24, inclusive. In specific variations, the nucleic acid comprises nucleotide residues 103-903, 106-903, or 115-903 of SEQ ID NO:39; nucleotide residues 127-930 or 142-930 of SEQ ID NO:41; nucleotide residues 52-858, 61-858, or 70-858 of SEQ ID NO:43; or nucleotide residues 52-858, 61-858, or 70-858 of SEQ ID NO:45.

The soluble hybrid Fcγ receptors and nucleic acids of the present invention are preferably recombinant (unless made synthetically). Recombinant DNA methods known in the art and may be readily used to generate an FcγR polypeptide as described herein. As noted above, hybrid receptors in accordance with the present invention are derived from the extracellular domain of human FcγRIA, having the first Ig domain (D1) substituted with the first Ig domain of an Fcγ receptor of a different subclass (e.g., FcγRIIA, FcRIIA, FcγRIIA, or FcγRIIA). Accordingly, recombinant DNA methods may be used, for example, to clone particular nucleic acid segments encoding different polypeptide regions of a hybrid receptor (e.g., one nucleic acid segment encoding the second and third Ig domains of FcγRIA and a second segment encoding the first Ig domain of FcγRIIA, FcγRIIA, FcγRIIA, or FcγRIIA), such as by PCR amplification of the respective nucleic acid regions using RNA or DNA derived from a suitable tissue or cell expressing a native Fcγ receptor. Nucleic acid segments encoding respective regions of a hybrid receptor may then be joined using standard techniques such as, e.g., by ligation or overlap PCR.

DNA or RNA encoding one or more native Fcγ receptors, from which a soluble hybrid FcγR of the present invention may be derived, may be prepared according to methods well known in the art. Complementary DNA (cDNA) clones are prepared from RNA that is isolated from a tissue or cell that produces large amounts of RNA encoding a polypeptide of interest. Total RNA can be prepared using guanidine HCl extraction followed by isolation by centrifugation in a CsCl gradient (Chirgwin et al., *Biochemistry* 18:52-94, 1979). Poly (A)+ RNA is prepared from total RNA using the method of Aviv and Leder (*Proc. Natl. Acad. Sci. USA* 69:1408-1412, 1972). Complementary DNA is prepared from poly(A)+ RNA using known methods. In the alternative, genomic DNA can be isolated. For some applications (e.g., expression in transgenic animals) it may be advantageous to use a genomic clone, or to modify a cDNA clone to include at least one genomic intron. Methods for identifying and isolating cDNA and genomic clones are well known and within the level of ordinary skill in the art, and include the use of the sequences disclosed herein, or parts thereof, for probing or priming a library. Polynucleotides encoding polypeptides of interest are identified and isolated by, for example, hybridization or polymerase chain reaction ("PCR", Mullis, U.S. Pat. No. 4,683,202). Expression libraries can be probed with antibodies to the polypeptide of interest, receptor fragments, or other specific binding partners.

Variants of a specific hybrid Fcγ receptor may also be prepared using known techniques. Variants having one or more amino acid substitutions, deletions, or additions relative to a reference sequence may prepared, for example, by site-specific mutagenesis of nucleotides in the DNA encoding a corresponding hybrid Fcγ receptor protein, using cassette or PCR mutagenesis or another technique well known in the art, to produce DNA encoding the variant, and thereafter expressing the DNA in recombinant cell culture. As outlined above, Fcγ receptor variants in accordance with the present invention typically exhibit similar binding of Fcγ relative to native FcγRIA, although variants can also be selected that have additional variant characteristics. Random mutagenesis may be conducted at a target codon or region and the expressed variant hybrid FcγR protein screened for the optimal combination of desired activity. Techniques for making substitution mutations at predetermined sites in DNA having a known sequence are well-known, for example, M13 primer mutagenesis and PCR mutagenesis.

Amino acid substitutions may be of single amino acid residues or multiple amino acid residues (e.g., 2, 3, 4, or more amino acids can be substituted). Insertions are typically on the order of from about 1 to 20 about amino acids, although considerably larger insertions may be tolerated. Deletions range from about 1 to about 20 residues, or from about 1 to about 30 residues, although in some cases deletions may be much larger. Substitutions, deletions, insertions, or any combination thereof, are used to arrive at a final variant hybrid receptor. In certain variations, modification(s) relative to a reference sequence are done with respect to relatively few amino acids to minimize the alteration of the molecule. Larger changes, however, may be tolerated in certain circumstances.

The polynucleotides of the present invention can also be prepared by automated synthesis. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See generally Glick and Pasternak, *Molecular Biotechnology, Principles & Applications of Recombinant DNA* (ASM Press, Washington, D.C., 1994); Itakura et al., *Ann. Rev. Biochem.* 53: 323-356, 1984; and Climie et al., *Proc. Natl. Acad. Sci. USA* 87:633-637, 1990.

The soluble hybrid Fcγ receptor polypeptides of the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook et al., *Molecular Cloning: A Laboratory Manual* (2nd ed., Cold Spring Harbor Laboratory Press, Cold Spring Harbor, N.Y., 1989); and Ausubel et al., eds., *Current Protocols in Molecular Biology* (Green and Wiley and Sons, NY, 1993).

In general, for expression of a soluble hybrid Fcγ receptor polypeptide, a DNA sequence encoding the polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide fusion into the secretory pathway of a host cell, a secretory signal sequence is provided in the expression vector. The secretory signal sequence may be that of a native Fcγ receptor (e.g., a native FcγRIA, FcγRIIA, FcγRIIB, FcγRIIIA, or FcγRIIB from which the hybrid receptor may be derived), or may be derived from another secreted protein (e.g., t-PA; see U.S. Pat. No. 5,641,655) or synthesized de novo. An engineered cleavage site may be included at the junction between the secretory peptide and the remainder of the polypeptide fusion to optimize proteolytic processing in the host cell. The secretory signal sequence is operably linked to the DNA sequence encoding the polypeptide fusion, i.e., the two sequences are joined in the correct reading frame and positioned to direct the newly synthesized polypeptide fusion into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). Exemplary secretory signal sequences for use in accordance with the present invention include, for example, DNA sequences encoding amino acid residues 1-38 of SEQ ID NO:40, amino acid residues 1-47 of SEQ ID NO:42, amino acid residues 1-17 or 1-20 of SEQ ID NO:44, amino acid residues 1-17 or 1-20 of SEQ ID NO:46, amino acid residues 1-35 of SEQ ID NO:60, amino acid residues 1-16 of SEQ ID NO:62, amino acid residues 1-19 of SEQ ID NO:64, or amino acid residues 1-23 of SEQ ID NO:66.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g., CHO-K$^1$, ATCC No. CCL 61; CHO-DG44, Urlaub et al., *Proc. Natl. Acad. Sci. USA* 77:4216-4220, 1980) cell lines. Additional suitable cell lines are known in the art and available from public depositories such as the American Type Culture Collection, Manassas, Va. Strong transcription promoters can be used, such as promoters from SV-40, cytomegalovirus, or myeloproliferative sarcoma virus. See, e.g., U.S. Pat. No. 4,956,288 and U.S. Patent Application Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, 10801 University Blvd., Manassas, Va. USA under accession numbers 98669, 98668, and PTA-5266, respectively, and derivatives of these vectors.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used. Cell-surface markers and other phenotypic selection markers can be used to facilitate identification of transfected cells (e.g., by fluorescence-activated cell sorting), and include, for example, CD8, CD4, nerve growth factor receptor, green fluorescent protein, and the like.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47-58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press., New York, 1994); and Richardson, Ed., *Baculovirus Expression Protocols, Methods in Molecular Biology* (Humana Press, Totowa, N.J., 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. Using techniques known in the art, a transfer vector encoding a polypeptide fusion is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the polypeptide fusion is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See generally Glick and Pasternak, supra. See also U.S. Pat. No. 5,300,435. Serum-free media are used to grow and maintain the cells. Suitable media formulations are known in the art and can be obtained from commercial suppliers. The cells are grown up from an inoculation density of approximately 2–5×105 cells to a density of 1–2×10$^6$ cells, at which time a recombinant viral stock is added at a multiplicity of infection (MOI) of 0.1 to 10, more typically near 3. Procedures used are generally described in available laboratory manuals (e.g., King and Possee, supra; O'Reilly et al., supra; Richardson, supra).

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansemdla polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, e.g., Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus*, and other genera are also useful host cells within the present invention. Techniques for transforming these hosts and expressing foreign DNA sequences cloned therein are well known in the art (see, e.g., Sambrook et al., supra). When expressing a polypeptide fusion in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine HCl or urea. The denatured polypeptide can then be refolded by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) and recovering the protein, thereby obviating the need for denaturation and refolding. See, e.g., Lu et al., *J. Immunol. Meth.* 267:213-226, 2002.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Proteins of the present invention are purified by conventional protein purification methods, typically by a combination of chromatographic techniques. See generally *Affinity Chromatography: Principles & Methods* (Pharmacia LKB Biotechnology, Uppsala, Sweden, 1988); and Scopes, *Protein Purification: Principles and Practice* (Springer-Verlag, New York, 1994). Proteins comprising an immunoglobulin heavy chain polypeptide can be purified by affinity chromatography on immobilized protein A. Additional purification steps, such as gel filtration, can be used to obtain the desired level of purity or to provide for desalting, buffer exchange, and the like.

The polypeptides of the present invention can be purified to at least about 80% purity, to at least about 90% purity, to at least about 95% purity, or greater than 95%, such as 96%, 97%, 98%, or greater than 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support See, for example, *Affinity Chromatography: Principles & Methods* (Pharmacia LKB Biotechnology 1988), and Doonan, *Protein Purification Protocols* (The Humana Press 1996).

Additional variations of soluble FcγR isolation and purification can be devised by those of skill in the art. For example, anti-FcγR antibodies can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher (ed), *Meth. Enzymol.* 182:529, 1990). Within additional embodiments of the invention, a fusion of the polypeptide of interest and an affinity tag (e.g., maltose-binding protein, an immunoglobulin domain, substance P, Flag™ peptide, or another polypeptide or protein for which an antibody or other specific binding agent is available) may be constructed to facilitate purification.

Soluble hybrid FcγR polypeptides or fragments thereof may also be prepared through chemical synthesis, as described above. The FcγR polypeptides may be monomers or multimers (e.g., homodimers); glycosylated or non-glycosylated; PEGylated or non-PEGylated; and may or may not include an initial methionine amino acid residue.

In some variations, a soluble hybrid FcγR polypeptide is chemically modified via linkage to a polymer. Typically, the polymer is water soluble so that the hybrid FcγR polypeptide conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. The polymer may be branched or unbranched. A hybrid FcγR polypeptide conjugate can also comprise a mixture of such water-soluble polymers. General methods for producing conjugates comprising a polypeptide and water-soluble polymer moieties are known in the art. (See, e.g., U.S. Pat. No. 5,382,657 to Karasiewicz et al.; U.S. Pat. No. 5,738,846 to Greenwald et al.; Nieforth et al., *Clin. Pharmacol. Ther.* 59:636, 1996; Monkarsh et al., *Anal. Biochem.* 247:434, 1997.) Such methods can be employed for making hybrid FcIR-comprising homodimeric, heterodimeric or multimeric soluble receptor conjugates.

One example of a soluble hybrid FcγR polypeptide conjugate comprises a polyalkyl oxide moiety attached to the N-terminus of the FcγR polypeptide. PEG is one suitable polyalkyl oxide. As an illustration, soluble hybrid FcγR can be modified with PEG, a process known as "PEGylation." PEGylation of soluble hybrid FcγR can be carried out by any of the PEGylation reactions known in the art. (See, e.g., EP 0 154 316; Delgado et al., *Critical Reviews in Therapeutic Drug Carrier Systems* 9:249, 1992; Duncan and Spreafico, *Clin. Pharmacokinet.* 27.290, 1994; Francis et al., *Int J Hematol* 68:1, 1998.) For example, PEGylation can be performed by an acylation reaction or by an alkylation reaction with a reactive polyethylene glycol molecule. In an alternative approach, hybrid FcγR conjugates are formed by condensing activated PEG, in which a terminal hydroxy or amino group of PEG has been replaced by an activated linker. (See, e.g., U.S. Pat. No. 5,382,657 to Karasiewicz et al.) For PEGylation reactions, the typical molecular weight of a polymer molecule is about 2 kDa to about 100 kDa, about 5 kDa to about 50 kDa, or about 12 kDa to about 25 kDa. The molar ratio of water-soluble polymer to soluble hybrid FcγR will generally be in the range of 1:1 to 100:1. Typically, the molar ratio of water-soluble polymer to soluble hybrid FcγR will be 1:1 to 20:1 for polyPEGylation, and 1:1 to 5:1 for monoPEGylation.

III. Methods and Compositions for Using Soluble Hybrid Fcγ Receptors

The soluble hybrid FcγR polypeptides of the present invention act specifically against IgG and can inhibit IgG binding to an Fcγ receptor, and are thus useful for inhibiting IgG and Fcγ receptor activity. Accordingly, in another aspect of the invention, soluble hybrid FcγR polypeptides as described herein are used to inhibit the interaction between IgG and Fc receptors as well as to inhibit physiological correlates of such IgG-FcR interactions in vivo or in vitro (e.g., the precipitation of antigen-antibody immune complexes, signal transduction, cytokine secretion from immune cells having cell-surface Fc receptors). Activity of the soluble FcγR polypeptides of the present invention can be assayed, for example, in proliferation, luciferase, or binding assays in the presence of IgG, as well as other biological or biochemical assays for assessing the interaction of IgG with FcγR as described herein or otherwise known in the art.

As shown herein, a soluble FcγRIA polypeptide completely blocked immune complex precipitation and also blocked the binding and signaling of immune complexes (described in detail in the Examples below). Moreover, soluble FcγRIA blocked inflammation in the cutaneous Arthus reaction as well as in the collagen antibody-induced and collagen-induced models of arthritis. These findings show that soluble FcγRIA is a potent therapeutic that can be used to treat autoimmune disease and inflammation and further support the use of other soluble, high-affinity receptors for Fcγ, including the hybrid Fcγ receptors as described herein, for treating such conditions.

The soluble hybrid FcγR polypeptides of the invention are, therefore, particularly useful for modulating an immune response by binding IgG and inhibiting the binding of IgG with an endogenous Fcγ receptor. Accordingly, the present invention includes the use of soluble hybrid FcγR polypeptides to treat a subject with inflammation or having an immune disease or disorder. Suitable subjects include mammals, such as humans. The soluble hybrid FcγR polypeptides of the invention may be used for inhibiting the inflammatory effects of IgG and/or immune complexes in vivo, for therapeutic use against SLE, cryoglobulinemia, autoimmune thrombocytopenias (ITP and TTP), adult dermatomyositis, hepatitis-C-associated cryoglobulinemia, hepatitis-B-associated polyarteritis nodosa, Guillian-Barre syndrome, Goodpasture's syndrome, chronic inflammatory demyelinating polyneuropathies, anti-phospholipid antibody syndrome, vasculitis, uveitis, serum sickness, pemphigus (e.g., pemphigus vulgaris), diseases associated with exogenous antigens, psoriasis, atopic dermatitis, inflammatory skin conditions, endotoxemia, arthritis, asthma, IBD, colitis, psoriatic arthritis, rheumatoid arthritis, or other IgG- or immune-complex-mediated inflammatory conditions.

In certain variations, a soluble hybrid FcγR polypeptide is used to treat an IgG-mediated inflammatory condition such as, for example, systemic lupus erythematosus (SLE); lupus (including nephritis, non-renal, discoid, alopecia); cryoglobulinemia; mixed connective tissue disease; autoimmune thrombocytopenias (idiopathic thrombocytopenic purpura (ITP); thrombotic throbocytopenic purpura (TTP)); Sjogren's syndrome; adult dermatomyositis; hepatitis-C-associated cryoglobulinemia; hepatitis-B-associated polyarteritis nodosa; Guillian-Barre syndrome; Goodpasture's syndrome; chronic inflammatory demyelinating polyneuropathies; anti-phospholipid antibody syndrome; vasculitis; uveitis; serum sickness; diseases associated with exogenous antigens; arthritis (rheumatoid arthritis, juvenile rheumatoid arthritis, psoriatic arthritis); psoriasis; atopic dermatitis; inflammatory skin conditions; responses associated with inflammatory bowel disease (IBD) (Crohn's disease, ulcerative colitis); diverticulosis; asthma; pancreatitis; type I (juvenile onset) diabetes (IDDM); pancreatic cancer; pancreatitis; Grave's Disease; chronic autoimmune urticaria; polymyositis/dermatomyositis; toxic epidermal necrolysis; systemic scleroderma and sclerosis; respiratory distress syndrome; adult respiratory distress syndrome (ARDS); meningitis; allergic rhinitis; encephalitis; colitis; glomerulonephritis; an IgG-mediated allergic condition; atherosclerosis, autoimmune myocarditis; multiple sclerosis; allergic encephalomyelitis; sarcoidosis, granulomatosis including Wegener's granulomatosis; agranulocytosis; aplastic anemia; Coombs positive anemia; Diamond Blackfan anemia; immune hemolytic anemia including autoimmune hemolytic anemia (AMHA); pernicious anemia; pure red cell aplasia (PRCA); Factor VIII deficiency; hemophilia A; autoimmune neutropenia; pancytopenia; leucopenia; diseases involving leukocyte diapedesis; a CNS inflammatory disorder, multiple organ injury syndrome; myasthenia gravis; anti-glomerular basement membrane disease; Bechet disease; Castleman's syndrome; Lambert-Eaton Myasthenic Syndrome; Reynaud's syndrome; Stevens-Johnson syndrome; bone marrow transplant rejection; solid organ transplant rejection (including pretreatment for high panel reactive antibody titers); graft-versus-host disease (GVHD); pemphigoid bullous; pemphigus (all including vulgaris, foliaceus); autoimmune polyendocrinopathies; Reiter's disease; stiff-man syndrome; immune complex nephritis; an autoimmune disease of the testis or ovary such as, e.g., autoimmune orchitis or oophoritis; primary hypothyroidism; an autoimmune endocrine disease such as, e.g., autoimmune thyroiditis, chronic thyroiditis (Hashimoto's Thyroiditis), subacute thyroiditis, idiopathic hypothyroidism, Addison's disease, or an autoimmune polyglandular syndrome (or a polyglandular endocrinopathy syndrome); autoimmune hepatitis; Lymphoid interstitial pneumonitis (HIV); bronchiolitis obliterans (non-transplant) vs NSIP, large vessel vasculitis (including polymyalgia rheumatica and giant cell (Takayasu's) arteritis); medium vessel vasculitis (including Kawasaki's Disease and polyarteritis nodosa); ankylosing spondylitis; rapidly progressive glomerulonephritis; primary biliary cirrhosis; celiac sprue (gluten enteropathy); ALS; coronary artery disease; or another instance where inhibition of IgG or immune complexes is desired.

The soluble hybrid FcγR polypeptides of the invention may also be used to treat psychological disorders associated with deposition of immune complexes with the choroids plexus of the brain. Such deposition, for example, may underlie the central and peripheral nervous system manisfestations of diseases such as Systemic Lupus Erythematosus. In some patients, these manisfestations are a major cause of morbidity and mortality and include cognitive dysfunction, particularly difficulties with memory and reasoning psychosis, headaches, and seizures. As another example, deposition of immune complexes within the choriod plexus may be responsible for the peripheral neuropathy seen in essential mixed cryoglobulinemia. (See *Harrison's Principles of Internal Medicine* (Kasper et al. eds., McGraw-Hill, New York 2005).)

In each of the embodiments of the treatment methods described herein, a soluble hybrid FcγR polypeptide is delivered in a manner consistent with conventional methodologies associated with management of the disease or disorder for which treatment is sought. In accordance with the disclosure herein, an effective amount of the agent is administered to a subject in need of such treatment for a time and under conditions sufficient to prevent or treat the disease or disorder.

Subjects for administration of soluble hybrid FcγR polypeptides as described herein include patients at high risk for developing a particular IgG-mediated inflammatory condition as well as patients presenting with an existing IgG-mediated inflammatory condition. In certain embodiments, the subject has been diagnosed as having the disease or disorder for which treatment is sought. Further, subjects can be monitored during the course of treatment for any change in the disease or disorder (e.g., for an increase or decrease in clinical symptoms of the disease or disorder). Also, in some variations, the subject does not suffer from another disease or disorder requiring treatment that involves inhibiting the interaction of IgG with an Fcy receptor.

In prophylactic applications, pharmaceutical compositions or medicants are administered to a patient susceptible to, or otherwise at risk of, a particular disease in an amount sufficient to eliminate or reduce the risk or delay the outset of the disease. In therapeutic applications, compositions or medicants are administered to a patient suspected of, or already suffering from such a disease in an amount sufficient to cure, or at least partially arrest, the symptoms of the disease and its complications. An amount adequate to accomplish this is referred to as a therapeutically- or pharmaceutically-effective dose or amount. In both prophylactic and therapeutic regimes, a soluble hybrid FcγR polypeptide of the invention is usually administered in several dosages until a sufficient response (e.g., inhibition of inflammatory mediators associated with the interaction of IgG with FcγR or with IC deposition) has been achieved. Typically, the response is monitored and repeated dosages are given if the desired response starts to fade.

To identify subject patients for treatment according to the methods of the invention, accepted screening methods may be employed to determine risk factors associated with specific IgG-mediated inflammatory conditions or to determine the status of an existing disorder identified in a subject. Such methods can include, for example, determining whether an individual has relatives who have been diagnosed with a particular disease. Screening methods can also include, for example, conventional work-ups to determine familial status for a particular disease known to have a heritable component Toward this end, nucleotide probes can be routinely employed to identify individuals carrying genetic markers associated with a particular disease of interest. In addition, a wide variety of immunological methods are known in the art that are useful to identify markers for specific diseases. For example, various ELISA immunoassay methods are available and well-known in the art that employ monoclonal antibody probes to detect antigens or autoantibodies associated with specific inflammatory diseases. Screening may be implemented as indicated by known patient symptomology, age factors, related risk factors, etc. These methods allow the clinician to routinely select patients in need of the methods described herein for treatment. In accordance with these methods, inhibition of IgG-mediated inflammation may be implemented as an independent treatment program or as a follow-up, adjunct, or coordinate treatment regimen to other treatments.

For administration, a soluble hybrid FcγR polypeptide is formulated as a pharmaceutical composition. A pharmaceutical composition comprising a soluble hybrid FcγR polypeptide can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Pharmaceutically acceptable carriers can be aqueous, lipidic, semi-solid or solid as appropriate to the condition to be treated and mode of delivery. Pharmaceutically acceptable aqueous carriers include, without limitation, saline, buffered saline (e.g., phosphate-buffered saline), 5% dextrose in water, and the like. Other suitable carriers are well-known to those in the art (See, e.g., Gemnnaro (ed.), *Remington's Pharmaceutical Sciences* (Mack Publishing Company, 19th ed. 1995).) Formulations may further include one or more excipients, preservatives, solubilizers, buffering agents, albumin to prevent protein loss on vial surfaces, etc.

A pharmaceutical composition comprising a soluble hybrid FcγR polypeptide of the invention is administered to a subject in an effective amount. Accordingly, the composition is generally administered in an amount that produces a statistically significant beneficial effect, such as a statistically significant moderation or reversal of the progression or severity of a disease. The exact dose will be determined by the clinician according to accepted standards, taking into account the nature and severity of the condition to be treated, patient traits, etc. Determination of dose is within the level of ordinary skill in the art. According to the methods of the present invention, the polypeptide may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, depending on the route and method of administration, the soluble hybrid FcγR polypeptide may be administered to a subject in a single bolus delivery, via continuous delivery over an extended time period (e.g., continuous transdermal delivery or as a prolonged infusion), or in a repeated administration protocol (e.g., on an hourly, daily, or weekly basis). Intravenous administration will be by bolus injection or infusion over a typical period of one to several hours. Sustained release formulations can be employed.

Determination of effective dosages is typically based on animal model studies followed up by human clinical trials and is guided by determining effective dosages and administration protocols that significantly reduce the occurrence or severity of the subject disease or disorder in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically or prophylactically effective amount is also one in which any undesired collateral effects are outweighed by beneficial effects of inhibition IgG-mediated inflammation. For administration of a soluble hybrid FcγR polypeptide, a dosage typically ranges from about 0.1 µg to 100 mg/kg or 1 µg/kg to about 50 mg/kg, and more usually 10 µg to 5 mg/kg of the subject's body weight. In more specific embodiments, an effective amount of the agent is between about 1 µg/kg and about 20 mg/kg, between about 10 µg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring of IgG-mediated inflammation and/or clinical symptoms of the disease or disorder.

Dosage of the pharmaceutical composition may be varied by the attending clinician to maintain a desired concentration at a target site. For example, if an intravenous mode of delivery is selected, local concentration of the agent in the bloodstream at the target tissue may be between about 1-50 nanomoles of the composition per liter, sometimes between about 1.0 nanomole per liter and 10, 15, or 25 nanomoles per liter depending on the subject's status and projected measured response. Higher or lower concentrations may be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar.

A pharmaceutical composition comprising a soluble hybrid FcγR polypeptide can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants. (See, e.g., Bremer et al., *Pharm. Biotechnol.* 10:239, 1997; Ranade, "Implants in Drug Delivery," in *Drug Delivery Systems* 95-123 (Ranade and Hollinger, eds., CRC Press 1995); Bremer et al., "Protein Delivery with Infusion Pumps," in *Protein belivery: Physical Systems* 239-254 (Sanders and Hendren, eds., Plenum Press 1997); Yewey et al., "Delivery of Proteins from a Controlled Release Injectable Implant," in *Protein Delivery: Physical Systems* 93-117 (Sanders and Hendren, eds., Plenum Press 1997).) Other solid forms include creams, pastes, other topological applications, and the like.

Liposomes provide one means to deliver therapeutic polypeptides to a subject, e.g., intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments. (See, generally, Bakker-Woudenberg et al., *Eur. J. Clin. Microbiol. Infect. Dis.* 12 (Suppl. 1):S61, 1993; Kim, *Drugs* 46:618, 1993; Ranade, "Site-Specific Drug Delivery Using Liposomes as Carriers," in *Drug Delivery Systems* 3-24 (Ranade and Hollinger, eds., CRC Press 1995).) Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s). (See, e.g., Machy et al., *Liposomes In Cell Biology And Pharmacology* (John Libbey 1987); Ostro et al., *American J. Hosp. Pharm.* 46:1576, 1989.) Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (see Scherphof et al., *Ann. N.Y. Acad. Sci.* 446:368, 1985). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (see Claassen et al., *Biochim. Biophys. Acta* 802:428, 1984). In addition, incorporation of glycolipid- or polyethelene glycol-derivatized phospholipids into liposome membranes has been shown to result in a significantly reduced uptake by the reticuloendothelial system (see Allen et al., *Biochim. Biophys. Acta* 1068:133, 1991; Allen et al., *Biochim. Biophys. Acta* 1150:9, 1993).

Liposomes can also be prepared to target particular cells or organs by varying phospholipid composition or by inserting receptors or counter-receptors into the liposomes. For example, liposomes, prepared with a high content of a nonionic surfactant, have been used to target the liver. (See, e.g., Japanese Patent 04-244,018 to Hayakawa et al.; Kato et al., *Biol. Pharm. Bull.* 16:960, 1993.) These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver. (See Shimizu et al., *Biol. Pharm. Bull.* 20:881, 1997.)

Alternatively, various targeting counter-receptors can be bound to the surface of the liposome, such as antibodies, antibody fragments, carbohydrates, vitamins, and transport proteins. For example, for targeting to the liver, liposomes can be modified with branched type galactosyllipid derivatives to target asialoglycoprotein (galactose) receptors, which are exclusively expressed on the surface of liver cells. (See Kato and Sugiyama, *Crit. Rev. Ther. Drug Carrier Syst.* 14:287, 1997; Murahashi et al., *Biol. Pharm. Bull.* 20:259, 1997.) In a more general approach to tissue targeting, target cells are prelabeled with biotinylated antibodies specific for a counter-receptor expressed by the target cell. (See Harasym et al., *Adv. Drug Deliv. Rev.* 32:99, 1998.) After plasma elimination of free antibody, streptavidin-conjugated liposomes are administered. In another approach, targeting antibodies are directly attached to liposomes. (See Harasym et al., supra.)

Polypeptides of the present invention can be encapsulated within liposomes using standard techniques of protein microencapsulation. (See, e.g., Anderson et al., *Infect. Immun.* 31:1099, 1981; Anderson et al., *Cancer Res.* 50:1853, 1990; Cohen et al., *Biochim. Biophys. Acta* 1063: 95, 1991; Alving et al. "Preparation and Use of Liposomes in Immunological Studies," in *Liposome Technology* (Vol. III) 317 (Gregoriadis, ed., CRC Press, 2nd ed. 1993); Wassef et al., *Meth. Enzymol.* 149:124, 1987.) As noted above, therapeutically useful liposomes may contain a variety of components. For example, liposomes may comprise lipid derivatives of poly(ethylene glycol). (See Allen et al., *Biochim. Biophys. Acta* 1150:9, 1993.)

Degradable polymer micro spheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer. (See, e.g., Gombotz and Pettit, Bioconjugate Chem. 6:332, 1995; Ranade, "Role of Polymers in Drug Delivery," in *Drug Delivery Systems* 51-93 (Ranade and Hollinger, eds., CRC Press 1995); Roskos and Maskiewicz, "Degradable Controlled Release Systems Useful for Protein Delivery," in *Protein Delivery: Physical Systems* 45-92 (Sanders and Hendren, eds., Plenum Press 1997); Bartus et al., *Science* 281:1161, 1998; Putney and Burke, *Nature Biotechnology* 16:153, 1998; Putney, *Curr. Opin. Chem. Biol.* 2:548, 1998.) Polyethylene glycol (PEG)-coated nanospheres can also provide carriers for intravenous administration of therapeutic proteins. (See. e.g., Gref et al., *Pharm. Biotechnol.* 10:167, 1997.)

Other dosage forms can be devised by those skilled in the art, as shown by, e.g., Ansel and Popovich, *Pharmaceutical Dosage Forms and Drug Delivery Systems* (Lea & Febiger, 5th ed. 1990); Gennaro (ed.), *Remington's Pharmaceutical Sciences* (Mack Publishing Company, 19th ed. 1995), and Ranade and Hollinger, *Drug Delivery Systems* (CRC Press 1996).

Pharmaceutical compositions may be supplied as a kit comprising a container that comprises a soluble FcγR polypeptide of the invention. The FcγR polypeptides of the invention can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the soluble hybrid FcγR polypeptide-comprising composition is contraindicated in patients with a known hypersensitivity to FcγR.

As discussed above, the soluble hybrid FcγR polypeptides of the invention have therapeutic potential for a wide variety of IgG-mediated inflammatory diseases. Inflammation—a protective response by an organism to fend off an invading agent—is a cascading event that involves many cellular and humoral mediators. On one hand, suppression of inflammatory responses can leave a host immunocompromised; if left unchecked, however, inflammation can lead to serious complications including, for example, chronic inflammatory diseases. Importantly, these diverse disease states share common inflammatory mediators. The collective diseases that are characterized by inflammation have a large impact on human morbidity and mortality. The studies described herein show, inter alia, the ability of soluble FcγR to block the binding and signaling of immune complexes, as well as the ability of soluble FcγR to treat IgG-mediated disease. Thus, the soluble hybrid FcγR polypeptides of the invention have therapeutic potential for a vast number of human and animal diseases such as, for example, the IgG- and immune-complex-mediated diseases discussed herein. Exemplary diseases amenable to treatment using soluble hybrid FcγR are further described in Sections III(A) and III(B), infra.

A. Immune-complex-Mediated Diseases

The binding of an antigen with its cognate antibody generates immune complexes, and deposition of these immune complexes within tissues is the pathogenic mechanism underlying a variety of autoimmune diseases (see Jancar and Crespo, *Trends Immunol.* 26:48-55, 2005). These diseases include the connective tissue autoimmune diseases such as systemic lupus erythematosus (SLE), dermatomyositis, rheumatoid arthritis, Sjogren's syndrome, and mixed connective tissue disease; diseases of diverse etiology such as cryoglobulinemia, polyarteritis nodosa, and the antiphospholipid syndrome; as well as diseases associated with exogenous antigens including bacterial, viral, and parasitic infections, diseases associated with organic dusts, and serum sickness type of diseases including passive immunotherapy for infection, venomous snake bites, and drug hypersensitivity. While each of these conditions is caused by and exhibits specific antigen-antibody pairs, the mechanism for tissue damage is similar: the formation of circulating immune complexes, followed by their deposition within tissues (see Jancar and Crespo, supra). Antigen-antibody complexes can damage tissues by triggering inflammation, a process mediated in part through the binding of immune complexes to cell surface Fcγ receptors and by their ability to fix complement.

In the normal situation, immune complexes are cleared by phagocytic cells of the reticuloendothelial system. In some instances, however, immune complexes accumulate and deposit in tissues, causing type III hypersensitivity reactions. (See Jancar and Crespo, supra.) When immune complexes form in the blood, deposition can occur at sites removed from the site of antigen entry. Complex deposition is routinely observed, e.g., on blood vessel walls, in the synovial membranes of joints, on the glomerular basement membrane of the kidney, and on the choroid plexus of the brain, sites where filtration of plasma occurs. (See Jancar and Crespo, supra.) This is the reason for the high incidence of arthritis, vasculitis, and glomerulonephritis observed in immune complex-mediated diseases, such as cryoglobulinemia.

Following their deposition within tissues, immune complexes bind to cell surface FcγR via the Fc domain of IgG. As previously noted, FcγR play a crucial role as a link between the humoral and cellular arms of the immune system (see Coben-Solal et al., *Immunol. Lett.* 92:199-205, 2004; Hogarth et al., *Curr. Opin. Immunol.* 14:798-802, 2002; Nakamura et al., *Expert Opin. Ther. Targets* 9:169-190, 2005; Nimmerjahn, *Springer Semin. Immunopathol.* 28:305-319, 2006). Ligation of these cell surface receptors by the Fc portion of IgG can trigger a variety of immune effector functions such as antigen presentation, antibody dependent cellular cytotoxicity (ADCC), phagocytosis, and the release of inflammatory mediators. The three main classes of Fcγ receptors—FcγRI, FcγRII, and FcRγIII—are expressed within specific and overlapping subsets of cells of the human immune system, expression patterns that account for their diverse roles in immune homeostasis (see Nakamura et al., supra). With the exception of FcγRI, which exhibits a high affinity for monomeric IgG, the other subclasses of FcγRs are low affinity IgG receptors. (See Cohen-Solal et al., supra; Hogarth et al., supra.) However, these cellular receptors bind antigen-antibody immune complexes (IC) with high avidity, through multiple Fc:FcγR interactions. This property is thought to allow cells expressing FcγRII and/or FcγRIII to sample their extracellular environment and respond appropriately to IC in the face of saturating amounts of monomeric IgG. (See Hogarth et al., supra.)

As part of a screening effort to identify soluble receptors demonstrating this ability, the soluble extracellular domains of each of the human native FcγR were expressed in CHO cells and purified to homogeneity from their conditioned media. While each of the rh-FcγR reduced immune complex-mediated inflammatory events in several in vitro systems, only the high affinity receptor, FcγRIA, produced consistent reductions in inflammation in the cutaneous reverse passive Arthus reaction in mice. This result was unexpected in that FcγRIA, as a high affinity receptor for monomeric IgG, was generally expected to be saturated with circulating monomeric IgG in vivo and thus unavailable for binding to IC. The observation that systemic delivery of FcγRIA also abolished inflammation in the murine collagen antibody-induced model of arthritis suggests that FcγRIA may be a novel therapy for treating immune complex-mediated diseases. Further, these results support the use of other soluble, high-affinity receptors for Fcγ, including the hybrid Fcγ receptors as described herein, for treating such conditions.

Accordingly, by blocking the binding of immune complexes to cell surface Fc gamma receptors, the soluble hybrid FcγR polypeptides of the invention can reduce inflammatory cytokine secretion and reduce infiltration of inflammatory cell types such as neutrophils. As demonstrated by studies described herein, soluble FcγRIA blocked the precipitation of antigen antibody immune complexes and inhibited immune complex-mediated cytokine secretion by mast cells (see Examples 9 and 10, infra). In studies in mice, moreover, soluble FcγRIA reduced edema and neutrophil infiltration in the cutaneous reverse passive Arthus reaction and reduced paw inflammation in the collagen antibody-induced arthritis model and, moreover, in collagen-induced arthritis in mice. (See Examples 9-11 and 13, infra.) Thus, soluble FcγRIA, as well as hybrid forms thereof as described herein, can be used in the treatment of various immune complex-mediated diseases in humans or other non-human species.

1. Cryoblobulinemia

The term cryoglobulinemia refers to the presence in serum of one (monoclonal cryoglobulinemia) or more (mixed cryoglobulinemia) immunoglobulins that reversibly precipitate at temperatures below 37° C. (See Meltzer and Franklin, *Am. J. Med.* 40:828-836, 1996; Dammacco et al., *Eur. J. Clin. Invest.* 31:628-638, 2001; Sansonno et al., *Rheumatology (Oxford)* 46:572-578, 2007). The mechanism of cryoprecipitation is obscure but may involve alterations in Ig structure, self-association of Ig Fc domains, and/or IgM rheumatoid factor activity. (See Sansonno and Dammacco,

*Lancet Infect. Dis.* 5:227-236, 2005.) Cryoglobulinemia is classified into three subgroups (see Dammacco et al., supra): Type I is composed of a single monoclonal Ig; Type II is composed of a mixture of monoclonal IgM and polyclonal IgG; and Type III is a mixture of polyclonal IgM/IgG. Cryoglobulinemia types I, II, and III account for approximately 10-15%, 50-60%, and 30-40%, of all people with serum cryoprecipitates, respectively. (See Dammacco et al., supra; Sansonno et al., supra.)

Patients with cryogobulinemia present most often with a clinical triad of purpura, weakness, and arthralgias, as well as glomerulonephritis, vasculitis, peripheral neuropathy, arthritis, and/or pulmonary symptoms of hemoptysis and dyspnea. (See Dammacco et al., supra; Sansonno et al., supra; Ferri et al., *Cleve. Clin. J. Med.* 69 Suppl 2:SII20-23, 2002 ("Ferri et al. I"); Ferri et al, *J. Clin. Pathol.* 55:4-13, 2002 ("Ferri et al. II").) Cryoglobulinemia can be observed in association of a variety of disorders including multiple myeloma, lymphoproliferative disorders, connective tissue diseases, infection, and liver disease. (Ferri et al. I, supra; Ferri et al. II, supra.) Before the discovery of hepatitis C virus (HCV) and prior to development of methods to detect anti-HCV antibodies, patients without identifiable underlying disease were considered to have idiopathic or "essential" mixed cryoglobulinemia. It is now known that "essential" mixed cryoglobulinemia is strongly associated with HCV infection and encompasses the majority of patients with types II and III cryoglobulinemia. (See Sansonno et al., supra.) Current evidence suggests that essential mixed cryoglobulinemia occurs when an aberrant immune response to hepatitis C infection leads to the formation of immune complexes consisting of hepatitis C antigens, polyclonal hepatitis C-specific IgG, and monoclonal IgM rheumatoid factor. The deposition of these immune complexes within susceptible tissue sites triggers an inflammatory cascade that results in the clinical syndrome of essential mixed cryoglobulinemia. (Dammacco et al., supra; Sansonno et al., supra.)

Cryoglobulinemia is also associated with a variety of other infections in addition to HCV (see Ferri et al. II, supra), including those of viral origin such as cytomegalovirus (CMV), Epstein-Barr virus (EBV), human immunodeficiency virus (HIV-1), and hepatis B virus (HBV), those of bacterial origin including *Mycoplasma pneuymoniae, Treponema pallidum* (syphilis), *Mycobacterium tuberculosis, Coxiella Burnetti* Q fever, *Brucella*, and infections with parasites such as *Toxoplasma gondii* and *Visceral leishmaniasis.*

Essential mixed cryoglobulinemia is considered to be a primary vasculitis disorder. The Chapel Hill Consensus Conference (CHCC) classification of vasculitis is based on the size of the affected vessels and groups the diseases into those affecting large-, medium-, or small-vessels. (See Jennette et al., *Cleve. Clin. J. Med.* 69 Suppl 2:SII33-38, 2002; Fiorentino, *J. Am. Acad. Dermatol.* 48:311-340, 2003.) Importantly, two vasculitis syndromes are associated with deposition of immune complexes: Henoch-Schonlein purpura is associated with deposition of IgA-containing immune complexes; and essential cryoglobulinemic vasculitis is associated with deposition of IgG/IgM immune complexes. (See Fiorentino, supra.)

The incidence of HCV infection in essential mixed cryoglobulinemia ranges from 40-100% in reported cases, depending on geography. Approximately 200 million worldwide are chronically infected with HCV, with 3.5 million new infections reported each year. (See Sy and Jamal, *Int J. Med. Sci.* 3:41-46, 2006.) The USA incidence and prevalence are 30,000 new infections per year and 3.9 million with chronic infections. (See Sy and Jamal, supra.) Approximately 50-60% of patients with chronic HCV infections have cryoglobulins in their serum and overt cryoglobulinemic syndromes develop in about 5% of cases. (See Sansonno et al., supra; Sansonno and Dammacco, supra.) Hepatitis B virus has been described as an etiologic agent in 5% of patients with mixed cryoglobulinemia. (See Ferri et al. I, supra.)

The current therapies for cryoglobulinemia include low dose steroids for moderate disease and combinations of steroids, cyclophosphamide, or plasmapheresis are used for more severe forms of disease. Patients with active HCV-mediated hepatitis are often treated with a combination of interferon-α and ribavirin.

The efficacy of the FcγRIA polypeptides of the invention can be tested in vivo in animal models of disease. A particularly suitable animal model for evaluating efficacy of soluble FcγRIA against immune complex-mediated disease, including cryoglobulinemia, are mice over-expressing thymic stromal lymphopoietin (TSLP), an interleukin-7 (IL-7)-like cytokine with B-cell promoting properties. TSLP mice produce large amounts of circulating cryoglobulins of mixed IgG-IgM composition. (See Taneda et al., *Am. J. Pathol.* 159:2355-2369, 2001.) Development of mixed cryoglobulinemia in these animals is associated with systemic inflammatory disease involving kidneys, liver, lungs, spleen, and skin (see Taneda et al., supra) due to immune complex deposition in these tissues. Kidney disease in these animals closely resembles human cryoglobulinemia glomerulonephritis as seen in patients with HCV infection. A role for Fcγ receptors in the disease process was shown by the exacerbation of renal injury with accelerated morbidity and mortality after deletion of the inhibitory receptor Fcγ receptor IIb. (See Muhlfeld et al., *Am. J. Pathol.* 163:1127-1136, 2003.) Treatment of TSLP-transgenic mice with recombinant soluble FcγR in accordance with the present invention is further described in Example 12, infra.

2. Systemic Lupus Erythematosus

Systemic lupus erythematosus (SLE) is a complex, multi-organ (systemic) autoimmune disorder characterized by the production of pathogenic autoantibodies with subsequent deposition of immune complexes, which results in widespread tissue damage. Although the etiology of SLE is unknown, multiple genetic, environmental, and hormonal factors are thought to play a role in disease. (See Hahn, "Systemic Lupus Erythematosus" in *Harrison's Principles of Internal Medicine* (Kasper et al. eds., McGraw-Hill, New York 2005).) SLE is clinically characterized by a waxing and waning course and by involvement of multiple organs including skin, kidneys, and central nervous system (*Lupus: Molecular and Cellular Pathogenesis* (Kammer and Tsokos eds., Human Press, N.J., 1st ed. 1999); Systemic Lupus Erythromatosus (Lahita ed., Academic Press, Amsterdam, 3rd ed. 1999)). Thus, the disease displays a broad variety of symptoms and clinical features, including systemic, cutaneous, renal, musculoskeletal, and hematologic.

The overall prevalence of SLE is about one in 2000, and about one in 700 Caucasian women develops SLE during her life time. (Lahita, *Curr. Opin. Rheumatol.* 11:352-6, 1999). In the United States alone, over half a million people have SLE, and most are women in their childbearing years (Hardin, *J. Exp. Med.* 185:1101-1111, 2003).

There is no single criteria to diagnose SLE. The American College of Rheumatology has developed 11 criteria to diagnose SLE, which span the clinical spectrum of SLE in aspects of skin, systemic, and laboratory tests. These criteria include malar rash, discoid rash, sensitivity to sun light, oral ulcers, arthritis, serositis, kidney and central nervous system inflammation, blood alterations, and the presence of anti-nuclear antibodies. A patient must meet four of these criteria in order to be classified as a SLE patient. (Tan et al., *Arthritis Rheumatol.* 25:1271-1277, 1982). SLE is usually confirmed by tests including, but not limited to, blood tests to detect anti-nuclear antibodies; blood and urine tests to assess kidney function; complement tests to detect the presence of low levels of complement that are often associated with SLE; a sedimentation rate (ESR) or C-reactive protein (CRP) to measure inflammation levels; X-rays to assess lung damage and EKGs to assess heart damage.

The standard therapy for SLE is administration of the steroid glucocorticoid, a general immune response inhibitor. It can be used to relieve symptoms; however, no cure for SLE is currently available. Low dose p.o. prednisone at a level less than 0.5 mg/kg/day is usually given. Unfortunately, this therapy is insufficient to keep patients in remission, and flaring of the disease is frequent Flares can be controlled with high dose glucocorticoid via intravenous pulses at 30 mg methylprednisolone/kg/day for 3 consecutive days. However, steroid treatment at high dosage can present severe side effects for patients.

These standard treatments are generally nonspecific, are frequently associated with serious side-effects and do not significantly affect the progression of the disease or transition to life threatening kidney complications (lupus nephritis or LN). Consequently, there is a long-felt need in the art to develop new methods for treating SLE.

3. Rheumatoid Arthritis

Rheumatoid arthritis (RA) is characterized by chronic joint inflammation that typically leads to tissue damage and joint deformation. Although the precise etiology is not clear, it is generally thought to be an autoimmune disease with roles played by immune complexes, a variety of lymphoid cell types (T-cells, B-cells, neutrophils, macrophages, a number of pro-inflammatory cytokines such as TNF-α and IL-1β. (See *Harrison's Principles of Internal Medicine* (Kasper et al. eds., McGraw-Hill, New York 2005); Olsen and Stein, *N. Engl. J. Med.* 350:2167-2179, 2004.)

Rheumatoid arthritis is a systemic disease that affects the entire body and is one of the most common forms of arthritis. RA is immune-mediated and is particularly characterized by inflammation and subsequent tissue damage leading to severe disability and increased mortality. In particular, it is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

A variety of cytokines are produced locally in the rheumatoid joints. Numerous studies have demonstrated that IL-1 and TNF-α, two prototypic pro-inflammatory cytokines, play an important role in the mechanisms involved in synovial inflammation and in progressive joint destruction. Indeed, the administration of TNF-α and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2:135-149, 2002). Since RA is characterized by the presence of antibodies directed against Type II collagen, a major extracellular matrix component of joint cartilage, these antibodies are thought to mediate the release of the inflammatory cytokines, such as those described above, through their interaction with synoviocytes or other inflammatory cell types within the joint space.

Immunologic abnormalities that may be important in the pathogenesis of RA also include immune complexes found in joint fluid cells and in vasculitis. Contributing to these complexes are antibodies (such as RF) produced by plasma cells and T helper cells that infiltrate the synovial tissue and which can produce pro-inflammatory cytokines. Macrophages and their cytokines (e.g., TNF, GMCS-F) are also abundant in diseased synovium. Increased levels of adhesion molecules contribute to inflammatory cell emigration and retention in the synovial tissue. Increased macrophage-derived lining cells are also prominent, along with some lymphocytes.

Established treatments of RA include disease modifying anti-rheumatic drugs (DMARD) such as hydroxychloroquine, sulfasalazine, methotrexate, leflunomide, rituximab, infliximab, azathioprine, D-penicillamine, Gold (oral or intramuscular), minocycline and cyclosporine, coritcosteroids such as prednisone and non-steroidal anti-inflammatory drugs (NSAIDS). These treatments are generally nonspecific, are frequently associated with serious side-effects and do not significantly affect the progression of joint destruction. Consequently, there is a long-felt need in the art to develop new methods for treating RA.

The soluble FcγRIA polypeptides of the present invention could block the interaction of the immune complexes with inflammatory cell types in the synovium and prevent inflammation. Therefore, the FcγRIA polypeptides of the invention could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating cellular Fc receptors and/or the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

The administration of soluble hybrid FcγR polypeptides of the present invention to these CIA model mice can be used to evaluate the use of soluble FcγR to ameliorate symptoms and alter the course of disease. By way of example and without limitation, the injection of 0.1 mg to 2.0 mg of a soluble hybrid FcγR polypeptide of the invention per mouse (one to seven times a week for up to but not limited to 4 weeks via s.c., i.p., or i.m route of administration) can significantly reduce the disease score (paw score, incident of inflammation, or disease). Depending on the initiation of administration (e.g., prior to or at the time of collagen immunization, or at any time point following the second collagen immunization, including those time points at which the disease has already progressed), antagonists of the present invention can be efficacious in preventing rheumatoid arthritis, as well as preventing its progression. As shown by studies described herein, administration of a soluble FcγRIA polypeptide (residues 16-282 of SEQ ID NO:2) ameliorated symptoms and altered the course of disease in the mouse CIA model. (See Example 13, infra.)

Another model for immune complex mediated rheumatic disease is the collagen antibody-induced model of arthritis in mice. (See Terato et al., *J. Immunol.* 48: 2103-2108, 1992.) Joint disease is induced in this model by the intravenous injection of a cocktail of four monoclonal antibodies, such as Arthrogen-CIA® from Chemicon, directed against Type II collagen. Arthrogen-CIA® used for the induction of arthritis in mice is a mixture of four clones that recognize individual epitopes within an 83 amino acid peptide within the CB11 domain of type II collagen (Chemicon International technical brochure). These epitopes are similar in type II collagen from human, mice, cow, chicken, monkey, and rat. The antibodies localize to the joints of mice, where they form immune complexes with cartilage-specific type II collagen. The antigen-antibody immune complexes are thought to induce disease through their interaction with Fc gamma receptors located on the surface of inflammatory cell types within the joint. Typically, on day 0, 2-4 mg of Arthrogen-CIA cocktail is injected into mice by intravenous dosing. This is followed three days later with an intraperitoneal injection of 50-100 μg of LPS. (See Terato et al., *Autoimmunity* 22:137-147, 1995.) Arthritis, evident as red and swollen paws, develops with 1-2 days. In a typical experiment, the mice are treated on day 0 or day 3 by injection with soluble FcγRIA (100-2000 g protein) dissolved in a suitable vehicle. Dosing with soluble hybrid FcγR can, for instance, be given every other day starting on day 0 or day 3. The arthritis score for each animal can be assessed everyday joint swelling and joint thickness. In a typical experiment, a soluble hybrid FcγR decreases the arthritis score.

4. Mixed Connective Tissue Disease

Mixed connective tissue disease is a rare disorder characterized by clinical features of SLE, systemic sclerosis, polymyositis or dermatomyositis, and RA and by very high titers of circulating antinuclear antibody to a ribonucleoprotein (RNP) antigen. (See *Harrison's Principles of Internal Medicine*, supra; Kim and Grossman, *Rheum. Dis. Clin. North Am.* 31:549-565, 2005; Venables, *Lupus* 15:132-137, 2006.) This antibody in high titer, now referred to as anti-UI RNP, has been a justification for considering MCTD as a distinct clinical entity. MCTD has been challenged as a distinct disorder by those who consider it as a subset of SLE or scleroderma. Others prefer to classify MCTD as an undifferentiated connective tissue disease. Hand swelling, Raynaud's phenomenon, polyarthralgia, inflammatory myopathy, esophageal hypomotility, and pulmonary dysfunction are common. Diagnosis is by the combination of clinical features, antibodies to RNP, and absence of antibodies specific for other autoimmune diseases. In some patients, the disorder evolves into classic systemic sclerosis or SLE.

Raynaud's phenomenon may precede other manifestations by years. Frequently, the first manifestations resemble early SLE, scleroderma, polymyositis or dermatomyositis, or RA. Whatever the initial presentation, limited disease tends to progress and become widespread, and the clinical pattern changes over time. The most frequent finding is swelling of the hands that eventually produces a sausagelike appearance of the fingers. Skin findings include lupus or dermatomyositis-like rashes. Diffuse scleroderma-like skin changes and ischemic necrosis or ulceration of the fingertips are much less frequent in MCTD. Almost all patients have polyarthralgias, and 75% have frank arthritis. Often the arthritis is non-deforming, but erosive changes and deformities similar to those in RA may be present. Proximal muscle weakness with or without tenderness is common. Renal disease occurs in about 10% and is often mild but occasionally causes morbidity or mortality. A trigeminal sensory neuropathy develops more frequently in MCTD than in other connective tissue diseases. Rheumatoid factors are frequently positive, and titers are often high. The ESR is frequently elevated.

MCTD is typically suspected when additional overlapping features are present in patients appearing to have SLE, scleroderma, polymyositis, or RA. Patients are first tested for antinuclear antibodies (ANA) and antibody to extractable nuclear antigen (ENA) and RNP antigen. If results of these tests are compatible with MCTD (e.g., RNP antibodies very high), γ-globulin level, serum complement levels, rheumatoid factors, anti Jo-1 (anti histidyl t-RNA synthetase), and antibodies to the ribonuclease-resistant Smith (Sm) component of ENA, and double-stranded DNA are tested to exclude other possible diagnoses. Further workup depends on symptoms and signs; manifestations of myositis, renal involvement, or pulmonary involvement prompt tests of those organs (e.g., CPK, MRI, electromyogram, or muscle biopsy for diagnosis of myositis).

The overall 10-yr survival rate is 80%, but prognosis depends largely on which manifestations predominate. Causes of death include pulmonary hypertension, renal failure, MI, colonic perforation, disseminated infection, and cerebral hemorrhage. Some patients have sustained remissions for many years without treatment.

Mixed connective tissue disease (MCTD) occurs worldwide and in all races, with a peak incidence in the teens and 20s but MCTD is seen in children and the elderly. Women are predominantly affected. The incidence and prevalence has not been clearly established. In most studies, the number of patients with clinical and serologic features of MCTD is ~4-fold fewer than for SLE, suggesting an overall prevalence of about 10/100,000. (See *Harrison's Principles of Internal Medicine*, supra; Venables, supra.)

Current treatment for MCTD is similar to that for SLE, with corticosteroids if disease is moderate or severe. Most patients with moderate or severe disease respond to corticosteroids, particularly if treated early. Mild disease is often controlled by salicylates, other NSAIDs, anti-malarials, or sometimes low-dose corticosteroids. Severe major organ involvement usually requires higher doses of corticosteroids.

5. Polyarteritis Nodosa-HBV Associated

Originally described by Kussmaul and Maier in 1866, classic polyarteritis nodosa (PAN) is a multisystem disorder characterized by a wide range of symptoms. (See Fiorentino, J. Am. Acad. Dermatol. 48:311-340, 2003; Harrison's Principles of Internal Medicine, supra). PAN is a necrotizing vasculitis of small and medium-sized muscular arteries with characteristic involvement of renal and visceral arteries. The lesions are segmental and tend to involve bifurcations and branchings of arteries. In the acute stages of the disease, neutrophils infiltrate all layers of the vessel wall and perivascular areas, resulting in intimal proliferation and degeneration of the vessel wall. As the lesion progresses, mononuclear cells infiltrate the area, resulting in fibrinoid necrosis of the vessels with compromise of the lumen, thrombosis, infarction of the tissues supplied by the vessels, and hemorrhage. (See Fiorentino, supra.)

The presence of hepatitis B antigenemia is 10-30% of patients with systemic vasculitis, particularly of the PAN type, together with the isolation of circulating immune complexes composed of hepatitis B viral antigens, suggest an immunologic role in pathogenesis of the disease. This notion is supported by findings of deposition of hepatitis B antigen, IgM, and complement in blood vessel walls of patients with this disease. (See Fiorentino, supra.)

Patients usually present with fever, weight loss, arthralgias, and malaise. Muscle wasting, abdominal pain, mononeuritis complex, hypertension, orchitis, and congestive heart failure are major symptoms demonstrating vascular involvement of the respective organ systems. If secondary to hepatitis B infection, the clinical findings are the same. The prognosis of untreated PAN is poor, with a reported 5-year survival rate of 10-20%. (See Harrison's Principles of Internal Medicine, supra.) Death usually results from gastrointestinal complications, particularly bowel infarcts and perforation and by cardiovascular causes.

It is difficult to establish an accurate incidence of PAN because previous reports have combined the incidence of PAN with microscopic polyangiitis and related vasculitis disorders. The incidence of PAN has been estimated, however, at 5-9 cases per million (see Fiorentino, supra) and it is estimated that ~6% of cases are due to HBV infection although a range of frequency from 10-54% has been reported (26, 27).

PAN patients are currently treated with steroids with or without cyclophosphamide. (See Fiorentino, supra.) For patients with HBV, antiviral treatment with interferon-α with or without vidarabine and lamivudine is effective when combined with plasma exchange. (See Fiorentino, supra; Harrison's Principles of Internal Medicine, supra.)

6. Pemphigus Vulgaris

Pemphigus vulgaris (PV) is a blistering skin disease observed most commonly in elderly patients. The disease is characterized by the loss of cohesion between epidermal cells of the skin with the resulting formation of intraepidermal blisters. Direct immunofluorescence analysis of lesional or intact patient skin shows deposits of IgG on the surface of keratinocytes. Such deposits are derived from circulating IgG autoantibodies against desmogleins, transmembrane glycoproteins of the $Ca^{2+}$ dependent cadherin family. PV can be life threatening. The current mainstay of treatment is systemic steroids, such as prednisone. Other immunosuppressants such as azathioprine or mycophenolate mofetil are also used. (See Harrison's Principles of Internal Medicine, supra.)

7. Diseases Associated with Exogenous Antigens

Exogenous antigens produce a wide variety of immune complex diseases including those caused by infection with viruses, bacteria, or parasites as well as serum sickness caused by exposure to foreign proteins or drugs. (See Jancar and Crespo, supra; Harrison's Principles of Internal Medicine, supra; Knowles and Shear, Dermatol. Clin. 25:245-253, 2007; Wolf et al., Clin. Dermatol. 23:171-181, 2005.) The bacterial infections associated with tissue immune complex deposition include: streptococcal, staphylococcal and meningococcal; bartonellosis, borreliosis, leprosy, syphilis, and leptospirosis. The viral infections include: Hepatitis B (polyarteritis nodosa), Hepatitis C (cryoglobulinemia), HIV-related immune complex nephropathy, human parvovirus B19 infection, CMV infection, infectious mononucleosis, and dengue hemorrhagic fever. The parasitic diseases include: *Trypansoma, Plasmodium, Toxoplasma*, and *Schistosoma*.

Currently, the most common serum sickness-like reactions are due to exposure to non-protein drugs. Drugs that have been implicated in serum-sickness-like reactions include: allopurinal, arsenicals and mercurial derivatives, barbiturates, bupropion, cephalosporins, furazolidone, gold salts, griseofulvin, hydralazine, infliximab, iodides, methyldopa, penicillins, phenyloin, piperazine, procainamide, streptokinase, and sulfonamides. Other causes of serum sickness like reactions include exposure to heterologous serum, allergen extracts, blood products, hormones, hymenoptera venom, and vaccines.

B. Other Diseases Involving Antibody Production

1. Idiopathic Thrombocytopenia Purpura (ITP)

Idiopathic thrombocytopenia purpura (ITP) is a systemic autoimmune illness characterized by the presence of autoantibodies (IgG>IgM) directed against specific platelet membrane glycoproteins that results in platelet destruction (leading to thrombocytopenia), and which is characterized by extensive ecchymoses and hemorrhages from mucous membranes, anemia, and extreme weakness. (See Harrison's Principles of Internal Medicine, supra Cines and McMillan, Annu. Rev. Med. 56:425-442, 2005; Stasi and Provan, Mayo Clin. Proc. 79:504-522, 2004.)

The platelet count becomes exceedingly low and spontaneous bleeding from the gums, gastrointestinal tract and nose can be seen. Purpura refers to the purplish-looking areas of the skin and mucous membranes (such as the lining of the mouth) where bleeding has occurred as a result of decreased platelets. Physical examination may demonstrate enlargement of the spleen. A typical rash occurs due to microscopic hemorrhage of small blood vessels in the skin. Platelet counts under 10,000 can lead to spontaneous hemorrhage into the brain, causing death. Also called immune thrombocytopenic purpura, purpura hemorrhagica, thrombocytopenic purpura, Werlhof's disease. Although most cases are asymptomatic, very low platelet counts can lead to a bleeding diathesis and purpura. There are two types of ITP, acute ITP that affects children (similar incidence in males and females) and chronic ITP affecting adults (more often women; 2.6 to 1; 72% of ITP patients older than 10 are women). Most children recover without treatment. Peak prevalence in children is 2-4 years, and in adults is 20-50 years; approximately 40% of all ITP patients are younger than 10 years old.

Incidence of ITP: 4-8 per 100,000 children per year, 66 cases per million adults, 50 cases per million children. New cases of chronic refractory ITP comprise ~10 cases per million per year. The number of individuals in the United States with ITP has been estimated to be approximately 200,000. There are about 100 total new cases of ITP per million people per year. Approximately half of the new cases are in children.

Mild ITP does not require treatment. When platelet counts fall under 10,000 per microliter, or under 50,000 when hemorrhage occurs (e.g., in the digestive tract or in a severe nosebleed) treatment is generally initiated with steroids. (See Cines and McMillan, supra.) Intravenous immunoglobulin (IVIg) is used for life threatening cases. Later, so-called steroid-sparing agents (alternatively called DMARDs) may be used. When these strategies fail, splenectomy is often undertaken, as platelets targeted for destruction will often meet their fate in the spleen. A relatively new strategy is treatment with anti-D, an agent usually used in mothers who have been sensitized to rhesus antigen by an Rh+ baby. Other chemotherapeutic drugs such as vincristine, azathioprine (Imuran), Danazol, cyclophosphamide, and cyclosporine are prescribed for patients only in the severe case where other treatments have not shown benefit since these drugs have potentially harmful side effects. Mg, while effective, is expensive and the improvement is temporary (generally lasting less than a month). However, in the case of a pre-splenectomy ITP patient with dangerously low platelet counts, and a poor response to other treatments, IVIg treatment can increase platelet counts, making the splenectomy operation less dangerous.

2. Sjogren's Syndrome

Sjogren's syndrome (SS) is a chronic autoimmune disorder characterized by lymphocytic infiltration of salivary and lacrimal glands, resulting in dry eyes and dry mouth. It is classified as either primary (autoimmune sicca (dryness) syndrome without underlying connective tissue disorder) or secondary (autoimmune-mediated sicca syndrome in a patient with ongoing connective tissue disorder like RA, SLE or SSc). (See *Harrison's Principles of Internal Medicine*, supra.) The female-to-male ratio for SS is 9:1, with a mean age at diagnosis of 60 years. A model of pathogenesis postulates a virus or environmental insult in the appropriate genetic/hormonal background leads to epitheliitis in the salivary and lacrimal glands. The resulting mononuclear cell infiltrates (~70% CD4+ T-cells, 25% CD8+ T-cells, 20-30% B-cells) release cytokines (IFNγ), which in turn activate macrophages that release proinflammatory cytokines: TNFα, IL-1β and IL-6. These cytokines then cause the release of MMPs from acinar cells, which degrade the basement membrane collagen. In time, the glandular tissue is replaced with scar tissue and fat. (See *Harrison's Principles of Internal Medicine*, supra.)

In addition to dry mouth/eye symptoms, other symptoms can include: esophageal dysmotility, peripheral neuropathy arthralgia and fibromyalgia. 60% of patients present with autoantibodies (rheumatoid factor, ANA, Ro/SS-A, La/SS-B) and suffer extreme fatigue. SS patients are reported to have 44 times higher risk for developing lymphoma.

A variety of treatments have been used for SS including NSAIDs, steroids, hydroxychloroquine, and methotrexate. Several anti-cytokine therapies are also in use but are not recommended as first-line therapy. These include: REMICADE, ENBREL, IFN-α, anti-IFN-γ, RITUXAN, cyclosporine, tacrolimus, and various topical ophthalmic preparations.

3. Antiphospholipid Antibody Syndrome

The antiphospholipid antibody syndrome is a common autoimmune prothrombotic condition characterized by arterial and/or venous thrombosis and pregnancy morbidity associated with persistently positive anti-cardiolipin antibodies and/or lupus anticoagulant. (See *Harrison's Principles of Internal Medicine*, supra; Blume and Miller, *Cutis* 78:409-415, 2006; Fischer et al., *Semin. Nephrol.* 27:35-46, 2007.) Recent evidence that some of these antibodies (IgG and IgM) are directly against phospholipid binding proteins (B2-glycoprotein 1, prothrombin, protein C, protein S, TPA, and annexin V rather than the negatively charged phospholipids themselves). APS can occur in association with other autoimmune disease, most commonly with SLE (secondary APS) or as an isolated disorder (primary APS).

APS affects any size of vessel and any organ of the body. Clinical features include peripheral venous and arterial thrombosis (deep vein thrombosis), fetal loss, skin disease, cardiac and pulmonary manifestations, renal involvement, and neurological disorders (stroke). Thrombotic complications are the main cause of death in SLE patients.

APS is a common cause of acquired thrombophilia, with an estimated 35,000 new cases of APS-associated venous thrombosis and 5000 new cases of arterial thrombosis in the U.S. per year. Patients with APS antibodies are 3-10 times more likely to have a recurrent thrombosis than patients without these antibodies. In the U.S., about 2% of the general population tests positive for anti-phospholipid antibodies (AAs), including lupus anticoagulant, anti-cardiolipin antibodies or both. AAs were detected in 46% of patients with stroke or transient ischemic attack under 50 years of age and in 21% of young survivors (<45 years of age) of myocardial infarction. The prevalence of AAs in patients with SLE is very high (30-50%). The prevalence of elevated AAs in dialysis patients varies between 0.7% and 69% in the published literature. In patients with APS, the ratio of women to men is about 2 to 1 for the primary form and 9 to 1 for cases associated with SLE.

The current therapy for patients who have APS but haven't experienced thrombotic events or cutaneous changes is lifelong therapy with low dose aspirin. A patient with medium to high AA titers or thrombosis needs immediate treatment with an anticoagulant such as heparin. Long-term therapy is anticoagulation with warfarin. There is some clinical trial activity of using cyclophosphamide in patients with life-threatening APS and using steroids to control APS-associated pregnancy loss. There is not much precedent for using anti-B cell therapies for controlling the levels of AAs.

4. Dermatomyositis

Dermatomyositis is a progressive condition characterized by symmetric proximal muscular weakness with elevated muscle enzyme levels and a skin rash, typically a purplish-red on the face, and edema of the eyelids and periorbital tissue. (See Dalakas, *Curr. Opin. Pharmacol.* 1:300-306, 2001; Dalakas, *Nat. Clin. Pract. Rheumatol.* 2:219-227, 2006.) Affected muscle tissue shows degeneration of fibers with a chronic inflammatory reaction, occurs in children and adults, and in the latter may be associated with visceral cancer. The cause of PM/DM is unknown. Although it rarely occurs in multiple family members, it may be linked to certain HLA types (e.g., DR3, DR5, or DR7). Infectious agents, including viruses, and *Toxoplasma* and *Borrelia* species, have been suggested as possible triggers of the disease. Several cases of drug-induced disease have been reported (e.g., hydroxyurea, penicillamine, statins, quinidine, and phenylbutazone). Immunological and humoral abnormalities are common (e.g., increased TNF-α in muscle, circulating myositis-specific autoAbs; abnormal T- and B-cell activity; family history of other autoimmune diseases). B cells are the most abundant inflammatory cells at the perivascular sites.

Dermatomyositis is associated with skin problems (typically a purplish-red rash on the face, and edema of the eyelids and periorbital tissue) and since articular, cardiac, pulmonary, and gastrointestinal manifestations occur in up to 50% of the patients, the illness can be associated with severe morbidity. It is often associated with other connective tissue autoimmune diseases, such as SLE, scleroderma, and RA. Unlike RA, arthritis associated specifically with DM/PM is not erosive or deforming. Consistent with skin changes associated with other autoimmune connective tissue diseases, such as SLE, there are perivascular inflammatory infiltrates in the skin. PM/DM is not usually life-threatening, but patients often develop residual weakness, disability, and reduced Quality of Life. PM/DM may cause death because of severe muscle weakness and/or cardiopulmonary involvement. Risk of malignancy is very high in patients with DM (incidence ratio=26) but not PM; the malignancy occurs more frequently in adults older than 60 years. Calcinosis (manifested by firm, yellow- or flesh-colored nodules) of the skin or muscle is unusual in adults but occurs in up to 40% of children or adolescents with DM; it is very debilitating. They can extrude through the surface of the skin, in which case secondary infection may occur.

The incidence of inflammatory myopathies (polymyositis alone, and polymyositis and dermatomyositis combined has been estimated at 0.1 and 1 per 100,000 people, respectively (no ethnic bias), and is apparently increasing. Prevalence is 1 and 6 per 100,000 for PM alone and PM/DM combined, respectively. Females are affected more than males (~2:1). PM/DM can occur in people of any age. Two peak ages of onset exist. In adults, the peak age of onset is approximately 50 years, and, in children, the peak age is approximately 5-10 years.

The mainstay of treatment is steroids. (See Dalakas, *Jama* 291:2367-2375, 2004; Dalakas, *Pharmacol. Ther.* 102:177-193, 2004.) Immunosuppressant therapy with methotrexate, azathioprine, and mycophenolate mofetil have also been used. In refractory patients, IVIg has been used for short-term therapy. Emerging therapies for this disorder include Rituxan. Although there is some concern that TNF antagonists may increase some of the risks associated with DM (infection, malignancy, induction of other autoimmune disease), REMICADE and ENBREL are being studied in ongoing clinical trials for this disorder.

5. Guillain-Barre Syndrome

Guillian-Barre syndrome is a severe post infectious neurological disorder. The nerve damage observed in GBS patients is presumably caused by cross-reactive anti-ganglioside antibodies. The cellular immunological background of the production of cross-reactive antibodies in GBS is largely unknown. Some have hypothesized that a differential response of dendritic cells to the most frequent antecedent infection in GBS, *Campylobacter jejuni*, results in enhanced B-cell proliferation and differentiation into autoreactive plasma cells. Host related factors as well as pathogenic factors may be related to this. (See *Harrison's Principles of Internal Medicine*, supra; Lewis, *Neurol. Clin.* 25:71-87, 2007; Said, *Neurol. Clin.* 25:115-137, 2007; Yuki, *Muscle Nerve* 35:691-711, 2007.)

GBS is a devastating disorder with a mortality of 5-15%. IVIg are the first choice treatment for these patients. (See *Harrison's Principles of Internal Medicine*, supra). Still, about 50% of patients are unable to walk independently after 6 months. GBS consists of at least four subtypes of acute peripheral neuropathy. The histological appearance of the acute inflammatory demyelinating polyradiculoneuropathy (AIDP) subtype resembles experimental autoimmune neuritis, which is predominantly caused by T cells directed against peptides from the myelin proteins P0, P2, and PMP22. The role of T-cell-mediated immunity in AIDP remains unclear and there is evidence for the involvement of antibodies and complement. Strong evidence now exists that axonal subtypes of GBS, acute motor axonal neuropathy (AMAN), and acute motor and sensory axonal neuropathy (AMSAN), are caused by antibodies to gangliosides on the axolemma that target macrophages to invade the axon at the node of Ranvier. About a quarter of patients with GBS have had a recent *Campylobacter jejuni* infection, and axonal forms of the disease are especially common in these people. The lipo-oligosaccharide from the *C jejuni* bacterial wall contains ganglioside-like structures and its injection into rabbits induces a neuropathy that resembles acute motor axonal neuropathy. Antibodies to GM1, GM1b, GD1a, and GalNac-GD1a are in particular implicated in acute motor axonal neuropathy and, with the exception of GalNacGD1a, in acute motor and sensory axonal neuropathy. The Fisher's syndrome subtype is especially associated with antibodies to GQ1b, and similar cross-reactivity with ganglioside structures in the wall of *C jejuni* has been discovered. Anti-GQ1b antibodies have been shown to damage the motor nerve terminal in vitro by a complement-mediated mechanism.

GBS is a rare disorder and affects men and women equally in the US (NIH, The National Women's Health Centre, 2004). GBS affects 1 person per 100,000 population in the US (NIH, The National Women's Health Centre, 2004). The U.S. prevalence of all chronic inflammatory demyelinating polyneuropathies (CIDP), including GBS is about −1 to 7.7 per 100,000 (2,000-15,000 cases in U.S.). However, this is probably an underestimate, assuming that CIDP constitute 5% of all neuropathies (10 million cases), then one might expect there are actually ~300,000 (active)-500,000 cases in total.

IVIg and plasmapheresis are currently used as therapy for GBS. Since GBS is an autoimmune neuropathy, it is anticipated that therapies directed towards T-cells, B-cells, and/or complement may be useful in these diseases.

6. Goodpasture's Syndrome

The term "Goodpasture's syndrome" (GPS) is an eponym derived from a report in 1919 by Ernest Goodpasture, who described the clinical syndrome of pulmonary hemorrhage associated with influenza infection and the histologic finding of acute crescentic glomerulonephritis. Over the years, the terminology has been used in different ways by different persons, some including all causes of pulmonary hemorrhage with renal dysfunction as GPS. Others limited the term GPS to patients with pulmonary hemorrhage associated with anti-glomerular basement membrane (anti-GBM) antibodies, as opposed to glomerulonephritis with anti-GBM antibodies but without pulmonary hemorrhage. Yet others espouse the concept of anti-type-IV collagen disease rather than GPS.

The sine qua non for the diagnosis of GPS is demonstration of bound anti-GBM antibodies in the glomeruli of the kidneys. Circulating anti-GBM antibodies are present in more than 90% of patients with anti-GBM disease. The clinical course of untreated, and even treated, GPS is bleak; this disease is associated with an extremely poor prognosis.

GPS is a rare disease, having an incidence of about 0.1 case per million people. The disease is more common in whites than in African Americans and may be more common in certain other racial groups, such as the Maoris in New Zealand. GPS can present year round, but its incidence appears to increase in the spring and early summer.

The current therapies for GPS include steroids, immunosuppressants, and plasma exchange. Since the renal pathology appears to be due to the accumulation of anti-GBM antibodies in kidney glomeruli, B-cell directed therapies may be useful in this disease.

From the foregoing, it will be appreciated that, although specific embodiments of the invention have been described herein for purposes of illustration, various modifications may be made without deviating from the spirit and scope of the invention. Accordingly, the invention is further illustrated by the following non-limiting examples and is not limited except as by the appended claims.

Example 1

Construction of Mammalian Soluble FcγRIA Expression Constructs that Express FcγRIA-CEE, FcγRIA-CHIS, and FcγRIA-CFLAG Tagged Proteins An expression construct containing the extracellular domain of human FcγRIA with a C-terminal tag, either Glu-Glu (CEE), six His (CHIS), or FLAG (CFLAG), is constructed via PCR and homologous recombination using a DNA fragment encoding FcγRIA (SEQ ID NO:14) and the expression vector pZMP20.

The PCR fragment encoding FcγRIA-CEE contains a 5' overlap with the pZMP20 vector sequence in the 5' non-translated region, an FcγRIA extracellular domain coding region portion of SEQ ID NO:14 (nucleotides 1-846), the Glu-Glu tag (Glu Glu Tyr Met Pro Met Glu; SEQ ID NO:15) coding sequence, and a 3' overlap with the pZMP20 vector in the poliovirus internal ribosome entry site region. The PCR amplification reaction uses the 5' oligonucleotide "100" (ACAGGTGTCCAGGGAATTCATATAGGCCG-GCCACCATGTGGTTCTTGACAACTCTG; SEQ ID NO:16), the 3' oligonucleotide "200" (CAACCCCA-GAGCTGTTTTAAGGCGCGCCTCTAGAT TATTC-CATGGGCATGTATTCTTCCACTTGAAGCTC-CAACTCAGG; SEQ ID NO:17), and a previously generated DNA clone of FcγRIA as the template (SEQ ID NO:14).

The PCR amplification reaction condition is as follows: 1 cycle, 94° C., 5 minutes; 35 cycles, 94° C., 1 minute, followed by 55° C., 2 minutes, followed by 72° C., 3 minutes; 1 cycle, 72° C., 10 minutes. The PCR reaction mixture is run on a 1% agarose gel and the DNA fragment corresponding to the expected size is extracted from the gel using a QIAquick™ Gel Extraction Kit (Qiagen, Cat. No. 28704).

Plasmid pZMP20 is a mammalian expression vector containing an expression cassette having the chimeric CMV enhancer/MPSV promoter, a BglII site for linearization prior to yeast recombination, an internal ribosome entry element from poliovirus, the extracellular domain of CD8 truncated at the C-terminal end of the transmembrane domain; an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*.

The plasmid pZMP20 is digested with BglII prior to recombination in yeast with the gel extracted FcγRIA-CEE PCR fragment. One hundred μl of competent yeast (*S. cerevisiae*) cells are combined with 10 μl of the FcγRIA-CEE insert DNA and 100 ng of BglII digested pZMP20 vector, and the mix is transferred to a 0.2 cm electroporation cuvette. The yeast/DNA mixture is electropulsed using power supply (BioRad Laboratories, Hercules, Calif.) settings of 0.75 kV (5 kV/cm), ∞ ohms, and 25 μF. Six hundred μl of 1.2 M sorbitol is added to the cuvette, and the yeast is plated in 100 μl and 300 μl aliquots onto two URA-D plates and incubated at 30° C. After about 72 hours, the Ura+ yeast transformants from a single plate are resuspended in 1 ml $H_2O$ and spun briefly to pellet the yeast cells. The cell pellet is resuspended in 0.5 ml of lysis buffer (2% Triton X-100, 1% SDS, 100 mM NaCl, 10 mM Tris, pH 8.0, 1 mM EDTA). The five hundred μl of the lysis mixture is added to an Eppendorf tube containing 250 μl acid-washed glass beads and 300 μl phenol-chloroform, is vortexed for 3 minutes, and spun for 5 minutes in an Eppendorf centrifuge at maximum speed. Three hundred μl of the aqueous phase is transferred to a fresh tube, and the DNA is precipitated with 600 μl ethanol, followed by centrifugation for 30 minutes at maximum speed. The tube is decanted and the pellet is washed with 1 mL of 70% ethanol. The tube is decanted and the DNA pellet is resuspended in 30 μl 10 mM Tris, pH 8.0, 1 mM EDTA.

Transformation of electrocompetent *E. coli* host cells (DH12S) is done using 5 μl of the yeast DNA preparation and 50 μl of *E. coli* cells. The cells are electropulsed at 2.0 kV, 25 μF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is added and then the cells are plated in 50 μl and 200 μl aliquots on two LB AMP plates (LB broth (Lennox), 1.8% Bacto™ Agar (Difco), 100 mg/L Ampicillin).

The inserts of three DNA clones for the construct are subjected to sequence analysis and one clone containing the correct sequence is selected. Large-scale plasmid DNA is isolated using a commercially available kit (QIAGEN Plasmid Mega Kit, Qiagen, Valencia, Calif.) according to manufacturer's instructions.

The same process is used to prepare the FcγRIA with a C-terminal his tag, composed of Gly Ser Gly Gly His His His His His His (SEQ ID NO:18) (FcγRIA-CHIS) or the C-terminal FLAG tag, composed of Gly Ser Asp Tyr Lys Asp Asp Asp Asp Lys (SEQ ID NO:19) (FcγRIA-CFLAG). To prepare these constructs, instead of the 3' oligonucleotide "200", the 3' oligonucleotide "300" (CAACCCCAGAGCT-GTTTTAAGGCGCGCCTCTAGATTAGTGATGGT-GATGGTGATG TCCACCAGATCCCACTTGAAGCTC-CAACTCAGG; SEQ ID NO:20) is used to generate FcγRIA-CHIS or the 3' oligonucleotide "400" (CAAC-CCCAGAGCTGTTTAAGGCGCGCCTCTAGATTA CTTATCATCATCATCCTTATAATCGGATCCCACTT-GAAGCTCCAACTCAGG; SEQ ID NO:21) is used to generate FcγRIA-CFLAG.

Example 2

Transfection and Expression of Soluble FcγRIA Receptor Expression Constructs that Express the FcγRIA-CEE, FcγRIA-CHIS, and FcγRIA-CFLAG C-Terminal Tagged Proteins Three sets of 200 μg of each of the soluble FcγRIA tagged expression constructs are separately digested with 200 units of PvuI at 37° C. for three hours, precipitated with isopropyl alcohol, and centrifuged in a 1.5 mL microfuge tube. The supernatant is decanted off the pellet, and the pellet is washed with 1 mL of 70% ethanol and allowed to incubate for 5 minutes at room temperature. The tube is spun in a microfuge for 10 minutes at 14,000 RPM and the supernatant is decanted off the pellet. The pellet is then resuspended in 750 μl of CHO cell tissue culture medium in a sterile environment, allowed to incubate at 60° C. for 30 minutes, and is allowed to cool to room temperature. Approximately $5 \times 10^6$ CHO cells are pelleted in each of three tubes and are resuspended using the DNA-medium solution. The DNA/cell mixtures are placed in a 0.4 cm gap cuvette and electroporated using the following parameters; 950 μF, high capacitance, at 300 V. The contents of the cuvettes are then removed, pooled, and diluted to 25 mL with CHO cell tissue culture medium and placed in a 125 mL shake flask. The flask is placed in an incubator on a shaker at 37° C., 6% $CO_2$ with shaking at 120 RPM.

The CHO cells are subjected to nutrient selection followed by step amplification to 200 nM methotrexate (MTX), and then to 1 μM MTX. Tagged protein expression is confirmed by Western blot, and the CHO cell pool is scaled-up for harvests for protein purification.

Example 3

Purification of FcγRIA-CH6

An expression construct containing the extracellular domain of human FcγRIA with a C-terminal six His (CHIS) tag was constructed as described in Example 1, supra. This construct was transfected into and expressed in CHO cells as described in Example 2, supra. The encoded His-tagged FcγRIA, referred to in the Examples above as "FcγRIA-CHIS," is also referred to herein as "FcγRIA-CH6" or "pFCGR1A CH6." The nucleotide coding sequence for FcγRIA-CH6 is shown in SEQ ID NO:22, and the corresponding FcγRIA-CH6 amino acid sequence is shown in SEQ ID NO:23. The expressed FcγRIA-CH6 was purified as described below. FcγRIA-CH6 was purified from CHO conditioned media by a combination of Ni IMAC capture, chromatography on Q Sepharose, and size exclusion chromatography on Superdex 200. Ni IMAC capture: CHO conditioned media was sterile filtered (0.22 μm) and concentrated 10× using a peristaltic pump system equipped with 10 kD MWCO 0.1 $m^2$ membrane. Concentrated media was buffer exchanged with at least 5 CV of 50 mM $NaPO_4$, 500 mM NaCl pH 7.5 and was adjusted to a final concentration of 25 mM imidazole. The pH was adjusted to 7.5 using either concentrated NaOH or HC, if necessary. The His-tagged FcγRIA protein was captured using IMAC binding to Ni-NTA His Bind Superflow resin. Prior to application of media, the resin was equilibrated in 50 mM $NaPO_4$, 500 mM NaCl, 25 mM Imidazole pH 7.5. Binding was allowed to occur overnight at 4° C. in either batch mode using an appropriately sized roller bottle or column mode using a chromatography station. Following the load, the resin was washed with at least 10 CV of 50 mM $NaPO_4$, 500 mM NaCl, and 25 mM Imidazole pH 7.5. Elution of bound protein was accomplished using either a gradient or steps of increasing imidazole concentration in 50 mM $NaPO_4$, 500 mM NaCl pH 7.5, with 500 mM Imidazole being the end point in the elution. Fractions were collected and analyzed by western blotting, SDS-PAGE, and RP-HPLC and fractions containing FcγRIA-CH6 were combined.

Q Sepharose Passive Chromatography: The IMAC pool containing FcγRIA-CH6 was buffer exchanged with 15 CV into 50 mM $NaPO_4$, 150 mM NaCl pH 7.5 through the use of a Labscale TFF system equipped with 3×10 kD MWCO 0.1 $cm^2$ membranes. A 1.0 mL sample of Q Sepharose resin per 7.5 mg of FcγRIA-CH6 was charged using at least 10 CV of 50 mM $NaPO_4$, 2M NaCl pH 7.5, and then equilibrated with 10 CV of 50 mM $NaPO_4$, 150 mM NaCl pH 7.5. Resin and the adjusted IMAC pool were combined and incubated overnight at 4° C. with gentle agitation. The slurry was transferred to a gravity flow column, the flow-through was collected and the column was washed with at least 5 CV of equilibration buffer. The flow-through and wash fractions were combined and assessed for the presence of FcγRIA-CH6 by RP-HPLC and SDS-PAGE.

Size Exclusion Chromatography: The Q Sepharose flow-through + wash fraction was concentrated at least 10- to 20-fold using either the TFF labscale system equipped with a 10 kD MWCO 0.1 $cm^2$ membrane, a stirred cell system equipped with a YM30 membrane of appropriate diameter, or a 30 kD MWCO Ultracel centrifugal membrane, depending on the fraction volume. The concentrated FcγRIA-CH6 fraction was injected over a Superdex 200 column of appropriate size for the amount of volume and mass injected. The column was equilibrated in formulation buffer which contained. 50 mM $NaPO_4$, 109 mM NaCl, pH 7.3 or 35 mM $NaPO_4$, 120 mM NaCl pH 7.2. The column was eluted isocratically at a flow rate no greater than 45 cm/hr, fractions were collected and analyzed for the presence of FcγRIA-CH6 by SDS-PAGE and RP-HPLC. Fractions containing FcγRIA-CH6 were combined and concentrated to the desired concentration using a stirred cell apparatus equipped with a YM30 membrane (30 kD MWCO). The final FcγRIA-CH6 concentrate was filtered through a 0.22 um sterile filter and stored at −80° C. until use.

Example 4

Construction, Expression, and Purification of Soluble FcγRIIA-CH6 and FcγRIIIA-CH6

In addition to construction, expression, and purification of a soluble monomeric form of FcγRIA with a C-terminal His6 tag as described above in Examples 1, 2, and 3, supra, soluble monomeric forms of FcγRIIA and FcγRIIIA were also generated using similar methods.

Briefly, expression constructs encoding soluble monomeric forms of the FcγRIIA and FcγRIIIA were generated using DNA sequences encoding their native signal sequence, their extracellular domain, and a C-terminal His6 tag (GSGGHHHHHH; SEQ ID NO:18). The DNA sequence encoded amino acids 1-212 for FcγRIIA (amino acids 1-212 of SEQ ID NO:25) and 1-195 for FcγRIIA (amino acids 1-195 of SEQ ID NO:27). Receptors were purified from supernatants derived from Chinese hamster ovary (CHO) DXB-11 cells (Larry Chasin, Columbia University, New York, N.Y.). CHO-conditioned media were sterile filtered, concentrated, and buffer exchanged into 50 mM $NaPO_4$, 500 mM NaCl, 25 mM imidazole, pH 7.5 (Buffer A). The His-tagged FcγR proteins (FcγRIIA-CH6 and FcγRIIIA-CH6) were captured using Ni-NTA His Bind Superflow resin (Novagen, Madison, Wis.) equilibrated in Buffer A. Elution of bound protein was accomplished using a gradient of imidazole (0-500 mM) in 50 mM $NaPO_4$, 500 mM NaCl, pH 7.5. Fractions were analyzed for soluble FcγR by SDS-PAGE and Western blotting (anti-6× Histidine HRP mouse IgG1, R & D Systems, Minneapolis, Minn.).

The Ni-NTA fractions containing soluble FcγR were buffer-exchanged into 50 mM $NaPO_4$, 150 mM NaCl, pH 7.5 (Buffer B) and incubated with Q Sepharose 4FF resin (GE Healthcare, Uppsala, Sweden) that was pre-equilibrated in Buffer B overnight at 4° C. The slurry was transferred to a gravity flow column, the flow-through and wash fractions were combined and assessed for the presence of soluble FcγR as described above. The combined fractions were concentrated and injected onto a Superdex 200 Hiload (GE Healthcare, Uppsala, Sweden) column equilibrated in 50 mM $NaPO_4$, 109 mM NaCl, pH 7.3 (Buffer C). The column was eluted in Buffer C and fractions containing soluble FcγR were combined, concentrated, sterile-filtered, and stored at −80° C. FcγRIIA-CH6 and FcγRIIIA-CH6 were analyzed by SDS-PAGE, Western blotting, N-terminal sequencing, and size exclusion multi-angle light scattering. Endotoxin levels were <1.0 endotoxin units/mL for each receptor preparation formulated at ~20 mg/mL.

The nucleotide coding sequences for FcγRIIA-CH6 and FcγRIIIA-CH6 are shown in SEQ ID NO:24 and SEQ ID NO:26, respectively. The encoded polypeptide sequences for FcγRIIA-CH6 and FcγRIIIA-CH6 and shown in SEQ ID NO:25 and SEQ ID NO:27, respectively. N-terminal sequence analysis showed Gln-34 as the start site for mature FcγRIIA-CH6 and both Met-18 and Glu-21 as the start site for mature FcγRIIIA-CH6. Accordingly, the mature form the of FcγRIIA-CH6 polypeptide, without the signal sequence, corresponds to amino acid residues 34-222 of SEQ ID NO:25, while the mature forms of FcγRIIIA-CH6 correspond to amino acid residues 18-205 and 21-205 of SEQ ID NO:27.

Example 5

Binding of Soluble His-Tagged FcγR
(FcγRIA-CH6, FcγRIIA-CH6, and FcγRIIIA-CH6)
to Immobilized Human IgG1

Measurements were performed using a Biacore 3000 instrument (Piscataway, N.J.). Activation of the sensor chip surface and covalent immobilization of the IgG1 antibody (Lambda from human myeloma plasma, Sigma-Aldrich, St Louis, Mo.) was performed using 0.2 M N-ethyl-N'-(3-diethylamino-propyl) carbodiimide and 0.05 M N-hydroxysuccinamide and the Biacore Control Software. The human IgG1 antibody, diluted to 11 µg/mL in 10 mM sodium acetate, pH 5.0, was immobilized to prepare the specific binding flow cell, and a second flow cell was activated, but not exposed to IgG1 to prepare the reference flow cell. The un-reacted ester sites on both the specific binding and reference flow cells were blocked with 1 M ethanolamine hydrochloride.

For kinetic analysis of soluble FcγRIA binding, the IgG1 antibody was immobilized at a level of 458 resonance units (RU). FcγRIA-CH6 was injected over both the active and reference flow cells in series. For kinetic analysis of FcγRIA-CH6 binding, a concentration range of 0.16 to $10.3 \times 10^{-9}$ M of FcγRIA-CH6 in HBS-EP (Biacore) assay buffer (10 mM Hepes, pH 7.4, 0.15M NaCl, 3.5 mM EDTA, 0.005% polysorbate 20) was used. FcγRIA-CH6 was injected at a flow rate of 40 µL/min for 3 minutes. Subsequently, the FcγRIA-CH6 solution was switched to HBS-EP buffer and dissociation was measured for 3 minutes. Each FcγRIA-CH6 concentration was tested in duplicate using a random sequence. Each measurement was followed by a single 30 second injection of 10 mM glycine-HCl, pH 1.8 at 50 µL/min to regenerate the IgG1 surface.

For equilibrium analyses of soluble FcγRIIA and FcγRIIIA binding, the IgG1 antibody was immobilized at a level of 1013 RU. A concentration range of $0.03-24 \times 10^{-6}$ M of soluble FcγR was used. Each soluble FcγR (FcγRIIA-CH6 and FcγRIIIA-CH6) was injected at a flow rate of 10 µL/min for 1 minute. The dissociation time for each FcγR was 5 minutes. Each FcγRIIA-CH6 and FcγRIIA-CH6 concentration was tested in duplicate using a random sequence. Each measurement was followed by a single 30 second injection of HBS-EP at 30 µL/min to regenerate the IgG1 surface.

Binding curves for all three soluble FcγRs were processed by subtraction of the reference surface curve from the specific binding surface curve, as well as subtraction of a buffer-injection curve. The processed binding curves were globally fitted to a 1:1 binding model and the resulting kinetic and equilibrium constants were evaluated using Biacore software.

The soluble FcγRs bound to immobilized human IgG1 in a manner that was best-fit by a 1:1 binding interaction. The IgG1 exhibited some loss of binding activity upon covalent immobilization and the activity of the surface ranged from 26-81% of the theoretical maximum. The association and dissociation phases of FcγRIA-CH6 binding to IgG1 were measurable over a time period of >200 seconds, allowing kinetic analysis of the binding curves. FcγRIA-CH6 bound to IgG1 with association ($k_a$) and dissociation ($k_d$) rate constants of $2.8 \times 10^6$ M$^{-1}$s$^{-1}$ and $4.6 \times 10^{-4}$ s$^{-1}$, respectively, yielding an equilibrium dissociation constant ($K_D$) of $1.7 \times 10^{-10}$ M. The association/dissociation rates for FcγRIIA-CH6 and FcγRIIIA-CH6 were too fast to measure accurately, so the equilibrium dissociation constants were determined at steady state. Binding of FcγRIIIA-CH6 and FcγRIIA-CH6 to IgG1 was saturable and of low affinity with estimated $K_D$s of $0.63 \times 10^{-6}$ M and $1.9 \times 10^{-6}$ M, respectively. Each soluble FcγR bound to immobilized rabbit anti-OVA IgG with rates and affinities similar to that observed with human IgG1.

Example 6

Construction of Mammalian Soluble FcγRIA
Expression Constructs that Expresses Soluble
Monomeric Untagged FcγRIA Protein Two expression constructs containing the extracellular domain of human FcγRIA were constructed via PCR and homologous recombination using a DNA fragment encoding the extracellular domain of a short version FcγRIA (amino acids 1-282 of SEQ ID NO:2) and a long version FcγRIA (additional ten amino acids at the C-terminus) (amino acids 1-292 of SEQ ID NO:2) and the expression vector pZMP31.

PCR fragments encoding the short and long version of FcγRIA were constructed to contain a 5' overlap with the pZMP31 vector sequence in the 5' non-translated region, the FcγRIA extracellular domain coding region corresponding to SEQ ID NO:2 amino acid residues 1-282 or 1-292, respectively, and a 3' overlap with the pZMP31 vector in the poliovirus internal ribosome entry site region. The PCR amplification reaction for both the short and long version used the 5' oligonucleotide "zc57709" (ACTTTOC-CTTTCTCTCCACAGGTGTCCAGGGAAT-TCATATAGGC CGGCCACCATGTGGTTCTT-GACAACT; SEQ ID NO:28). The 3' oligonucleotide "zc57710" (TGGGGTGGGTACAACCCCAGAGCTGTT-TAAGGCGCGCCTTTAGCCAAGCACTTGAAGC TCCA; SEQ ID NO:29) was used for the short version and the 3' oligonucleotide "zc57712" (TGGGGTGGGTA-CAACCCCAGAGCTGTTTrAAGGCGCGCCTTTAAT-GAAACCAGACAGGA GT; SEQ ID NO:30) was used for the long version. The FcγRIA template was from a previously generated cDNA of FcγRIA.

The PCR amplification reaction conditions were as follows: 1 cycle, 95° C., 2 minutes; 30 cycles, 95° C., 15 seconds, followed by 55° C., 30 seconds, followed by 68° C., 1 minute. The PCR reaction mixture was run on a 1% agarose gel and the DNA fragment corresponding to the expected size was extracted from the gel using a GE Healthcare illustra GFX™ PCR DNA and Gel Band Purification Kit.

Plasmid pZMP31 is a mammalian expression vector containing an expression cassette having the chimeric CMV enhancer/MPSV promoter, an EcoRI site for linearization prior to yeast recombination, an internal ribosome entry element from poliovirus; an *E. coli* origin of replication and ampicillin selectable marker, a mammalian selectable marker expression unit comprising an SV40 promoter, enhancer and origin of replication, a DHFR gene, and the SV40 terminator, and URA3 and CEN-ARS sequences required for selection and replication in *S. cerevisiae*.

The plasmid pZMP31 was digested with EcoRI prior to recombination in yeast with each of the gel extracted FcγRIA PCR fragments of the short and long version. One hundred μl of competent yeast (*S. cerevisiae*) cells were combined with 20 μl of the FcγRIA short or long insert DNA and ~100 ng of EcoRI digested pZMP31 vector. The mix was transferred to a 0.2 cm electroporation cuvette. The yeast/DNA mixture was electropulsed using power supply (BioRad Laboratories, Hercules, Calif.) settings of 0.75 kV (5 kV/cm), ∞ ohms, and 25 μF. Six hundred μl of 1.2 M sorbitol was added to the cuvette, and the yeast was plated in two 300 μl aliquots onto two URA-D plates and incubated at 30° C. After about 72 hours, the Ura+ yeast transformants from a single plate were resuspended in 800 μl H$_2$O and spun briefly to pellet the yeast cells. The cell pellet was resuspended in 0.5 ml of lysis buffer (2% Triton X-100, 1% SDS, 100 mM NaCl, 10 mM Tris, pH 8.0, 1 mM EDTA). The five hundred μl of the lysis mixture was added to an Eppendorf tube containing 250 μl acid-washed glass beads and 300 μl phenol-chloroform, was vortexed for 3 minutes, and spun for 5 minutes in an Eppendorf centrifuge at maximum speed. Three hundred μl of the aqueous phase was transferred to a fresh tube, and the DNA was precipitated with 600 μl ethanol, followed by centrifugation for 10 minutes at maximum speed. The tube was decanted and the pellet was washed with 1 mL of 70% ethanol, followed by centrifugation for 10 minutes at maximum speed. The tube was decanted and the DNA pellet was resuspended in 10 μl H$_2$O.

Transformation of electrocompetent *E. coli* host cells (DH10B) was done using 1 μl of the yeast DNA preparation and 20 μl of *E. coli* cells. The cells were electropulsed at 2.0 kV, 25 μF, and 400 ohms. Following electroporation, 600 μl SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was added and the cells were plated in 50 μl and 550 μl aliquots on two LB AMP plates (LB broth (Lennox), 1.8% Bacto™ Agar (Difco), 100 mg/L Ampicillin).

The colonies were screened via colony PCR and the inserts of five DNA clones from each construct were subjected to sequence analysis. One clone containing the correct sequence was selected. DNA sequencing was performed using ABI PRISM BigDye Terminator v3.1 Cycle Sequencing Kit (Applied Biosystems, Foster City, Calif.). Sequencing reactions were purified using EdgeBioSystems Preforma Centriflex Gel Filtration Cartridges (Gaithersburg, Md.) and run on an Applied Biosystems 3730 DNA Analyzer (Applied Biosystems, Foster City, Calif.). Resultant sequence data was assembled and edited using Sequencher v4.6 software (GeneCodes Corporation, Ann Arbor, Mich.). One clone containing the correct sequence was selected and large-scale plasmid DNA was isolated using a commercially available kit (QIAGEN Plasmid Mega Kit, Qiagen, Valencia, Calif.) according to manufacturer's instructions.

The sequences of the short and long versions of the insert DNA are shown in SEQ ID NO:31 and SEQ ID NO:33, respectively. The corresponding encoded amino acid sequences for the short and long versions of untagged FcγRIA are shown in SEQ ID NO:32 and SEQ ID NO:34, respectively. The signal sequence for FcγRIA corresponds to amino acids 1-15 of SEQ ID NO:2 (residues 1-15 of SEQ ID NOs 40 and 42), thereby yielding a start site for the mature untagged FcγRIA proteins at position 16 of SEQ ID NOs 32 and 34.

Example 7

Transfection and Expression of Soluble FcγRIA Receptor Expression Constructs that Express Untagged FcγRIA Protein Two hundred μg of the soluble FcγRIA short and long version expression constructs were digested with 200 units of BstB1 at 37° C. for eighteen hours (overnight), washed with phenol/chloroform/isoamyl alcohol, precipitated with ethanol, and centrifuged in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 200 μl of CHO cell tissue culture medium in a sterile environment, allowed to incubate at 37° C. for 30 minutes. Approximately 1×10$^7$ CHO cells were pelleted and were resuspended using the DNA-medium solution. The DNA/cell mixtures were placed in a 0.4 cm gap cuvette and electroporated using the following parameters; 950 μF, high capacitance, at 300 V. The contents of the cuvettes were then removed, pooled, and diluted to 25 mL with CHO cell tissue culture medium and placed in a 125 mL shake flask. The flask was placed in an incubator on a shaker at 37° C., 5% CO$_2$ with shaking at 120 RPM.

The CHO cells were subjected to nutrient selection and amplification to 200 nM Methotrexate (MTX). Tagged protein expression was confirmed by Western blot, and the CHO cell pool was scaled-up for harvests for protein purification.

Example 8

Purification of Untagged FcγRIA

The following method applies to the purification of untagged FcγR1A from CHO DXB11 cell conditioned media.

A. IgG Affinity Chromatography

Undiluted (1×) media were harvested and were loaded over a column containing IgG Sepharose 6 Fast Flow resin (GE Healthcare) at a flow rate of 15 cm/h. For 10 L of conditioned media, a 5 cm diameter column containing 150 mL of packed resin was employed. After loading the media, the column was washed at 100 cm/h with 1.6 mM citric acid, 23 mM dibasic NaPO$_4$, 150 mM NaCl pH 7.0 until the absorbance at 215 nm and A280 nm returned to baseline for at least 2 column volumes (CV). Elution of bound protein was achieved using a 10 CV descending pH gradient of 20 mM citric acid, 5 mM dibasic NaPO$_4$, 0.05% Tween 20, pH 3.0 at a flow rate of 61 cm/h. Fractions containing FcγRIA were identified by SDS-PAGE and Western blotting, were neutralized by the addition of 2 M Tris pH 7.0 to a 0.2 M final concentration and brought to 100 mM NaCl by the addition of 4 M NaCl.

B. Cation Exchange Chromatography

The Tween-20 was removed from the FcγR1A pool by HS50 chromatography. The FcγRIA elution pool was adjusted to 10 mM MES pH 6.0 using solid MES and HCl and was diluted to <5 mS/cm using 10 mM MES pH 6.0. The FcγR1A-containing pool was loaded over an HS50 column to achieve quantitative capture at a flow rate of 141 cm/h and the resin was washed at 382 cm/h with 10 mM MES pH 6.0 until A215 and A280 nm UV signals returned to baseline for at least 5 CV. Bound FcγR1A was eluted at 382 cm/hr with a gradient of increasing NaCl concentration using 5 CV to a maximum of 60% elution buffer which consisted of 10 mM MES, 2 M NaCl pH 6.0. Fractions were collected and FcγRIA was identified by SDS-PAGE and Western blotting.

C. Size Exclusion Chromatography

The amount of protein as assessed by absorbance at 280 nm and the FcγR1A-containing fraction of the buffer-exchanged HS50 elution pool was concentrated using a 30 kD molecular weight cutoff (MWCO) Ultracel centrifugal concentrator or a YM30 63.5 mm stirred cell membrane depending on the amount of FcγR1A present. The final concentrate volume was no more than 3% of the volume of gel filtration column used. The concentrated FcγR1A pool was injected onto a Superdex 75 column (for <1 mg FcγRIA, the column size was 10/300 mm; for 1-10 mg, the column size was 16/60 mm; and for >10 mg, the column size was 26/60 mm) and the protein was eluted isocratically at a flow rate of 34-76 cm/h. The mobile phase used was 35 mM NaPO$_4$, 120 mM NaCl pH 7.2. Fractions were collected and FcγRIA was identified by SDS-PAGE and Western blotting. The FcγRIA-containing fractions were concentrated to 20 mg/mL final concentration as described above, passed through a 0.22 μm sterile-filter, and stored at −80° C. The identity of the FcγRIA was confirmed by N-terminal sequencing and amino acid analyses. N-terminal sequence analysis showed that the mature protein starts with a pyro-glutamic acid, which is post-translationally converted from the glutamine residue at amino acid position 16.

Example 9

Anti-Inflammatory Activities of Soluble FcγRIA

A. Immune Complex Precipitation

Chicken egg ovalbumin (OVA) was dissolved to a final concentration of 15.0 g/mL in phosphate buffered saline (PBS) and combined with 300 μg rabbit polyclonal anti-OVA antibodies/mL in a final volume of 200 μL in the presence and absence of the indicated concentration of soluble FcγRIA. Immediately thereafter, turbidity of the reaction mixture was monitored at 350 nm every 30 seconds for 5-10 min at 37° C. with the aid of a spectrophotometer. Linear regression was used to calculate the slope of the linear portion of the turbidity curves and the FcγR-mediated inhibition of immune complex precipitation was expressed relative to incubations containing anti-OVA and OVA alone.

B. Cytokine Secretion from Mast Cells

Immune complexes were prepared by mixing 300 uL of rabbit polyclonal anti-OVA with 75.0 μL of 1 mg OVA/mL in PBS in a final volume of 5.0 mL of PBS. After incubation at 37° C. for 30-60', the mixture was placed at 4° C. for 18-20 h. The immune complexes were collected by centrifugation at 12,000 rpm for 5.0 min, the supernatant fraction was removed and discarded, and the immune complex precipitate was resuspended 1.0 mL of ice cold PBS. After another wash, the immune complexes were resuspended in a final volume of 1.0 mL ice cold PBS. Protein concentration was determined using the BCA assay.

MC/9 cells were sub-cultured in Medium A (DMEM containing 10% fetal bovine serum, 50.0 μM B-mercaptoethanol, 0.1 mM non-essential amino acids, 1.0 mM sodium pyruvate, 36.0 μg/mL L-asparagine, 1.0 ng/mL rmIL-3, 5.0 ng/mL rmIL-4, 25.0 ng/mL rmSCF) to a density of 0.5–3×10$^6$ cells/mL. Cells were collected by centrifugation at 1500 rpm for 5.0 min and the cell pellet was washed in Medium A (without cytokines) and resuspended in Medium A at 2.0×10$^6$ cells/mL. Aliquots of cells (2.0×10$^5$ cells) were incubated with 10.0 μg/well of OVA/anti-OVA immune complexes (IC's) in a final volume of 200 μL of Buffer A in a 96-well microtiter plate. After 4.0 h at 37° C., the media was removed and centrifuged at 1500 rpm for 5.0 min. The cell-free supernatant fractions were collected and aliquots were analyzed for the presence of IL-6, IL-13, TNFα, and MCP-1 cytokine release using a Luminex cytokine assay kit.

C. Complement-Mediated Lysis of SRBCs

Antibody-sensitized SRBCs (Sigma-Aldrich, St. Louis, Mo.) were prepared and were incubated with different concentrations of soluble FcγRIA. After 15 minutes at 4° C., a 25 μL sample of a 1:50 dilution of rat serum (Sigma-Aldrich, St. Louis, Mo.) was added, and hemolysis was measured by monitoring the absorbance of the mixture at 540 nm as described by the manufacturer.

D. Measurement of FcγRIA-CH6 Affinity for Human IgG1

The IgG1 antibody was immobilized to a single flow cell, utilizing a second non-derivatized cell as the blank reference. Immobilization of the IgG1 antibody was performed using an amine coupling kit (Biacore) and the standard Wizard Template for Surface Preparation, operated by the Biacore Control Software. Based on Wizard results for a pH scouting study, the IgG1 antibody solution was diluted to 11 μg/mL in sodium acetate, pH 5.0. The Wizard Template for amine coupling was used to immobilize the antibody to a single flow cell. The carboxyl groups on the sensor surfaces were then activated with an injection of a solution containing 0.2 M N-ethyl-N'-(3-diethylamino-propyl) carbodiimide (EDC) and 0.05 M N-hydroxysuccinimide (NHS). The antibody solution was then injected over the activated surface targeting a level of 150-200 RU. The immobilization procedure was completed by blocking remaining ester sites on the carboxymethyl dextran surface with 1 M ethanolamine hydrochloride.

The method for injection of the analyte solutions (FcγRIA-CH6) was written using the Biacore Wizard Template for kinetic analysis. The method was run at 25° C. and the samples stored in the autosampler at ambient temperature. It is noted that in using the Wizard Template, certain parameters optimal for kinetics, such as injection modes, are pre-defined by the Wizard program.

The method for analysis of FcγRIA was optimized for determination of kinetic rate constants, $k_a$ and $k_d$. The receptor was injected over both flow cells (i.e., 1 and 2, blank and antibody-derivatized, respectively) in series to allow for comparative analysis of binding of the FcγRIA to the human IgG1 antibody vs. binding of the FcγRIA to the non-modified control surface (binding to rabbit anti-OVA IgG not tested). The analyte was injected at a flow rate of 40 μL/min for 3 minutes (association time). The dissociation time for each analyte injection was 3 minutes. The analyte dose response curve range was 0.16-10.3 nM. For each dose response curve point, N=2 replicate injections were run. The sequence included injections of buffer for subtraction of instrument noise and drift. Dose response curve samples were injected in random mode. For kinetic analysis of FcγRIA, each dose response curve cycle was followed by a single 30 second injection of glycine, pH 1.75 at 50 μL/minute to regenerate the IgG antibody surface.

Data analysis was performed using Biacore Control, Evaluation and Simulation software. Baseline stability was first assessed to ensure that the regeneration step provided a consistent binding surface throughout the sequence of injections. The level of non-specific binding of the FcγRIA analyte to the control surface was checked and confirmed to be minimal. Binding curves were processed by subtraction of the control surface curve (i.e., flow cell 1) from the specific binding surface curve (i.e., flow cell 2), as well as subtraction of instrument noise and drift using a buffer injection curve. The data was checked for reproducibility of analyte injections and the resulting corrected binding curves were then globally fitted to binding models and the resulting fit and equilibrium constants evaluated.

E. Cutaneous Reverse Passive Arthus Reaction in Mice

Ten-week old female C57BL/6 mice (n=8 mice per group) were anesthetized with isoflurane, their dorsal skin was shaved, and the back of each mouse was wiped with 70% alcohol. Each mouse received two intradermal injections of 0.02 mL each, at distinct sites in the dorsal skin. The injection solutions contained phosphate buffered saline (PBS) and either 40.0 µg of rabbit anti-ovalbumin (anti-OVA, heat-inactivated by incubation at 56° C. for 30-40 min) alone or 40.0 µg of anti-OVA and the indicated amount of FcγRIA-CH6. Mice in the control groups received two intradermal injections of 40.0 µg non-immune rabbit IgG (heat-inactivated as described above). Antibody preparations were centrifuged at 14,000 rpm for 10 min to remove particulates prior to injection. Immediately following the intradermal injections, each mouse was injected in the tail vein with 100.0 µL of a solution containing 10.0 mg OVA/mL and 10.0 mg Evan's Blue/mL. In some instances, the tail vein injection solution also contained dexamethazone at a dose of 1.0 mg/kg. Four hours after the injections, the mice were euthanized by $CO_2$ gas. Cutaneous edema was evaluated by measuring the area of vascular leak of Evan's Blue dye ($mm^2$) and by measuring tissue weights (mg) of punch biopsies taken from the lesion sites. The tissue samples were then quickly frozen in liquid $N_2$ and stored at −80° C.

Neutrophil infiltration was assessed by measuring myeloperoxidase activity in the punch biopsy samples as described (Bradley et al., *J. Invest. Dermatol.* 78:206-209, 1982) using the Myeloperoxidase Assay Kit from Cytostore (Calgary, Alberta Canada).

Systemic administration of FcγRIA-CH6 in mice was performed by intravenous injection of either vehicle alone or vehicle containing the indicated concentrations of FcγRIA-CH6. Each mouse received the indicated dose of FcγRIA-CH6 in a 0.1 mL final volume of formulation buffer (35 mM sodium phosphate, 120 mM NaCl, pH 7.2) 1.0-h prior to initiating the Arthus reaction. The cutaneous Arthus reaction in mice was performed exactly as described above.

F. Results and Discussion

To evaluate whether FcγRIA-CH6 could block immune complex precipitation, an anti-OVA/OVA immune complex precipitation assay was established based on the methods of MØller (*Immunology* 38:631-640, 1979) and Gavin et al. (*Clin. Exp. Immunol.* 102:620-625, 1995). Incubation of anti-OVA and OVA at 37° C. produced a time-dependent increase in optical density of the solution mixture (FIG. 1, circles), an observation consistent with the formation of insoluble anti-OVA/OVA immune complexes. Addition of FcγRIA-CH6 at the start of the assay produced a dose-dependent reduction in immune complex precipitation (FIG. 1, triangles and squares). Immune complex precipitation was completely abolished by 1500 nM FcγRIA-CH6. Identical data were obtained when untagged, recombinant soluble FcγRIA was used. Since the precipitation of antigen:antibody immune complexes appears to be dependent on non-covalent interactions between the antibody Fc heavy chains (MØller, *Immunology* 38:631-640) and Fcγ receptors bind to the Fc portion of antibodies (Dijstelbloem H M et al., *Trends Immunol.* 22:510-516, 2001), these data suggest that soluble FcγRIA disrupts immune complex precipitation by binding to the Fc portion of the anti-OVA antibodies.

To directly evaluate the interaction of FcγRA-CH6 with antibody Fc, the binding of FcγRIA-CH6 to immobilized human IgG1 was assessed by surface plasmon resonance analyses. A monoclonal human IgG1 antibody was immobilized to the sensor surface in a single flow cell at an RU (resonance units) level of 485, a density level within optimal levels for kinetic analysis of FcγRIA-CH6, presuming a binding stoichiometry of one FcγRIA molecule with one IgG1 molecule (Woof and Burton, *Nature Rev. Immunol.* 4:1-11, 2004). FcγRIA rapidly bound to immobilized IgG1 with rates of association and dissociation of $2.8 \times 10^6$ $M^{-1}s^{-1}$ and $4.6 \times 10^{-4}$ $s^{-1}$, respectively, values which yield a calculated equilibrium dissociation constant of $1.7 \times 10^{-10}$ M. These data are similar to those reported previously (Paetz A et al., *Biochem. Biophys. Res. Commun.* 338:1811-1817, 2005) and demonstrate that FcγRIA-CH6 binds with high affinity to human IgG1.

Mast cells are thought to mediate immune complex-mediated inflammation in a variety of immune disorders such as type II hypersensitivity reactions (Ravetch, *J. Clin. Invest.* 110:1759-1761, 2002; Sylvestre and Ravetch, *Immunity* 5:387-390, 1996; Jancar and Crespo, *Trends Immunology* 26:48-55, 2005). Binding of immune complexes to mast cell Fcγ receptors is thought to induce the secretion of pro-inflammatory cytokines, such as IL-6 and TNFα (Ravetch, supra; Jancar and Crespo, supra), which subsequently leads to neutrophil infiltration and tissue damage. To evaluate whether cytokine secretion from mast cells could be stimulated by immune complexes, the murine mast cell line MC/9 was incubated in the presence and absence of preformed rabbit anti-OVA/OVA immune complexes. Incubation with anti-OVA/OVA immune complexes produced a time and concentration dependent increase in the accumulation of the inflammatory cytokines IL-6, IL-13, TNFα, and MCP-1 within the MC/9 cell conditioned media. Cytokine production was not altered, in contrast, when MC/9 cells were incubated with an equivalent concentration of rabbit anti-OVA IgG alone. These data demonstrate that MC/9 cells respond to immune complexes by the production of inflammatory cytokines.

Figure 2A:
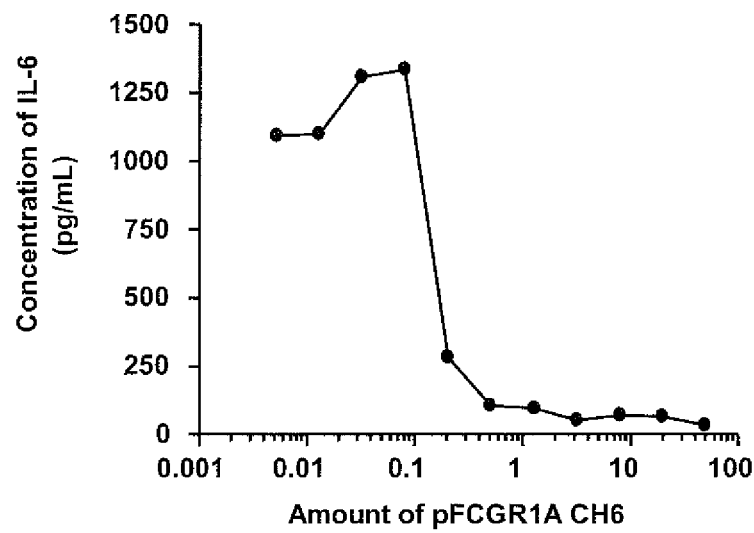
FIGS. 2A-2D depict inhibition of immune complex-mediated production of inflammatory cytokines in mast cells with FcγRIA-CH6. Murine MC/9 mast cells were incubated with anti-OVA/OVA immune complexes in the presence of increasing amounts of FcγRIA-CH6 ("pFCGR1A CH6") and secretion of inflammatory cytokines were determined as described in Example 9, infra. Each point represents the mean value of duplicate determinations and is representative of two separate experiments.
Figure 2B:
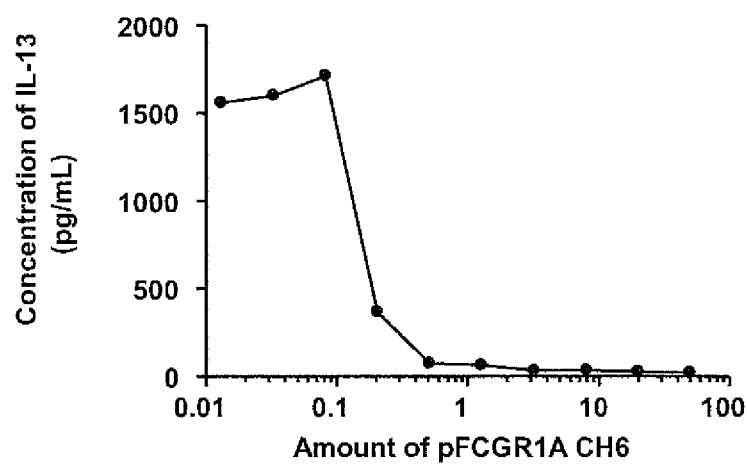
Figure 2C:
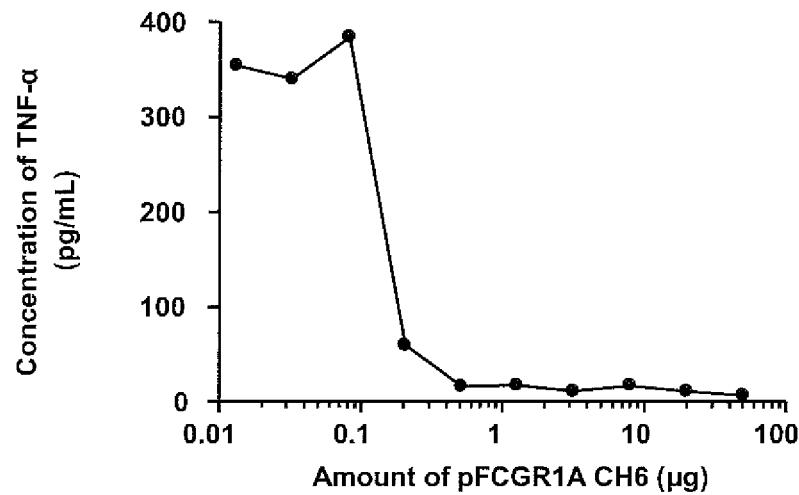
Figure 2D:
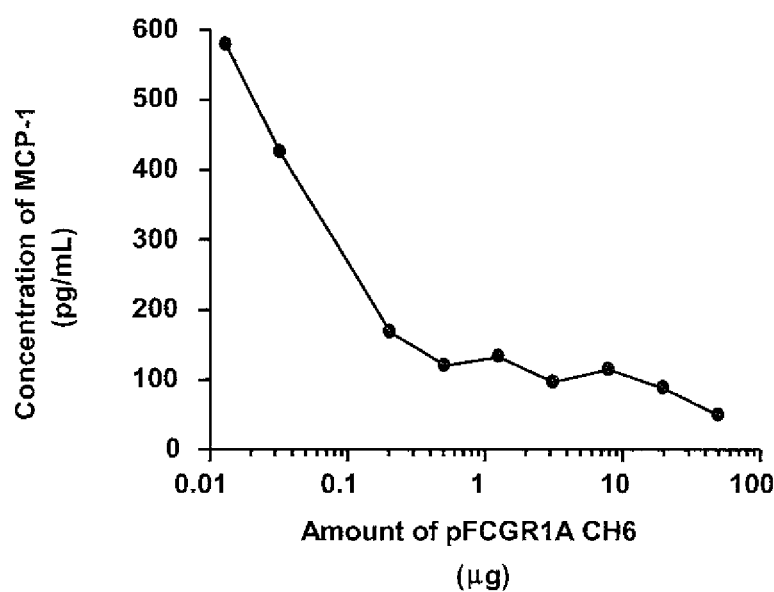

Incubation of MC/9 cells with anti-OVA/OVA immune complexes in the presence of increasing amounts of FcγRIA-CH6 produced dose-dependent reductions in the accumulation of IL-6 (FIG. 2A), IL-13 (FIG. 2B), TNFα (FIG. 2C) and MCP-1 (FIG. 2D). Identical data were obtained when untagged, recombinant soluble FcγRIA was used. These data demonstrate that soluble FcγRIA can block the binding and signalling of immune complexes in mouse mast cells.

Soluble FcγRIA was also evaluated for its effect on complement-mediated lysis of antibody-sensitized SRBCs. Incubation of antibody-sensitized SRBCs with rat serum at 37° C. resulted in complement activation and lysis of the SRBCs. Addition of FcγRIA-CH6 to the incubation mixtures blocked SRBC lysis in a dose-dependent manner. Little or no inhibition of hemolysis was observed, in contrast, with an unrelated control protein, TACI-Ig.

The findings described above demonstrate that FcγRIA-CH6 can block the formation of immune complexes in vitro, can inhibit immune complex-mediated signalling in mast cells, and can block IgG-mediated complement activity. These data suggest that FcγRIA-CH6 may be effective at blocking IgG- or immune complex-mediated inflammation in an in vivo setting. To test this, the cutaneous reversed passive Arthus reaction was established in mice and the effects of FcγRIA-CH6 on immune complex-mediated edema and neutrophil infiltration were assessed.

Figure 3A:
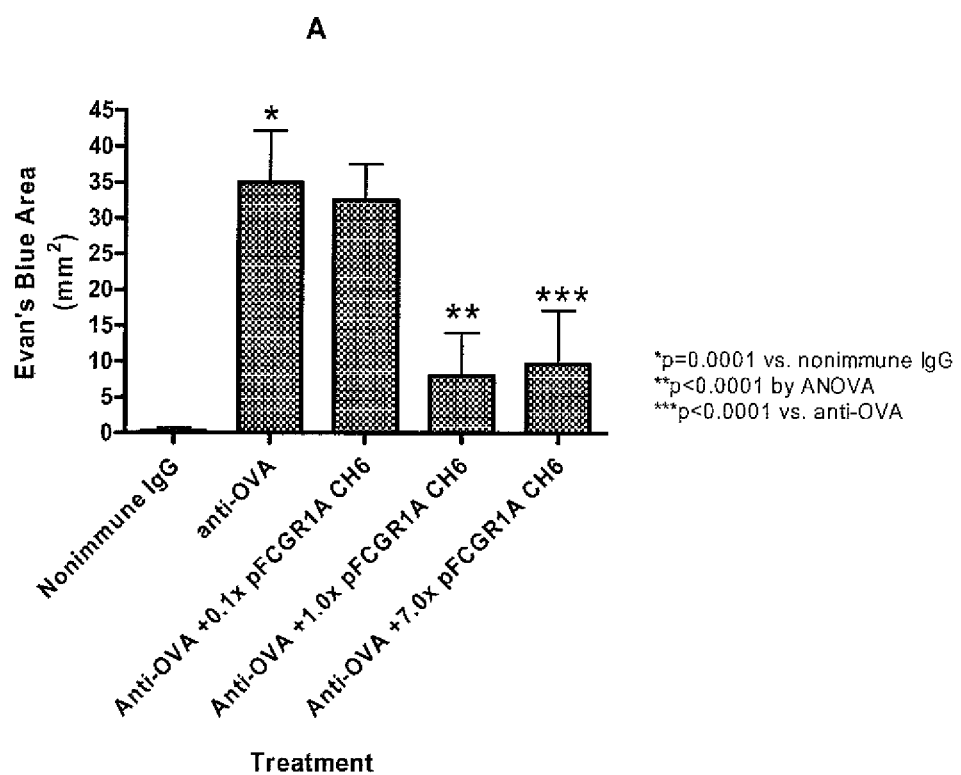
FIGS. 3A-3C depict inhibition of immune complex-mediated edema and neutrophil infiltration in the murine Arthus reaction with FcγRIA-CH6. The cutaneous reversed passive Arthus reaction was established in mice using intradermal delivery of rabbit anti-ovalbumin and tail vein injection of ovalbumin. (See Example 9, infra.) Animals received either anti-OVA alone or anti-OVA together with the indicated amount of FcγRIA-CH6 ("pFCGRIA CH6"), and the effects of FcγRIA-CH6 on immune complex-mediated edema and neutrophil infiltration were assessed. (See id.) Each bar represents the mean±SD for n=8 animals per group. 0.1×, 1.0×, and 7.0×pFCGRIA-CH6 represents the molar excess of FcγRIA-CH6 added relative to the amount of anti-OVA injected and is equivalent to 1.3 μg, 13.0 μg, and 91.0 μg of with FcγRIA-CH6, respectively.
Figure 3B:
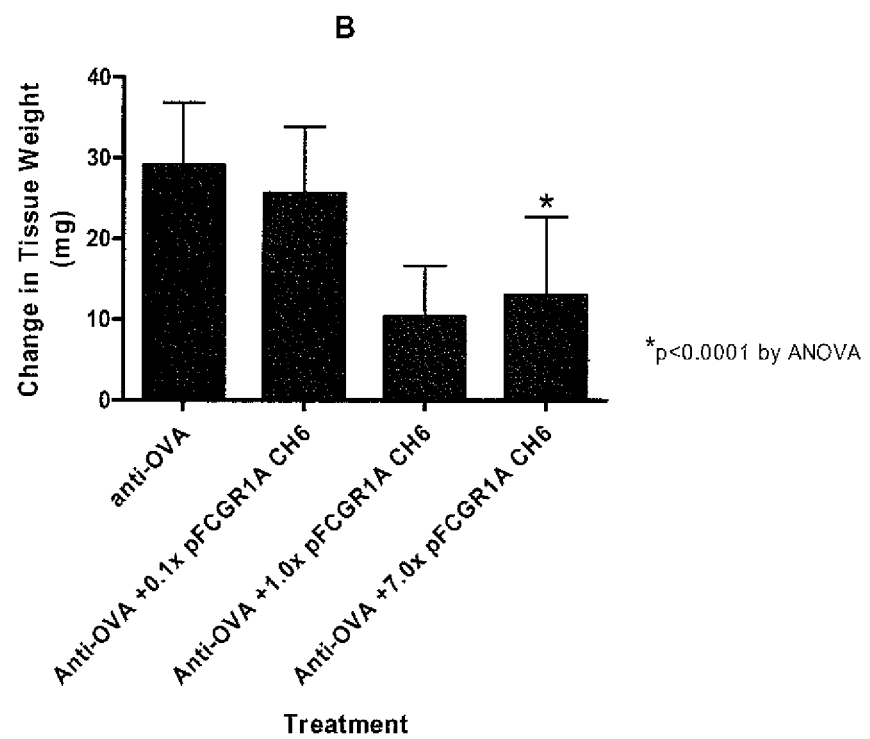
Figure 3C:
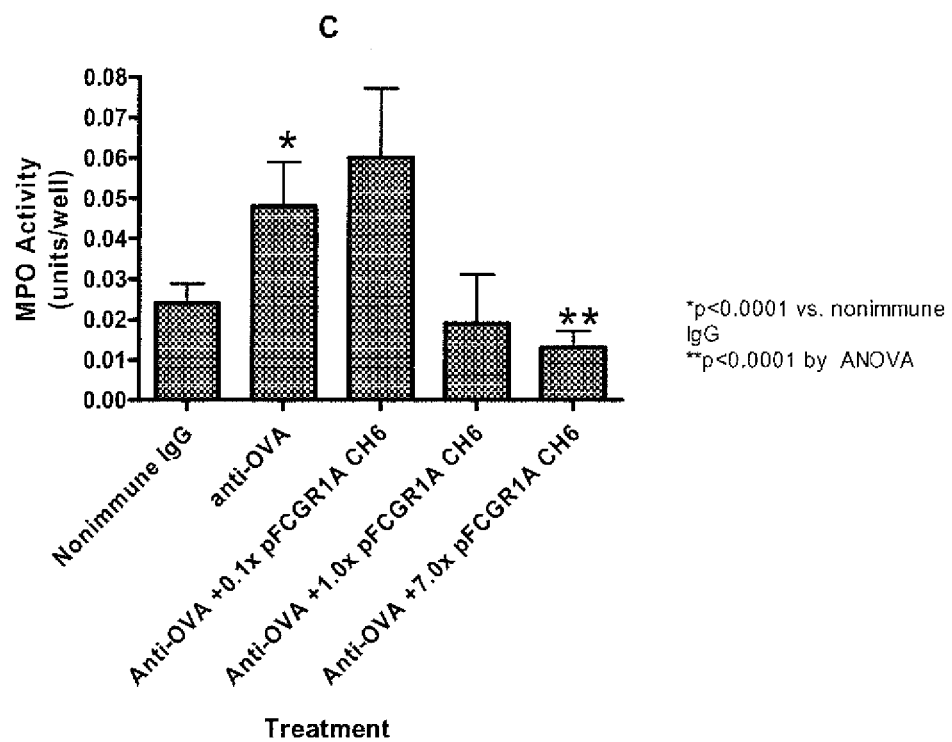

Relative to intradermal injection of an equivalent concentration of nonimmune IgG, injection of anti-OVA antibodies produced a time and concentration increase in edema within the skin of treated mice. Edema was evident as both an increase in the area of extravasation of Evan's blue dye (FIG. 3A) and in tissue weights (FIG. 3B). These effects were specific for immune complexes as no edema was observed in the absence of tail vein injection of OVA. Accumulation of neutrophils within the lesion site, measured by extractable activity of myeloperoxidase, was also increased (FIG. 3C).

Intradermal delivery of anti-OVA antibodies with increasing amounts of FcγRIA-CH6 produced a concentration-dependent reduction in edema, measured by either a decrease in Evan's blue area (FIG. 3A) or a decrease in tissue weight of the lesion site (FIG. 3B). Myeloperoxidase activity in the lesion biopsies was also significantly decreased by FcγRIA-CH6 (FIG. 3C). These data demonstrate that FcγRIA-CH6 was an effective inhibitor of immune complex-induced inflammation in the Arthus reaction in mice.

These data demonstrate that local delivery of FcγRIA-CH6 can block immune complex-mediated dermal inflammation in the Arthus reaction in mice.

Figure 4:
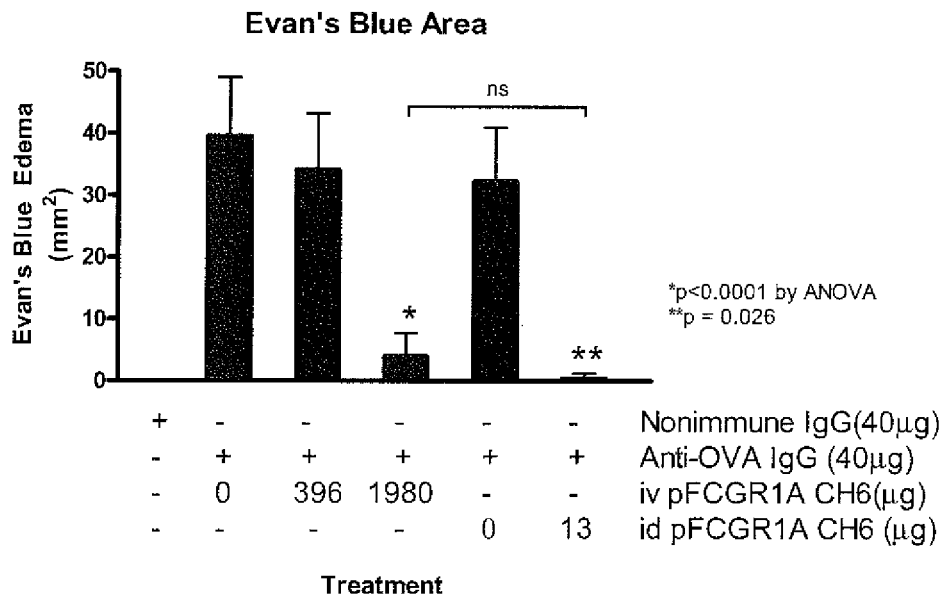
FIG. 4 depicts inhibition of inflammation in the Arthus reaction in mice with systemic delivery of FcγRIA-CH6. Mice were injected with the indicated amounts of either vehicle alone or vehicle containing the indicated amount of FcγRIA-CH6 ("pFCGRIA CH6") 1 hour prior to initiating the Arthus reaction. (See Example 9, infra.) Systemic administration of FcγRIA-CH6 was performed by intravenous injection, and the cutaneous reversed passive Arthus reaction was carried out using intradermal delivery of rabbit anti-ovalbumin, as described in Example 9. Edema was measured by anti-OVA induced extravasation of Evan's Blue dye. Each bar represents the mean±SD for n=8 mice (intravenous injection of FcγRIA-CH6) or n=4 mice (intradermal injection of FcγRIA-CH6). The abbreviations used are: iv=intravenous; id=intradermal.
Figure 5:
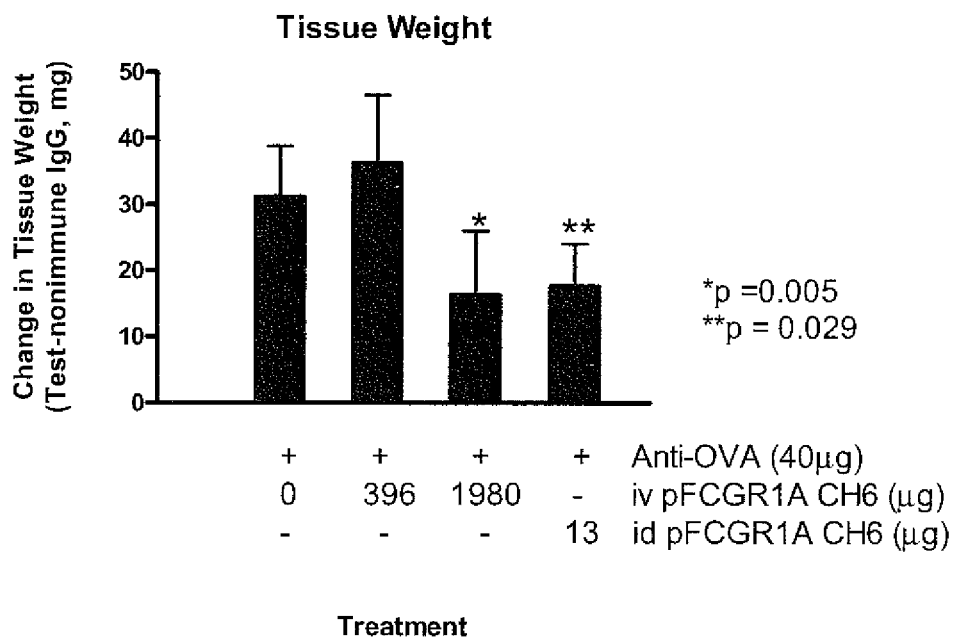
FIG. 5 depicts inhibition of edema in the Arthus reaction in mice with systemic delivery of FcγRIA-CH6. Mice were injected with the indicated amounts of either vehicle alone or vehicle containing the indicated amount of FcγRIA-CH6 ("pFCGRIA CH6") 1 hour prior to initiating the Arthus reaction. (See Example 9, infra.) Systemic administration of FcγRIA-CH6 was performed by intravenous injection, and the cutaneous reversed passive Arthus reaction was carried out using intradermal delivery of rabbit anti-ovalbumin, as described in Example 9. Edema was measured by anti-OVA induced increases in tissue weights of the lesion sites. Each bar represents the mean±SD for n=8 mice (intravenous injection of FcγRIA-CH6) or n=4 mice (intradermal injection of FcγRIA-CH6). The data are expressed relative to injection of nonimmune IgG. The abbreviations used are: iv=intravenous; id=intradermal.

To evaluate whether systemic delivery of FcγRIA-CH6 could reduce cutaneous inflammation, mice were injected with FcγRIA-CH6 via the tail vein, 1.0-h prior to initiating the Arthus reaction. Compared to injection with vehicle alone, injection with FcγRIA-CH6 produced dose-dependent reductions in edema, measured either by the anti-OVA induced extravasation of Evan's Blue dye (FIG. 4) or by the anti-OVA induced increases in tissue weights of the lesion sites (FIG. 5). With the highest dose of FcγRIA-CH6, edema was virtually abolished (FIGS. 4 and 5). Similar to the data described above, intradermal delivery of 13.0 µg of FcγRIA-CH6 also reduced edema in this model (FIGS. 4 and 5). The reduction in edema seen with the highest dose of FcγRIA-CH6 given by the intravenous route was similar to that observed with intradermal delivery of 13.0 µg of FcγRIA-CH6 (FIGS. 4 and 5). Accumulation of neutrophils within the lesion sites, measured by extractable myeloperoxidase activity was also abolished in animals treated with FcγRIA-CH6.

Example 10

Comparison of the Anti-Inflammatory Activities of Recombinant Human FcγRIA, FcγRIIA, and FcγRIIIA In addition to the evaluation of monomeric FcγRIA-CH6 for anti-inflammatory activities (see Example 9, supra), monomeric FcγRIIA-CH6 and FcγRIIIA-CH6 (prepared as described above in Example 4) were also tested using the same in vitro and in vivo assays described in Example 9. Soluble FcγRIIA-CH6 and FcγRIIIA-CH6 were tested in parallel with FcγRIA-CH6 for their effects on immune complex precipitation, cytokine secretion from mast cells, and IgG-mediated complement activity. Similar to FcγRIA-CH6, both FcγRIIA-CH6 and FcγRIIIA-CH6 reduced immune complex precipitation, blocked complement-mediated lysis of antibody-sensitized red blood cells, and inhibited immune complex-mediated accumulations of IL-6, IL-13, MCP-1 and TNF-α in mast cell-conditioned media. The relative order of potency with respect to the reduction in immune complex precipitation was FcγRIIIA>FcγRIA>FcγRIIA, with maximal inhibition seen using 1-1.5 µM for each soluble FcγR, a molar ratio of FcγR:anti-OVA of approximately 1:1. The relative order of potency for both the blockade of complement-mediated lysis and inhibition of mast cell cytokine secretion was FcγRIA>FcγRIIIA>FcγRIIA. With respect to inhibition of cytokine secrection, for each soluble FcγR, the $IC_{50}$s were similar for each cytokine examined.

FcγRIIA-CH6 and FcγRIIIA-CH6 were also tested in parallel with FcγRIA-CH6 for their effects in vivo on edema and neutrophil infiltration in the cutaneous Arthus reaction in mice. In contrast to the reduction in inflammation observed with soluble FcγRIA-CH6, neither FcγRIIIA-CH6 nor FcγRIIA-CH6, used over a similar concentration range, reduced anti-OVA induced extravasation of Evan's blue dye, tissue weight, or tissue MPO activity (see FIG. 6, A-C).

Dimeric Fc5 fusion protein versions of FcγRIIA and FcγRIIIA, each containing two molecules of the extracellular domains of FcγRIIA or FcγRIIIA fused to an effector negative version of human Fc (Fc5), were also prepared and tested in the assays described above. The nucleotide and encoded amino acid sequences for FcγRIIA-Fc5 are shown in SEQ ID NO:35 and SEQ ID NO:36, respectively, while the nucleotide and encoded amino acid sequences for FcRIIA-Fc5 are shown in SEQ ID NO:37 and SEQ ID NO:38, respectively. N-terminal sequence analysis showed Gln-34 as the start site for mature FcγRIIA-Fc5 and Met-18 and Glu-21 as the start site for mature FcγRIA-Fc5. Each of the dimeric Fc5 fusion proteins had activities similar to the monomeric versions of each protein in all of the in vitro assays described above. Similar to their monomeric counterparts, and again in contrast to FcγRIA-CH6, neither FcγRIIA-Fc5 nor FcγRIIIA-Fc5 reduced inflammation or neutrophil infiltration in the reverse passive Arthus reaction in mice.

Example 11

Collagen Antibody-Induced Model of Arthritis

Male DBA/1 J mice (8 weeks old, n=8 mice per group) were administered 2 mg (in 200 uL) of the anti-Type II collagen antibody cocktail (Chemicon Intl. Arthrogen-CIA®) via intravenous tail injection on Day 0. The amount of mAb cocktail injected was based on literature values and on data from preliminary studies where 2.0 mg doses of Arthrogen-CIA® gave clear and consistent symptoms of arthritis in male DBA/1 mice. Three days later, mice received sub-cutaneous injections of either vehicle alone (PBS) or vehicle containing the indicated concentration (0, 0.67, or 2.0 mg) of FcγRIA-CH6. Three and one-half hours later, all mice received an intraperitoneal injection of 50 ug of LPS dissolved in a final volume of 50 uL of PBS, as provided in the Arthrogen kit. Mice were treated with vehicle or the indicated concentration of FcγRIA-CH6 every other day for a total of five doses.

Mice were scored (visual scores and caliper paw measurements) for arthritis on a daily basis starting on day 0, prior to injection of the Arthrogen-CIA® antibody cocktail.

Mice were be sacrificed on day 11. Serum was collected and frozen at −80 C. Paws were collected into 10% NBF, and processed for histology.

Figure 7:
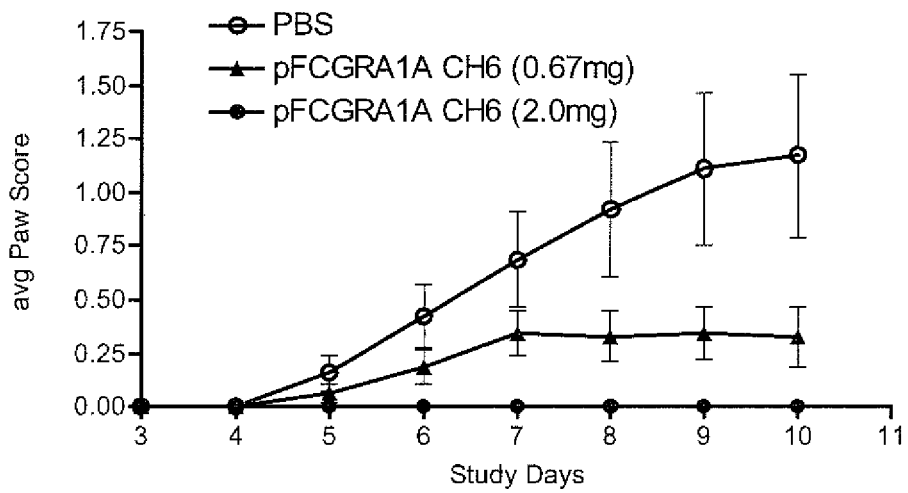
FIG. 7 depicts reduction of paw scores in the collagen antibody-induced arthritis mouse model with Fc RIA-CH6. Collagen antibody-induced arthritis was established in mice by treatment with the Arthrogen-CIA® antibody cocktail, as described in Example 11, infra. Mice also received either sub-cutaneous injections of either vehicle alone (PBS) or vehicle containing the indicated concentration of FcγRIA- CH6 ("pFCGRIA CH6"), every other day for a total of five doses. Each point represents the mean±SEM for n=8 mice per group. Differences between groups were significant by repeated measures ANOVA.
Figure 8:
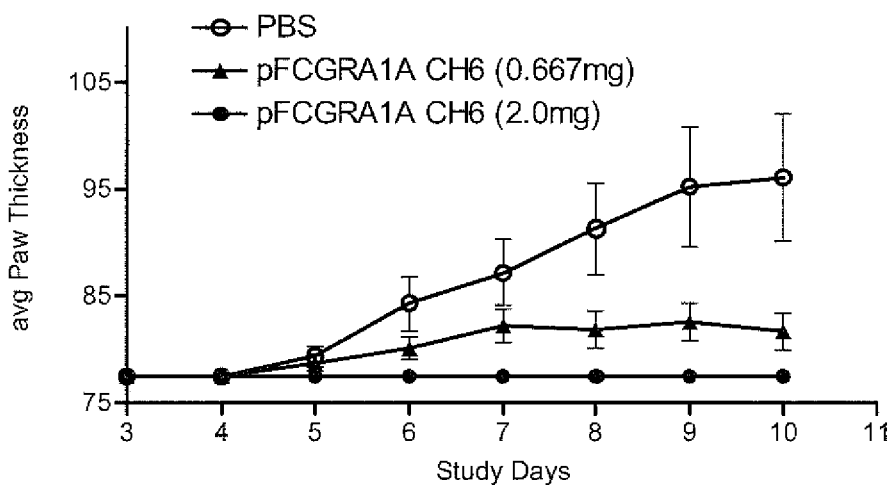
FIG. 8 depicts reduction of paw thickness in the collagen antibody-induced arthritis mouse model with FcγRIA-CH6. Collagen antibody-induced arthritis was established in mice by treatment with the Arthrogen-CIA® antibody cocktail, as described in Example 11, infra. Mice also received either sub-cutaneous injections of either vehicle alone (PBS) or vehicle containing the indicated concentration of FcγRIA-CH6 ("pFCGRIA CH6"), every other day for a total of five doses. Each point represents the mean±SEM for n=8 mice per group. Differences between groups were significant by repeated measures ANOVA.
Figure 9A:
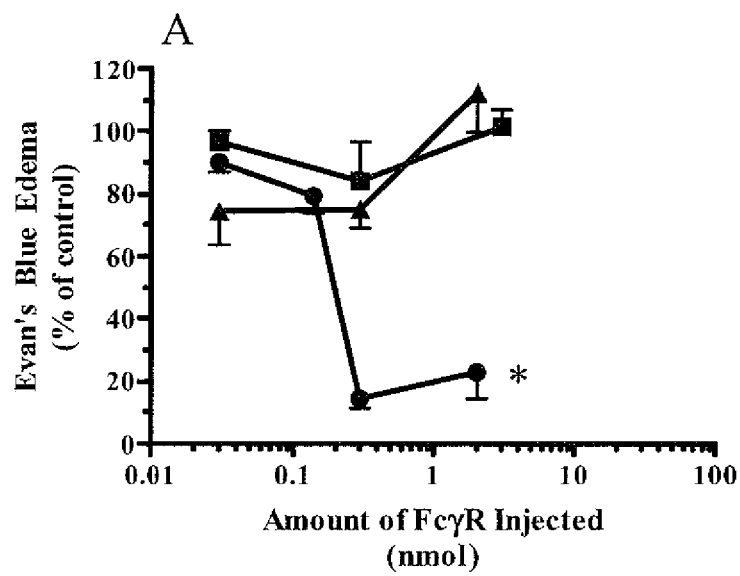
FIGS. 9A-9C depict reduction in inflammation in the Arthus reaction by FcγRIA-CH6 but by neither FcγRIIA-CH6 nor FcγRIIIA-CH6. Experiments were carried out as described in Examples 9 and 10, infra. The data are expressed relative to that observed in the presence of anti-OVA alone after subtracting the values for non-immune IgG from each point. Each point, FcγRIA (●), FcγRIIA (▲), FcγRIIIA (■), represents the mean±SEM for n=8-16 lesion sites (FIGS. 9A and 9B) and for n=5-13 lesion sites (FIG. 9C) from six separate experiments. Differences were significant, *p<0.0001 across all dose groups by ANOVA.
Figure 9B:
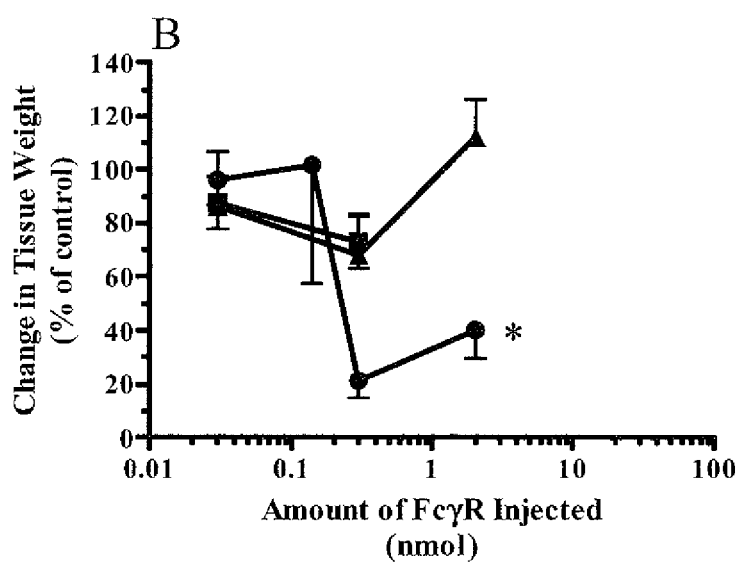
Figure 9C:
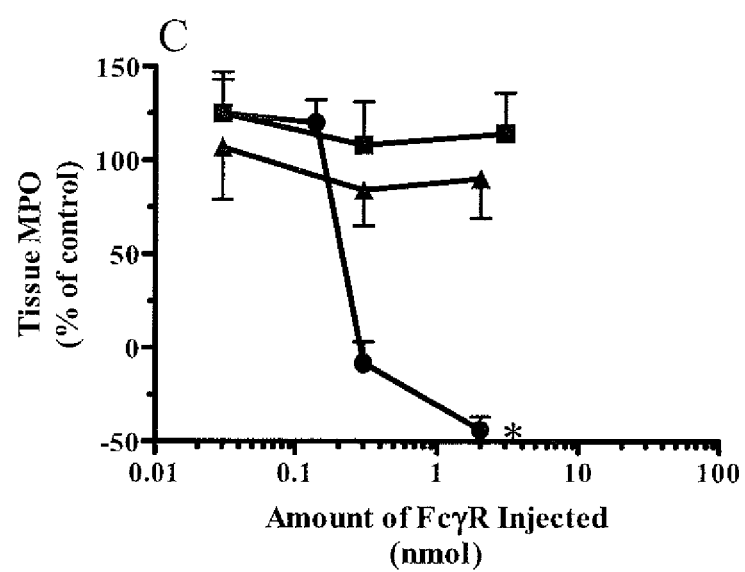

Treatment of mice with the Arthrogen-CIA® antibody cocktail, produced a time-dependent increase in paw inflammation, measured by either the visual paw score (FIG. 7, PBS treated) or by paw thickness (FIG. 8, PBS treated). The increase in arthritis score is easily observed in animals treated with vehicle alone (PBS). Treatment of animals with FcγRIA-CH6 produced a concentration-dependent reduction in paw inflammation. Antibody-induced inflammation, evident as the visual paw score (FIG. 7) or paw thickness (FIG. 8), was completely abolished by the highest dose of FcγRIA-CH6 administered. A less robust reduction in these parameters was seen with the 0.67 mg dose of FcγRIA-CH6 administered. These data demonstrate that FcγRIA-CH6 has potent anti-inflammatory properties in a setting of arthritis.

Example 12

Treatment of Cryoglobulinemia with Soluble Hybrid FcγR in TSLP Transgenic Mice

Mice over-expressing thymic stromal lymphopoietin (TSLP), an interleukin-7 (IL-7)-like cytokine with B-cell promoting properties, produce large amounts of circulating cryoglobulins of mixed IgG-IgM composition. (See Taneda et al., *Am J. Pathol.* 159:2355-2369, 2001.) Development of mixed cryoglobulinemia in these animals is associated with systemic inflammatory disease involving kidneys, liver, lungs, spleen, and skin (see id.) due to immune complex deposition in these tissues. Kidney disease in these animals closely resembles human cryoglobulinemia glomerulonephritis as seen in patients with HCV infection. A role for Fcγ receptors in the disease process was shown by the exacerbation of renal injury with accelerated morbidity and mortality after deletion of the inhibitory receptor Fcγ receptor IIb (see Muhlfeld et al., *Am. J. Pathol.* 163:1127-1136, 2003). In view of these data, the studies described herein, demonstrating efficacy of soluble FcγRIA against immune-complex-mediated inflammation, suggest that TSLP-transgenic mice are a suitable model for evaluating efficacy of soluble FcγRIA or soluble hybrid FcγR as described herein for treating cryoglobulinemia.

Groups of ten TSLP-transgenic mice (three to six weeks of age) are treated with either vehicle alone, or vehicle containing 0.1, 0.3, 0.9, or 2.0 mg of soluble hybrid Fcγ receptor by subcutaneous injections. Animals are dosed with either vehicle or vehicle with soluble hybrid FcγR by a variety of dosing schedules (e.g., every other day over 21 days or every fourth day over 21 days).

At 21 days following dosing, a urine sample is collected for measurement of albuminuria, the animals are anesthesized with halothane, and blood is drawn by cardiac puncture. Spleen, kidneys, liver, ears, and lungs are removed and routinely processed for histology. For all organs, 4 μm sections from formalin-fixed and paraffin-embedded tissue are stained with hematoxylin and eosin (H&E) following routine protocols. From the kidney, 2 μm sections are stained with H&E, periodic acid Schiff reagent (PAS), and periodic acid methenamine silver stain.

Blood urea nitrogen is measured using a standard clinical chemistry analyzer and serum stored at 4° C. is assessed for the presence of cryoglobulins by visual inspection. Urine albumin to creatinine ratio is calculated to evaluate albuminuria by standard procedures.

Morphometry is performed on H&E-stained and silver-stained slides and kidney damage is assessed by measuring the number of glomerular nuclei and the glomerular tuft area on H&E stained slides, the area of glomerular matrix and glomerular tuft area on silver-stained slides, and the area of glomerular MAC-2 positive staining for macrophages and the glomerular tuft area. Results are expressed as the cell number per glomerulus, the cell number per glomerular tuft area, the matrix area of each glomerulus, the percentage of matrix, the area of macrophages per glomerulus, and the area of macrophages per glomerular area.

Efficacy of soluble hybrid FcγR are measured as decreases in the glomerular tuft area, mean glomerular areas occupied by macrophages, and mean cell numbers per glomerulus, and by decreases in matrix area, compared to wild-type controls.

Example 13

FcγRIA Decreases Disease Incidence and Progression in Mouse Collagen Induced Arthritis (CIA) Model A. Mouse Collagen Induced Arthritis (CIA) Model The CIA model of arthritis is an appropriate and well-regarded model to evaluate therapeutic potential of drugs to treat human arthritis. Arthritis is a disease that is characterized by inflammation and/or inappropriate immune complex formation with the joints. The immune complexes are often composed of antibodies directed against type II collagen, an important hyaline cartilage matrix protein. Formation of immune complexes within the joint leads to the recruitment of immune cells to the joint space and the generation of inflammatory cytokines that lead to cartilage and bone destruction within the affected joint. Collagen induced arthritis in mice thus shares many biochemical, cellular, and structural similarities with rheumatoid arthritis in humans.

Eight to ten-week old male DBA/1 J mice (25-30 g) were used for these studies. On day −21, animals were given an intra-dermal tail injection of 0.1 mL of 1 mg/ml chick Type II collagen formulated in Complete Freund's Adjuvant (prepared by Chondrex Inc., Redmond, Wash.). Three weeks later, on Day 0, mice were given the same injection except prepared in Incomplete Freund's Adjuvant. Animals began to show symptoms of arthritis following the second collagen injection, with most animals developing inflammation within 1 to 2 weeks. The extent of disease was evaluated in each paw by using a caliper to measure paw thickness, and by assigning a clinical score (0-3) to each paw (see description below for disease scoring).

B. Monitoring Disease

Incidence of disease in this model was 95-100% with only a few (0-2) non-responders (determined after 6 weeks of observation). Animals are considered to have established disease only after marked, persistent paw swelling has developed. All animals were observed daily to assess the status of the disease in their paws, which was done by assigning a qualitative clinical score to each of the paws. Every day, each animal had its 4 paws scored according to its state of clinical disease. To determine the clinical score, the paw is thought of as having 3 zones, the toes, the paw itself (manus or pes), and the wrist or ankle joint. The extent and severity of the inflammation relative to these zones was noted including: observation of each toe for swelling, torn nails or redness of toes; notation of any evidence of edema or redness in any of the paws; notation of any loss of fine anatomic demarcation of tendons or bones; evaluation of the wrist or ankle for any edema or redness; and notation if the inflammation extends proximally up the leg. A paw score of 1, 2, or 3 was based first on the overall impression of severity, and second on how many zones are involved. The scale used for clinical scoring is shown below:

Clinical Score
0=Normal
0.5=One or more toes involved, but only the toes are inflamed
1=mild inflammation involving the paw (1 zone), and may include a toe or toes
2=moderate inflammation in the paw and may include some of the toes and/or the wrist/ankle (2 zones)
3=severe inflammation in the paw, wrist/ankle, and some or all of the toes (3 zones)

C. Treatments

Established disease was defined as a qualitative score of paw inflammation ranking 1 or more. Once established disease was present, the date was recorded, designated as that animal's first day with "established disease," and treatment started. Mice were treated with PBS, or one of the following doses of human FcγRIA (hFcγRIA; diluted in PBS to desired concentration) subcutaneously every other day for a total of 6 doses: 2 mg; 0.667 mg; 0.22 mg, or one of the following doses of hFcγRIA (diluted in PBS to desired concentration) subcutaneously every 4th day for a total of 3 doses: 2 mg; 0.667 mg.

Blood was collected at the end of the experimental period to monitor serum levels of anti-collagen antibodies, as well as serum immunoglobulin and cytokine levels. Animals were euthanized 48 hours following their last treatment. Blood was collected for serum, and all paws and selected tissues were collected into 10% NBF for histology. Serum was collected and frozen at −800 C for immunoglobulin and cytokine assays.

Figure 10:
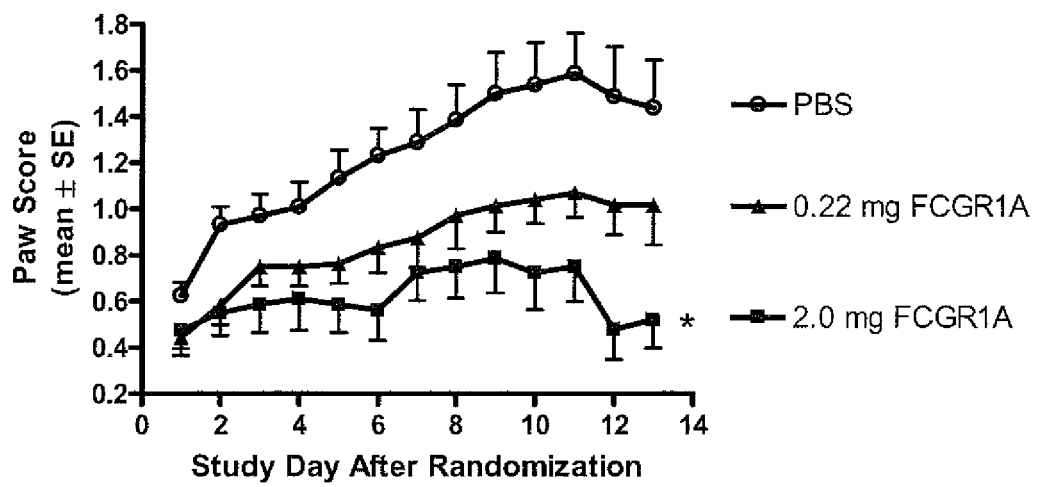
FIG. 10 depicts reduction in arthritis disease scores by treatment with FcγRIA. Collagen-induced arthritis (CIA) was established in mice as described in Example 13, infra. Once established disease was present, mice were treated with vehicle alone (PBS) (○), or vehicle containing 0.22 mg or 2.0 mg FcγRIA ("FCGR1A"). (See Example 13, infra.) Each point represents the mean±SE for 7-13 animals per group. Differences were significant, *p=0.001 by repeated measures ANOVA.
Figure 11:
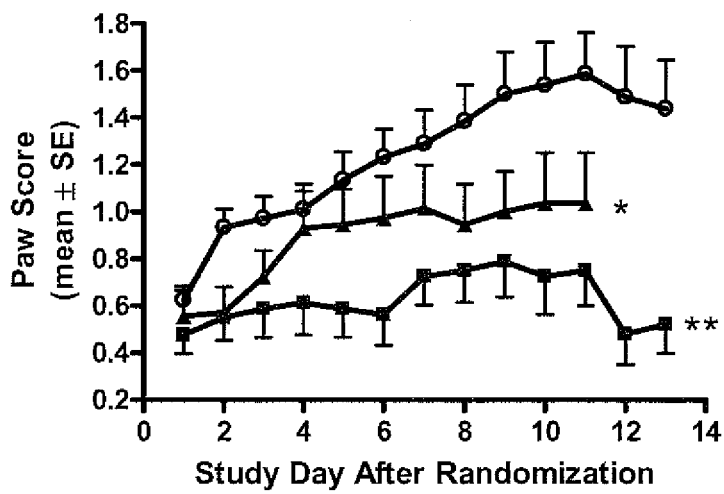
FIG. 11 depicts reduction in arthritis scores with an extended FcγRIA dose regimen. Collagen-induced arthritis (CIA) was established in mice as described in Example 13, infra. Mice were treated with vehicle alone (○) or vehicle containing 2.0 mg FcγRIA dosed either every other day (■) or every fourth day (▲). (See Example 13, infra.) Each point represents the mean±SE for 7-13 animals per group. Differences were significant, *p=0.0125, **p=0.001 by repeated measures ANOVA. Every fourth day dosing was for 11 days total.
Figure 12:
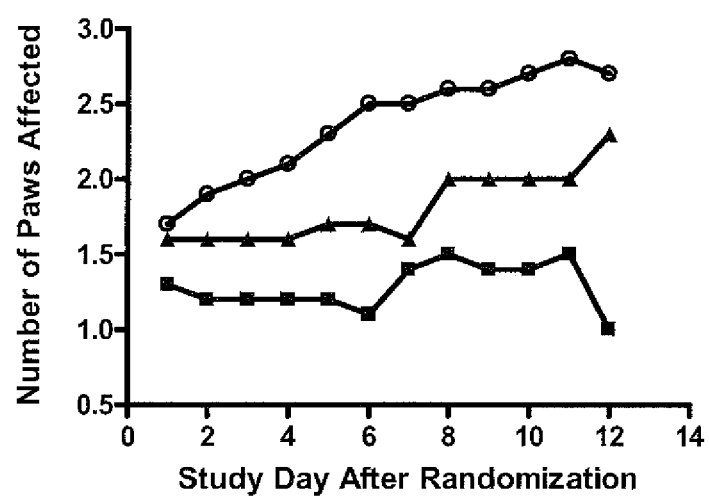
FIG. 12 depicts reduction in the number of arthritic paws with FcγRIA treatment. Collagen-induced arthritis (CIA) was established in mice as described in Example 13, infra. Mice were treated every other day with vehicle alone (○) or vehicle containing 0.22 mg FcγRIA (▼) or 2.0 mg (■) of FcγRIA dosed either every other day. (See Example 13, infra.) Each point represents the mean of 7-13 mice per group.
Figure 13A:
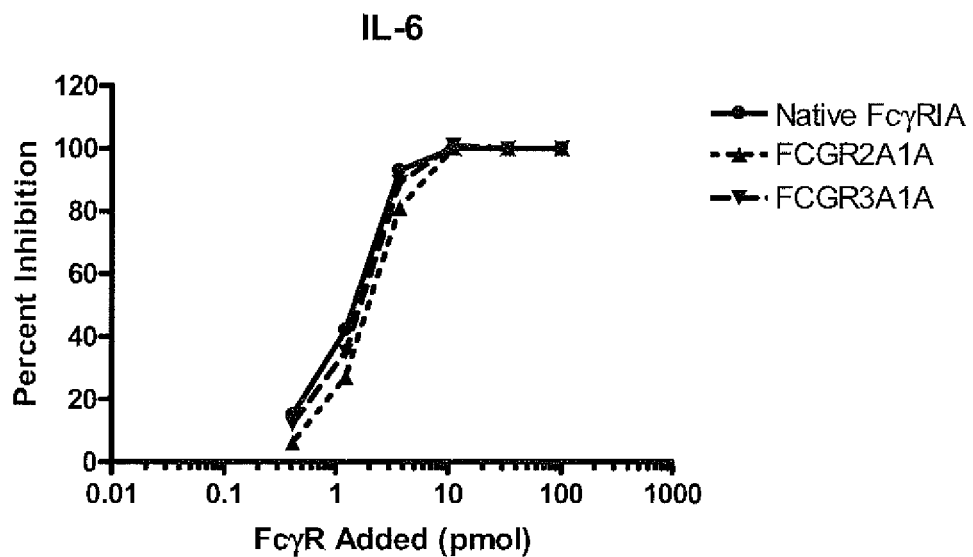
FIGS. 13A-13D depict inhibition of immune complex-mediated cytokine production in cultured mast cells by incubation with soluble native FcγRIA and soluble hybrid FcγRIIA/IA and FcγRIIIA/IA receptors. Murine MC/9 mast cells were incubated with anti-OVA/OVA immune complexes in the presence of increasing amounts of soluble native FcγRIA ("Native FCGR1A"), or one of two soluble hybrid receptors, FcγRIIA/IA-CH6 ("FCGR2A1A") or FcγRIIIA/IA-CH6 ("FCGR3A1A") and secretion of inflammatory cytokines, IL-6 (FIG. 13A), IL-13 (FIG. 13B), TNFα (FIG. 13C), and MCP-1 (FIG. 13D), were determined as described in Example 22, infra.
Figure 13B:
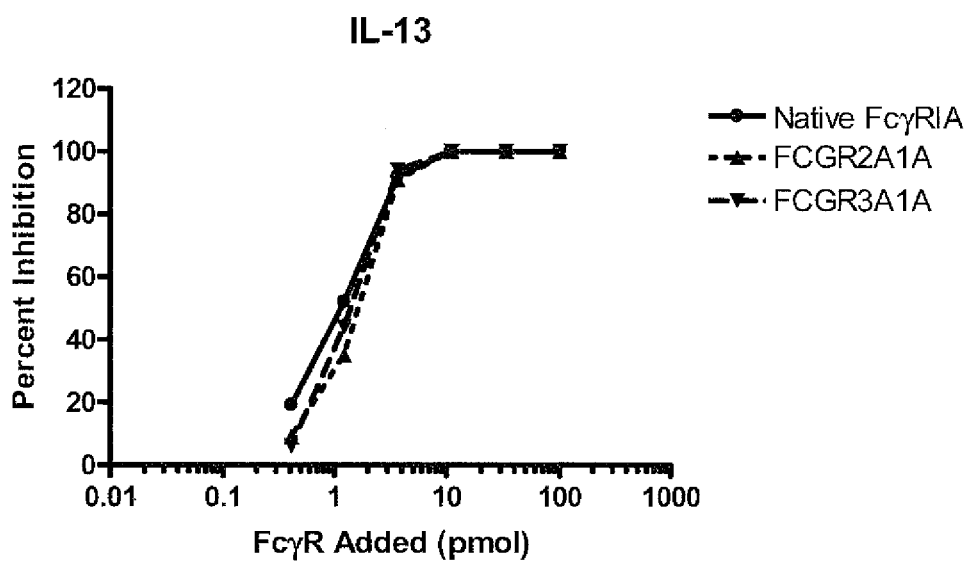
Figure 13C:
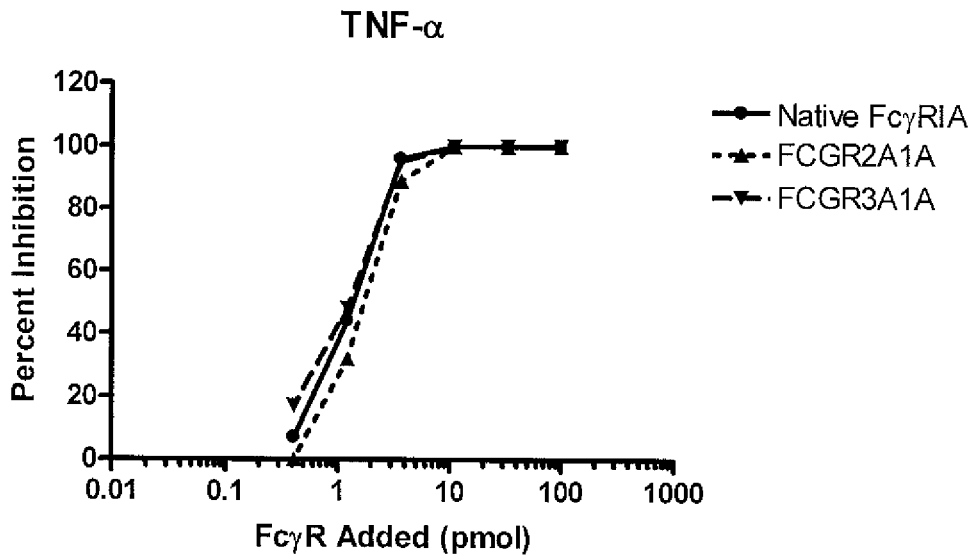
Figure 13D:
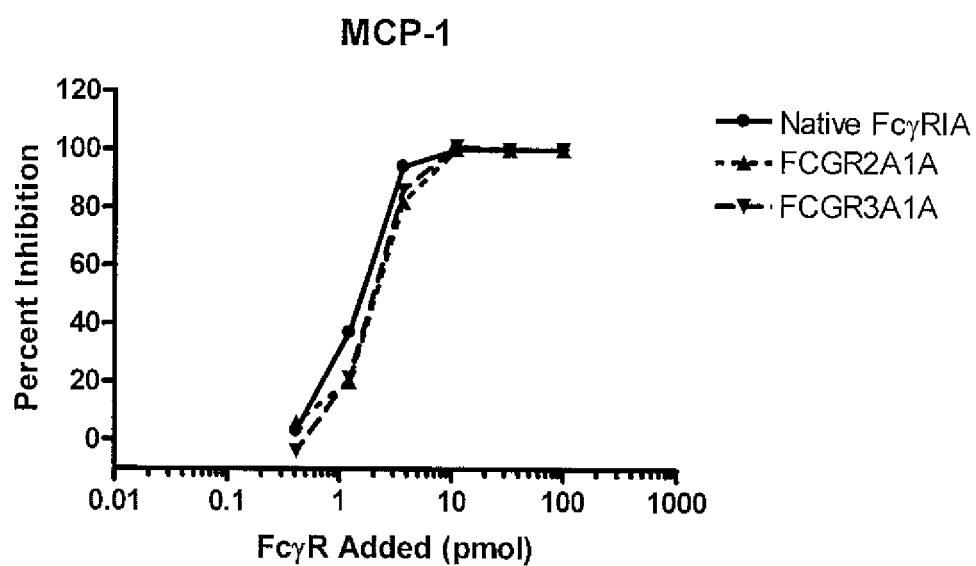

Mice injected with type II collagen and treated with vehicle developed paw swelling that was evident as higher disease scores (paw scores) with days after randomization (see FIG. 10, open circles). Treatment with FcγRIA every other day for 12 days produced a statistically significant, dose-dependent reduction in clinical scores (see FIG. 10, solid symbols). Treatment with the 0.22 mg dose produced a 50% reduction in disease progression, while the 2.0 mg dose reduced disease severity by 90%. Reduction in paw scores was also seen when FcγRIA was administered with an extended dose interval (see FIG. 11). Compared to treatment with vehicle alone (PBS), treatment with 2.0 mg of FcγRIA every fourth day for 9 days produced a 50% reduction in clinical scores, compared with the 90% reduction seen when FcγRIA was administered every other day (see FIG. 11). Mice treated with hFcγRIA also had a dose-dependent reduction in the number of affected paws (see FIG. 12).

In summary, these results indicate that in murine collagen-induced arthritis, administration of recombinant human FcγRIA can reduce disease incidence and progression. These data support the use of FcγRIA as a novel effective therapy for treatment of arthritis and other IgG- and immune complex-mediated diseases in humans.

Example 14

FcγRIA Decreases Levels of IL-6 and Anti-type II Collagen Antibodies in Mouse Collagen Induced Arthritis (CIA) Model In addition to monitoring disease development in the mouse CIA model by assessing the extent and severity of paw inflammation, mice used in the CIA study described above (see Example 13) were also assessed for levels of IL-6 and anti-type II collage antibodies, as summarized below.

A. Methods

Quantitation of Serum Cytokines by Luminex Assay

The level of cytokines in mouse sera were quantitated using a Luminex cytokine assay kit from Upstate Biotechnology. Each plate was blocked with 0.2 mL of Assay Buffer for 10 min, the buffer was removed and the plate blotted. A 0.025 mL of each standard, control, blank, and test sample was added to the appropriate wells followed by a 0.025 mL sample of Serum Matrix. A 0.025 mL volume of Assay Buffer was added to each sample well followed by 0.025 mL of capture beads that were suspended by sonication. Each plate was sealed, covered in foil, and incubated on a shaker at 4° C. After 18-24 h, the well contents were removed by aspiration and the plate was blotted. Each plate was then washed 2-3 times with 0.2 mL of wash buffer, 0.025 mL of Detection Antibody Cocktail was added to each well and the plate was sealed, covered in foil, and incubated on a shaker at room temperature for 60 min. A 0.025 mL sample of Streptavidin-Phycoerythrin was added to each well, each plate was sealed, covered in foil, and incubated on a shaker at room temperature for 30 min. The contents of each well were removed by aspiration, each plate was blotted, and washed 2-3 times with 0.2 ml/well of wash buffer. A 0.1 ml sample of Sheath Buffer was added to each well and the absorbance of each sample was read on a Luminex instrument.

Quantitation of Anti-Type II Collagen Antibodies

The level of anti-type II collagen antibodies in mouse sera were quantified using a Mouse IgG Anti-Type II Collagen Antibody Kit from Chondrex. Each plate was blocked with 0.1 mL of Blocking Buffer for 60 min at room temperature. The plates were washed three times with Wash Buffer and standards, samples, or blanks were added to the appropriate wells in a final volume of 0.1 mL. The plates were covered and incubated overnight at 4° C. The next day, each plate was washed six times with Wash Buffer and a 0.1 mL volume of secondary antibody was added to each well. The plates were then incubated at room temperature. After 2.0 h, each plate was washed and 0.1 mL of OPD solution was added to each well and incubated for 30 min at room temperature. The reactions were terminated by adding 0.05 mL of 2N sulfuric acid to each well and the absorbance of each well at 490 nm was determined.

B. Result

Compared to non-arthritic mice that did not receive injections of type-II collagen, mice injected with type-II collagen had elevated serum levels of IL-6 at the time of sacrifice on day 15. Levels of IL-6 were below the level of detection in normal mice and increased to 320 pg/mL in mice that developed collagen-induced arthritis and were treated with vehicle alone. Treatment with soluble human FcγRIA (2.0 mg given every other day for two weeks) reduced the serum levels of IL-6 by 70% to 95 pg/mL on day 15.

In addition to reducing the levels of IL-6, treatment with soluble human FcγRIA also reduced the levels of anti-type II collagen antibodies in the sera of arthritic mice. Administration of 2.0 mg of FcγRIA every other day produced a 40-50% reduction in the amount of anti-type II collagen antibodies, relative to the levels observed in arthritic mice treated with vehicle alone, on day 15 at the time of sacrifice.

Example 15

Construction of Hybrid Soluble C-term Six His FcγRIA Expression Plasmids to Express the First Ig Domain of FcγRIIA, FcγRIIB, FcγRIIIA, or FcγRIIIB Followed by the 2nd and 3rd Ig Domains of FcγR1A Expression constructs containing the first extracellular Ig domain of FcγRIIA, FcγRIIB, FcγRIIIA, or FcγRIIIB followed by the second and third extracellular Ig domains of human FcγRIA with a C-terminal tag, six His (c6×H) were generated. These hybrid FcγR constructs are also referred to as FcγRIIA/RIA-CH6, FcγRIIB/RIA-CH6, FcγRIIIA/RIA-CH6, and FcγRIIIB/RIA-CH6, respectively. These constructs were generated via PCR and homologous recombination using DNA fragments encoding the first Ig domain of FcγRIIA, FcγRIIB, FcγRIIIA, or FcγRIIIB, a DNA fragment encoding the second and third Ig domain of FcγRIA and the expression vector pZMP31.

Four PCR fragments were generated which encoded a 5' overlap with the pZMP31 vector sequence in the 5' non-translated region, the first Ig domain of FcγRIIA, FcγRIIB, FcγRIIIA, or FcγRIIIB and a 3' overlap with the second Ig domain of FcγRIA. The PCR amplification reactions used the 5' oligonucleotides: TCCACAGGTGTCCAGGGAAT-TCATATAGGCCGGCCATGGCTA TGGAGACCCAAAT-GTCT (SEQ ID NO:47; forward primer specific for FcγRIIA leader sequence), TCCACAGGTGTCCAGGGAAT-TCATATAGGCCGGCCATGGGAATCCTGTCATTCT-TACC (SEQ ID NO:48; forward primer specific for FcγRIIB leader sequence) or TCCACAGGTGTCCAGG GAAT-TCATATAGGCCGGCCATGTGGCAGCTGCTC-CCCCAACT (SEQ ID NO:49; forward primer specific for FcγRIIIA and FcγRIIIB leader sequence). The four PCR reactions were run with the 3' oligonucleotides CGT-GAAGACTCTGCTGGAGACCTGCAGTAGTAGCCAT-TCGGAAAG CACAGTCAGATGCAC (SEQ ID NO:50; reverse primer specific for domain 1 (first Ig domain) of FcγRIIA and FcγRIIB and which includes sequence overlap with domain 2 (second Ig domain) of FcγRIA), CGT-GAAGACTCTGCTGGAGACCTGCAGTAGTAGCCA-GCCGATATGGACTTCTAG CTGCAC (SEQ ID NO:51; reverse primer specific for domain 1 (first Ig domain) of FcγRIA and which includes sequence overlap with domain 2 (second Ig domain) of FcγRIA), or CGTGAAGACT CTGCTGGAGACCTGCAGTAGTAGCCAGCCGA-CATGGACTTCTAGCTGCAC (SEQ ID NO:52; reverse primer specific for domain 1 (first Ig domain) of FcγRIIIB and which includes sequence overlap with domain 2 (second Ig domain) of FcγRIA), utilizing previously generated DNA clones for soluble FcγRIIA (MPET construct #1202), FcγRIIB (MPET construct #1204), FcγRIIIA (MPET construct #1205), or FcγRIIIB (MPET construct #1207) as templates.

Three additional PCR fragments were generated that encode the second and third Ig domains of FcγRIA with a CH6 (C-terminal six-His) tag; these fragments contained (i) a 5' overlap with a PCR fragment encoding the first Ig domain of FcγRIIA, FcγRIIB, FcγRIIIA, or FcγRIIIB; (ii) an FcγRIA extracellular domain coding region (Ig domains 2 and 3); (iii) the-six His tag coding sequence; and (iv) a 3' overlap with the pZMP31 vector downstream of the MCS. The PCR amplification reactions used the following 5' oligonucleotides: CTCAGCGACCCTGTGCATCTGA CTGTGCrTTCCGAATGGCTACTACTGCAGGTCTC-CAGC (SEQ ID NO:53; forward primer specific for domain 2 (second Ig domain) of FcγRIA and which includes sequence overlap with the first Ig domain of FcγRIIA and FcγRIIB), CTCAGTGACCCGGTGCAGCTAGAAGTC-CATATCGG CTGGCTACTACTGCAGGTCTCCAGC (SEQ ID NO:54; forward primer specific for domain 2 (the second Ig domain) of FcγRIA and which includes sequence overlap with the first Ig domain of FcγRIIIA), or CTCA-GTGACCCGGTGCAGCTAGAAGTCCATGTCGGCTG-GCTACTACTGCAG GTCTCCAGC (SEQ ID NO:55; forward primer specific for domain 2 (second Ig domain) of FcγRIA and which includes sequence overlap with the first Ig domain of FcγRIIIB). Each of the three PCR reactions were run with the 3' oligonucleotide TACAACCCCA-GAGCTGTTTTAAGGCGCGCCTC TAGATTAGTGATG-GTGATGGTGATGTCC (SEQ ID NO:56; reverse primer specific for the C-terminus of the FcγRIA extracellular domain and which includes a six His tag and stop codon sequence) and a previously generated DNA clone of FcγRIA as the template (MPET construct #1198).

The PCR amplification reaction conditions were as follows: 1 cycle, 95° C., 5 minutes; 25 cycles, 95° C., 30 seconds, followed by 55° C., 30 seconds, followed by 68° C., 1 minute; 1 cycle, 72° C., 7 minutes. The PCR reaction mixtures were run on a 1% agarose gel and the DNA fragments corresponding to the expected size is were extracted from the gel using a QIAquick™ Gel Extraction Kit (Qiagen, Cat. No. 28704).

The plasmid pZMP31 is a mammalian expression vector containing an expression cassette having the chimeric CMV enhancer/MPSV promoter, FseI, NarI, and BglII sites for linearization prior to yeast recombination, an *E. coli* origin of replication; a mammalian selectable marker expression unit comprising an SV40 promoter, enhancer and origin of replication, a DHFR gene, and the SV40 terminator, and URA3 and CEN-ARS sequences required for selection and replication in *S. cerevisiae*.

The plasmid pZMP31 was digested with FseI, NarI, and BglII prior to recombination in yeast with the following corresponding combinations of gel extracted PCR fragments mentioned above: FcγRIIA and FcγRIA, FcγRIIB and FcγRIA, FcγRIIIA and FcγRIA, or FcγRIIIB and FcγRIA. 50 µl of competent yeast (*S. cerevisiae*) cells were combined with 3 µl of each PCR fragment insert DNA and 30 ng of FseI, NarI and BglII digested pZMP31 vector. The mix was transferred to a 0.2 cm electroporation cuvette. The yeast/DNA mixture was electropulsed using power supply (Bio-Rad Laboratories, Hercules, Calif.) settings of 0.75 kV (5 kV/cm), ∞ ohms, and 25 µF. Three hundred µl of 1.2 M sorbitol was added to the cuvette, and the yeast was plated in 75 µl and 200 id aliquots onto two URA-DS plates and incubated at 30° C. After about 72 hours, the Ura+ yeast transformants from a single plate were resuspended in 100 ul of yeast lysis buffer (0.1M NaCl, 0.0062M Tris HCl, 0.0038M Tris Base, 0.001M EDTA, 2% (v/v) polysorbate 20, 1% (w/v) SDS) and 100 µl of Qiagen MiniPrep kit buffer P1 containing 10 U Zymolyasel/100 ul. This mixture was then incubated at 37° C. for approximately 15 min. and the rest of the Qiagen miniprep kit protocol was followed according to manufacture's instructions.

Transformation of electrocompetent *E. coli* host cells (DH12S) was performed using 4 µl of the yeast DNA preparation and 50 µl of *E. coli* cells. The cells were electropulsed at 1.75 kV, 25 µF, and 400 ohms. Following electroporation, 0.5 ml LB was added and then the cells were plated in 10 µl and 30 µl aliquots on two LB AMP plates (LB broth (Lennox), 1.8% Bacto™ Agar (Difco), 100 mg/L Ampicillin).

The inserts of five DNA clones per construct were subjected to sequence analysis. One clone containing the correct sequence is selected. Large-scale plasmid DNA was isolated using a commercially available kit (QIAGEN Plasmid Mega Kit, Qiagen, Valencia, Calif.) according to manufacturer's instructions. The nucleotide sequences for the FcγRIIA/RIA-CH6, FcγRIIB/RIA-CH6, FcγRIIIA/RIA-CH6, and FcγRIIIB/RIA-CH6 hybrid constructs are shown, respectively, in SEQ ID NOs 39, 41, 43, and 45. The corresponding encoded amino acid sequences for FcγRIIA/RIA-CH6, FcγRIIB/RIA-CH6, FcγRIIIA/RIA-CH6, and FcγRIIIB/RIA-CH6 are shown, respectively, in SEQ ID NOs 40, 42, 44, and 46.

The same process was used to prepare native soluble sequence FcγRIA (which includes the native sequence Ig domains 1, 2 and 3) with a C-terminal his tag, composed of Gly Ser Gly Gly His His His His His His (FcγRIA-CHIS). To prepare this construct, a PCR fragment encoding native soluble sequence FcγRIA (which includes the native sequence Ig domains 1, 2 and 3) with a C-terminal his tag was generated using oligonucleotide primer TCCACAGGTGTCCAGGGA ATTCATATAGGCCGGCCATGTGGTTCTTGACAACTCTGCTC (SEQ ID NO:57; forward primer specific for FcγRIA leader sequence), oligonucleotide primer TACAACCCCAGAGCTGTTTTAAGGCGCGCCTCTAGATTAGTGATGGTGATGGTGATGTCC (SEQ ID NO:58; reverse primer specific for C-terminus of the FcγRIA extracellular domain and which includes a 6 His tag and stop codon sequence) and a previously generated DNA clone of FcγRIA as the template (MPET construct #1198).

The Mega Prep Plasmid DNA was utilized in transient transfections of 293F cells for downstream analysis of expression and aggregate levels. For each construct, 25 g of plasmid DNA was diluted into 300 μl of pre warmed 37° C. Optimem media (Invitrogen) and allowed to incubate at room temperature for 5 min. In a separate tube 32 ul of Lipofectamine 2000 (Invitrogen) was diluted into 300 μl pre warmed Optimem media and allowed to incubate at room temperature for 5 min. The contents of the two tubes were added together and mixed and allowed to incubate at room temperature for 30 min. with occasional, gentle mixing. After the DNA/lipofectamine complexes were formed, they were added to 25 ml of 293F cells at 1×10⁶ cells/ml cultured in Invitrogen Freestyle media. The culture was allowed to proceed for 96 hrs and the media was harvested by pelleting the cells via centrifugation for 5 min. at low speed. The media was saved and passed on for expression and aggregation level analysis (see Example 16, infra).

Example 16

Analysis of Soluble Hybrid FcγR Constructs from Transient 293F Conditioned Media Soluble FcγRIA protein has a tendency to form self-associated complexes and aggregates under normal cell culture temperatures. Soluble forms of other Fcγ receptor family members (FcγRIIA, FcγRIIB, FcγRIIA, FcγRIIIB) do not appear to show the level of self-association that FcγRIA does.

Soluble hybrid FcγR constructs were generated where the first Ig domain of FcγRIA was replaced with the first Ig domain of one of the other family members (FcγRIIA, FcγRIIB, FcγRIIIA, FcγRIIIB), as described above (see Example 15). These hybrid constructs (FcγRIIA/RIA-CH6, FcγRIIB/RIA-CH6, FcγRIIIA/RIA-CH6, and FcγRIIIB/RIA-CH6) were transiently transfected into 293F cell lines, and the conditioned media from those cells were assessed for expression and capture on Ig-Sepharose Resin (GE Healthcare, Uppsala, Sweden). Soluble, native versions of other family members were also expressed and analyzed in similar fashion.

IgG Sepharose has been shown experimentally to only bind monomeric, non-aggregated FcγRIA. Accordingly, the ability of various FcγR constructs to bind IgG Sepharose was used as a measure of each construct's tendency to self-aggregate (where increased binding to IgG Sepharose indicates decreased tendency to self-aggregate).

Conditioned media expressing the native and hybrid constructs was subjected to binding to IgG Sepharose in batch mode. 300 uL of packed resin was pre-eluted using 19.9 mM Citric Acid (EMD, Darnstadt, Germany), 5.1 mM Dibasic NaPO₄, 150 mM NaCl, 0.05% Tween 20 (EM Science, Darnstadt, Germany) pH 3.0, and then equilibrated in 1.61 mM Citric Acid, 23.4 mM Dibasic NaPO₄, 150 mM NaCl pH 7.0.

The equilibrated resin was combined with 10-25 mL of conditioned media and incubated for 1 hour at 4° C. while slowly turning. After 1 hour, the mixture was transferred to a BioRAD Econo-column (Hercules, Calif.) and the flow-through collected in a separate vessel via gravity flow. The resin was then washed with 80 column volumes using equilibration buffer. Bound protein was eluted using 4 mL of elution buffer, incubating the resin for roughly 5 minutes before collecting the elution fraction. The resin was chased with another 1 mL of elution buffer, and that chase volume was collected in the same vessel as the elution fraction. The elution fraction was neutralized using 0.5 mL 2M Tris pH 8.0.

Load, flow-through, and elution fractions were further analyzed via western blot under non-reducing conditions, where the prepped samples were also not heated in any way. Samples were loaded onto 4-12% Bis-Tris gel using MES running buffer (Invitrogen, Carlsbad, Calif.), normalizing all for volume, and the gel was run at constant 150V. SDS-PAGE gel was then transferred to 0.2 μm nitrocellulose using the I-Blot system (Invitrogen). Non-specific sites on the blot were then blocked using 2.5% non-fat dry milk (NFDM) in Western A buffer (0.097% (w/w) TRIS base, 0.661% (w/w) Tris HCl, 0.18612% (w/w) EDTA, 0.05% (v/w) Igepal, 0.877% (w/w) NaCl, 0.25% Gelatin). The blot was probed with anti-Fcγ R1/CD64 monoclonal antibody (R&D, Minneapolis, Minn.) diluted 1:1000 in 2.5% NFDM in Western A buffer and then anti-Murine JgG-HRP (Santa Cruz Biotech, Santa Cruz, Calif.), incubating each for 1 hour at room temperature with washes of Western A buffer between incubations. As prepped, the samples were analyzed for percent of target in the flow through (aggregate amount) and percent in the elution pool (monomer amount) as compared to the total expressed in the load (aggregate and monomer). This analysis was performed on the ImageQuant RT ECL imager running the ImageQuant TL v2005 software (GE Healthcare, Uppsala, Sweden).

Two FcγR hybrid constructs showed improvement in the amount of aggregate and monomer expressed (i.e., decreased amount of aggregate and increased amount of monomer) when compared to native soluble FcγRIA. Native, soluble FcγRIA showed an average aggregate amount of 66% of the total expressed, with 21% of the total expressed being recovered from the IgG resin (13% of the total expressed was not accounted for). The FcγRIIA/RIA hybrid showed an average aggregate amount of 14.2% and an IgG recovered amount of 40% (48% was unaccounted for). The FcγRIIIA/RIA hybrid showed an average aggregate amount of 36% with 82% being recovered from the IgG resin. These results are represent an n=2.

Example 17

Expression of Soluble Hybrid FcγR Constructs in CHO Cells

For the hybrid constructs with sequence for soluble C-terminal six-his FcγRIA to express the first Ig domain of FcRIIA or FcγRIIA, followed by the second and third Ig domains of FcγRIA (see Example 15), 600 g of each of the expression constructs (mega prep plasmid) were digested with 720 units of BstB1 restriction enzyme at 37° C. for 2.5 hours, washed with phenol/chloroform/isoamyl alcohol, followed by a wash with chloroform/isoamyl, then precipitated overnight with ethanol, and centrifuged in a 1.5 mL microfuge tube. The supernatants were decanted and the pellets were washed with 1 mL of 70% ethanol and allowed to incubate for 5 minutes at room temperature. The tubes were spun in a microfuge for 10 minutes at 14,000 RPM and the supernatants were decanted off the pellets. In the sterile environment on the tissue culture hood, the pellets were allowed to dry in the open air for apx. 5 min, then resuspended in 1.2 mls of 37° C., pre-warmed CHO cell tissue culture medium and allowed to incubate at 37° C. for 10 minutes. While the DNA pellets were being solubized, approximately $5.6 \times 10^7$ CHO cells were pelleted and resuspended in 2.4 mls of CHO cell tissue culture medium. Each solublized plasmid preparation was divided into three 400 µl volumes and then 400 µl of the CHO cell suspension was added for a final volume of 800l. The DNA/cell mixtures were placed in a 0.4 cm gap cuvette and electroporated using the following parameters; 950 µF, high capacitance, at 300 V. For each plasmid electroporation set, the contents of the cuvettes were then removed, pooled, and diluted to 25 mLs with CHO cell tissue culture medium and placed in a 125 mL shake flask. The flask was placed in an incubator on a shaker at 37° C., 5% $CO_2$ with shaking at 120 RPM.

The CHO cells were subjected to nutrient selection and amplification to 500 nM Methotrexate (MTX). The selected CHO lines were designated MECL 1308 (FcγRIIA/IA hybrid) and 1309 (FcγRIA/IA hybrid).

To test for expression, cultures were set up using passage 7 post-electroporation pools. Cells were centrifuged and resuspended in fresh media in a 50 ml volume at $0.6 \times 10^6$ cells/ml and allowed to proceed as previously described for 96 hrs. Tagged protein expression was confirmed by Western blot.

Example 18

Expression of FcγRIIA/IA-CH6 Protein in CHO DXB11 Cells in a Wave Reactor

FcγRIIA/IA-CH6 protein was expressed in a 10 L Wavebag Reactor (Wave Biotech) in CHO DXB11 cells transfected with the ZG construct 1892. The cells were scaled up in shake flasks using ZM2 medium (SAFC Biosciences Ex-CELL catalog #68041) with the addition of 5 mM L-glutamine (from 200 mM L-glutamine, Gibco catalog #25030-081), 1 mM sodium pyruvate (from 100 mM Sodium Pyruvate, Gibco catalog #11360-070) and 500 nM methotrexate. The reactor run was initiated by seeding 500 mL of shake flask culture in log phase into 4.5 L ZM2 medium containing L-glutamine and sodium pyruvate but no methotrexate. This resulted in a 5 L final working volume with a density of $3.5 \times 10^5$ cells/mL.

The $CO_2$ level was maintained at 3%-6% and was pumped continually into the headspace of the reactor at 0.2 LPM. Dissolved oxygen requirements of the cells were met by rocking the culture on a platform at a rate of 25 rocks per minute at an angle setting of 9.5. pH was not controlled but stayed between 6.6 and 7.0. Temperature was maintained at 37° C. until density reached $2.0 \times 10^6$ cells/mL, then temperature was dropped to 34° C. for the remainder of the run. Glucose levels were maintained above 2 g/L and L-glutamine above 2 mM.

The culture was harvested 11 days after seeding with a density of $7.5 \times 10^6$ cells/mL and 96% viability. The supernatant was centrifuged at 3500×g for 15 minutes and the clarified conditioned medium was passed through a 0.22 µm filter (Millipore Opticap catalog #KWSSL4HB3) and submitted for protein purification.

Example 19

Expression of FcγRIIIA/IA-CH6 Protein in CHO DXB11 Cells in a Wave Reactor

FcγRIIIA/IA-CH6 protein was expressed in a 10 L Wavebag Reactor (Wave Biotech) in CHO DXB11 cells transfected with the ZG construct 1894. The cells were scaled up in shake flasks using ZM2 medium (SAFC Biosciences Ex-CELL catalog #68041) with the addition of 5 mM L-glutamine (from 200 mM L-glutamine, Gibco catalog #25030-081), 1 mM sodium pyruvate (from 100 mM Sodium Pyruvate, Gibco catalog #11360-070) and 500 nM methotrexate. The reactor run was initiated by seeding 500 mL of shake flask culture in log phase into 4.5 L ZM2 medium containing L-glutamine and sodium pyruvate but no methotrexate. This resulted in a 5 L final working volume with a density of $3.1 \times 10^5$ cells/mL.

The $CO_2$ level was maintained at 3%-6% and was pumped continually into the headspace of the reactor at 0.2 LPM. Dissolved oxygen requirements of the cells were met by rocking the culture on a platform at a rate of 25 rocks per minute at an angle setting of 9.5. pH was not controlled but stayed between 6.6 and 7.0. Temperature was maintained at 37° C. until density reached $1.4 \times 10^6$ cells/mL, then temperature was dropped to 34° C. for the remainder of the run. Glucose levels were maintained above 2 g/L and L-glutamine above 2 mM.

The culture was harvested 11 days after seeding with a density of $6.3 \times 10^6$ cells/mL and 97% viability. The supernatant was centrifuged at 3500×g for 15 minutes and the clarified conditioned medium was passed through a 0.22 µm filter (Millipore Opticap catalog #KWSSL4HB3) and submitted for protein purification.

Example 20

Purification of Soluble FcγRIA and FcγRIIIA/IA-CH6

Large scale production of rh-FcγRIA and FcγRIIIA/IA-CH6 was performed in 10 L Wavebag Reactor (Wave Biotech). Cells were scaled up in shake flasks using ZM2 medium (SAFC Biosciences Ex-CELL) with the addition of 5 mM L-glutamine, 1 mM sodium pyruvate, and 500 nM methotrexate. The reactor run was initiated by seeding 500 mL of shake flask culture in log phase into 4.5 L ZM2 medium containing L-glutamine and sodium pyruvate but no methotrexate. This resulted in a 5 L final working volume with a density of 3.1×10³ cells/mL. The $CO_2$ level was maintained at 3%-6% and was pumped continually into the headspace of the reactor at 0.2 LPM. Dissolved oxygen requirements of the cells were met by rocking the culture on a platform at a rate of 25 rocks per minute at an angle setting of 9.5. pH was not controlled but stayed between 6.6 and 7.0. Temperature was maintained at 37° C. until density reached 1.4×10⁶ cells/mL, then temperature was dropped to 34° C. for the remainder of the run. Glucose levels were maintained above 2 g/L and L-glutamine above 2 mM. The culture was harvested 11 days after seeding with a density of 6.3×10⁶ cells/mL and 97% viability. The supernatant was centrifuged at 3500×g for 15 minutes and the clarified conditioned medium was passed through a 0.22 μm filter (Millipore Opticap) prior to protein purification.

Untagged rh-FcγRIA was purified by sequential chromatography on IgG-Sepharose, Poros HS-50, and Superdex 75 as described in Example 8, supra.

His-tagged FcγRIIIA/IA was purified by sequential chromatography on Ni-NTA Superflow resin, Q-Sepharose, and Superdex 200. Briefly, CHO-conditioned media were sterile filtered, concentrated, and buffer exchanged into 50 mM $NaPO_4$, 500 mM NaCl, 25 mM imidazole, pH 7.5 (Buffer A). His-tagged FcγRIIIA/IA protein was captured using Ni-NTA His Bind Superflow resin (Novagen, Madison, Wis.) equilibrated in Buffer A. Elution of bound protein was accomplished using a gradient of imidazole (0-500 mM) in 50 mM $NaPO_4$, 500 mM NaCl, pH 7.5. Fractions were analyzed for FcγRIIIA/IA by SDS-PAGE and Western blotting (anti-6× Histidine HRP mouse IgG1, R & D Systems, Minneapolis, Minn.).

The Ni-NTA fractions containing FcγRIIIA/IA-CH6 were buffer-exchanged into 50 mM $NaPO_4$, 150 mM NaCl, pH 7.5 (Buffer B) and incubated with Q Sepharose 4FF resin (GE Healthcare, Uppsala, Sweden) that was pre-equilibrated in Buffer B overnight at 4° C. The slurry was transferred to a gravity flow column, the flow-through and wash fractions were combined and assessed for the presence of rh-FcgR as described above. The combined fractions were concentrated and injected onto a Superdex 200 Hiload (GE Healthcare, Uppsala, Sweden) column equilibrated in 50 mM $NaPO_4$, 109 mM NaCl, pH 7.3 (Buffer C). The column was eluted in Buffer C and fractions containing FcγRIIIA/IA-CH6 were combined, concentrated, sterile-filtered, and stored at −80° C. FcγRIIIA/IA-CH6 was analyzed by SDS-PAGE, Western blotting, N-terminal sequencing, and size exclusion multi-angle light scattering.

Example 21

Aggregation Studies

Aggregation of Soluble Native FcγRIA

Large scale production of soluble recombinant human FcγRIA (CD64A) from mammalian cells has historically been problematic. (See Berntzen et al., *J. Immunol. Methods* 298:93-104, 2005; Sondermann and Oosthuizen, *Biochem. Soc. Trans.* 30:481-486, 2002; Paetz et al., *Biochem. Biophys. Res. Commun.* 338:1811-1817, 2005; Bruhns et al., *Blood* DOI 10.1182, 2008/blood-2008-09-179754]. The present inventors have discovered that low yields of soluble recombinant human FcγRIA from either 293f or CHO DXB-11 cells are largely due to temperature-dependent, non-covalent self-association of the protein resulting in large soluble aggregates. Formation of the FcγRIA aggregates, moreover, limits the recovery of protein from cell culture conditioned medium. To study the aggregation process in greater detail, FcγRIA was purified from the conditioned medium of CHO DXB-11 cells as described above. The highly-purified FcγRIA protein was incubated for various times at 4° C., 25° C. and 37° C. and the formation of aggregates was monitored by size exclusion chromatography on a Superdex 75 column.

The elution profile of FcγRIA, following incubation for up to 48 h at either 4° C. or 25° C., was identical to that of a freshly-thawed sample of FcγRIA, i.e., the protein eluted from the column as a single homogenous peak with an elution time of 10.3 minutes. Incubation of FcγRIA for 0, 2, 5, 20, or 48 h at 37° C., in contrast, resulted in a time-dependent reduction in the amount of material eluting as monomeric FcγRIA with a quantitative increase in material eluting at 7.8 min, an elution profile consistent with the formation of large FcγRIA aggregates. For samples incubated for 0, 2, 5, 20, or 48 h at 37° C., the amount of material recovered as aggregate was 0%, 17%, 43%, 83% and 93% of the total FcγRIA applied to the column, respectively.

To assess whether aggregated FcγRIA was biologically active, material incubated at 37° C. for 20 h (83% aggregated) was tested for inhibition of immune complex precipitation as described previously. (See Ellsworth et al., *J. Immunol.* 180, 580-589, 2008.) Incubation of a mixture of ovalbumin and anti-ovalbumin with increasing amounts of non-incubated (monomeric) FcγRIA produced a dose-dependent inhibition of immune complex precipitation with maximal inhibition observed with 5.0 μM FcγRIA. In contrast, little or no inhibition was observed with identical concentrations of aggregated FcγRIA. Similar results were obtained in an IgG-Sepharose elution assay where cell conditioned media or purified FcγRIA protein was applied to a small column of IgG-Sepharose. In this assay, the FcγRIA sample was applied to the column, the column was washed with PBS and the bound FcγRIA was eluted with low pH buffer. The wash fractions and the low pH buffer elution were collected and the amount of FcγRIA in the load, wash, and elution fractions was assessed by Western blotting with anti-FcγRIA specific antibodies. For FcγRIA incubated at 37° C. for 48 h, 96% of the total FcγRIA was found in the unbound wash fraction and 4% was in the bound fraction. In contrast, for FcγRIA incubated at 4° C., the entire sample was found in the bound fraction. These data demonstrate that aggregated FcγRIA does not bind to IgG-Sepharose. Taken together, these data demonstrate that aggregated FcγRIA is biologically inactive.

The temperature-dependent aggregation of FcγRIA appears to be irreversible as the Superdex 75 elution profile of previously aggregated material was not altered by an additional incubation at 4° C. or 25° C. or by the addition of an excess amount of human IgG1.

Further evidence for a temperature-induced unfolding of FcγRIA came from measurements of the circular dichroism (CD) spectra of FcγRIA following incubation of FcγRIA at 37° C. in phosphate buffer for 0, 5, 10, 15, or 20 h. For non-incubated FcγRIA (0 h), two peaks of CD signal were observed at approximately 270 nm and 290 nm separated by a trough at about 285 nm. With FcγRIA incubated for various times at 37° C., a time-dependent decrease in CD signal intensity was observed across these wavelengths indicating a time- and temperature-dependent loss of structure for FcγRIA.

These data were further substantiated by assessing the stability of FcγRIA in solution by dynamic light scattering (DLS). In DLS experiments, time-dependent fluctuations in light scattering intensity resulting from molecules diffusing in solution was measured. Changes in light scattering are related to molecular size and conformation. Diffusion coefficients were measured which were then used to calculate the hydrodynamic radius (Rh) of FcγRIA. FcγRIA was incubated in phosphate buffer pH 7.3 at 25° C. and 37° C. for various times and the Rh was assessed. For non-incubated FcγRIA (0 h) the Rh was ~3.4 nm. No change in the Rh was noted for FcγRIA incubated at 25° C. for various periods of time (Rh~3.2 nm for all incubation times). In contrast, the Rh of FcγRIA increased with time of incubation at 37° C. to 4.1 nm, 5.2 nm, 6.4 nm, and 12.8 nm for samples incubated for 1.0 h, 2.0 h, 3.0 h, and 48 h, respectively. These data indicate that FcγRIA was either multimerizing or unfolding over time at 37° C. in this formulation.

The data described above demonstrated that highly purified FcγRIA was unstable and formed inactive, self-associated aggregates when incubated at 37° C. in phosphate buffer at neutral pH. To evaluate whether aggregation also occurred in the conditioned media of CHO cells expressing FcγRIA, undiluted conditioned media from cells maintained at 37° C. was evaluated using the IgG-Sepharose binding assay described above. For FcγRIA-expressing CHO cells cultured at 37° C., one-day conditioned media were collected and applied to the IgG-Sepharose column. Eighty percent of the recovered FcγRIA was found in the unbound fraction (aggregated protein) with the remainder (20%) eluting from the column as monomeric FcγRIA. These data indicate that FcγRIA aggregates within the conditioned media of CHO cells and likely explains the poor production/recovery of recombinant soluble FcγRIA recorded by others. (See Berntzen et al., supra; Sondermann and Oosthuizen, supra; Paetz et al., supra; Bruhns et al., supra.)

Stability Studies of the Hybrid Receptor FcγRIIIA/IA

To circumvent the temperature-induced aggregation of native recombinant soluble FcγRIA, a hybrid FcγR molecule was generated using a domain-swapping protocol where the membrane distal Ig domain of native FcγRIIIA (CD16A) was substituted for the membrane distal Ig domain of native FcγRIA using the protocol described above. As noted above, the in vitro and in vivo biological activities of the hybrid receptor, FcγRIIIA/IA, was identical to that of native FcγRIA. To assess whether the hybrid receptor, FcγRIIIA/IA, was as sensitive to temperature-induced aggregation, native FcγRIA and the hybrid receptor, FcγRIIIA/IA, were each incubated at 37° C. in phosphate buffer, pH 7.3 for various lengths of time. Aggregation of each FcγR was monitored by size exclusion chromatography as described above and the percent of the total FcγR present as aggregate was calculated. The percent aggregation of native FcγRIA incubated for 0 h, 2 h, 4 h, 20 h, 24 h, or 48 h at 37° C. was 0, 14%, 40%, 81%, 84%, and 95%, respectively. In contrast, the percent aggregation for FcγRIIIA/IA incubated under identical conditions was 0, 2%, 6%, 30%, 34%, and 51%. The difference in aggregation between native FcγRIA and FcγRIIIA/IA was even more pronounced in 0.1M succinate buffer, pH 6.0: the percent aggregation of native FcγRIA incubated for 0 h, 2 h, 4 h, 20 h, 24 h, or 48 h was 0, 5%, 13%, 52%, 55%, and 77%, respectively. The percent aggregation of FcγRIIA/IA under these conditions was 0, 0, 0%, 0%, 5%, 8%, and 16%, respectively. These data indicate that the hybrid receptor, FcγRIIIA/IA, in much less susceptible to temperature-induced aggregation than native FcγRIA.

Similar data were obtained by dynamic light scattering (DLS) analysis of FcγRIIA/IA under conditions identical to those described above for native FcγRIA. In contrast to the increase in Rh of native FcγRIA following incubation of the protein at 37° C., no change in hydrodynamic radius (Rh) was observed for FcγRIIIA/IA after incubation at 37° C. for up to 3.0 h (Rh=3.6-3.8 over these times). A small increase in Rh, to 5.1 nm, was seen for FcγRIIIA/IA incubated at 37° C. for 48 h. As described above, this increase in Rh was much less than that observed for native FcγRIA incubated under identical conditions were the Rh increased to 12.8 nm. Again, these data demonstrate that the hybrid receptor FcγRIIIA/IA is less susceptible to temperature-induced aggregation compared with native FcγRIA.

To assess whether recovery of monomeric FcγRIIIA/IA in CHO conditioned media was increased relative to that of native FcγRIA, the amount of monomeric and aggregated FCGR in 24 h cultures of CHO cells expressing each of these receptors was compared. Aggregation was monitored using the IgG-Sepharose binding assay with detection by Western blotting as described above. As a percent of the total FcγR applied to the column, 53% of FcγRIIIA was monomeric in that it bound to IgG-Sepharose and was eluted in the low pH wash step, while 47% of the protein eluted in the wash as aggregated material. In contrast, for native FcγRIA, only 14% of the protein bound to IgG-Sepharose with 86% of the protein eluted in the wash as aggregated material. As with the pure protein, these data indicate that FcγRIIA/IA is less susceptible to temperature-induced aggregation in CHO-conditioned media and can be recovered in increased amounts relative to native FcγRIA.

Example 22

Comparison of Anti-Inflammatory Activities of Soluble FcγRIA, FcγRIIA/RIA, and FcγRIIIA/IA Methods
1. Immune Complex Precipitation Chicken egg ovalbumin (OVA) was dissolved to a final concentration of 15.0 μg/mL in phosphate buffered saline (PBS) and combined with 300 μg rabbit polyclonal anti-OVA antibodies/mL in a final volume of 200 μL in the presence and absence of the indicated concentration of native FcγRIA soluble receptor or one of the hybrid soluble receptors, FcγRIIA/IA-CH6 or FcγRIIIA/IA-CH6 (also referred to in this Example as "FcγRIIA/IA" (or "FCGR2A1A") and "FcγRIIIA/IA" (or "FCGR3A1A"), respectively). Immediately thereafter, turbidity of the reaction mixture was monitored at 350 mm every 30 seconds for 5-10 min at 37° C. with the aid of a spectrophotometer. Linear regression was used to calculate the slope of the linear portion of the turbidity curves and the FcγR-mediated inhibition of immune complex precipitation was expressed relative to incubations containing anti-OVA and OVA alone.
2. Cytokine Secretion from Mast Cells Immune complexes were prepared by mixing 300 μL of rabbit polyclonal anti-OVA with 75.0 μL of 1 mg OVA/mL in PBS in a final volume of 5.0 mL of PBS. After incubation at 37° C. for 30-60 min, the mixture was placed at 4° C. for 18-20 h. The immune complexes were collected by centrifugation at 12,000 rpm for 5.0 min, the supernatant fraction was removed and discarded, and the immune complex precipitate was resuspended 1.0 mL of ice cold PBS. After another wash, the immune complexes were resuspended in a final volume of 1.0 mL ice cold PBS. Protein concentration was determined using the BCA assay.

MC/9 cells were sub-cultured in Medium A (DMEM containing 10% fetal bovine serum, 50.0 μM B-mercaptoethanol, 0.1 mM non-essential amino acids, 1.0 mM sodium pyruvate, 36.0 μg/mL L-asparagine, 1.0 ng/mL rmIL-3, 5.0 ng/mL rmIL-4, 25.0 ng/mL rmSCF) to a density of 0.5-3×10⁶ cells/mL. Cells were collected by centrifugation at 1500 rpm for 5.0 min and the cell pellet was washed in Medium A (without cytokines) and resuspended in Medium A at 2.0×10⁶ cells/mL. Aliquots of cells (2.0×10⁵ cells) were incubated with 10.0 μg/well of OVA/anti-OVA immune complexes (IC's) in a final volume of 200 μL of Buffer A in a 96-well microtiter plate in the presence and absence of the indicated concentration of native FcγRIA soluble receptor or one of the hybrid soluble receptors, FcgRIIA/IA-CH6 or FcgRIIA/IA-CH6. After 4.0 h at 37° C., the media was removed and centrifuged at 1500 rpm for 5.0 min. The cell-free supernatant fractions were collected and aliquots were analyzed for the presence of IL-6, IL-13, TNFα, and MCP-1 cytokine release using a Luminex cytokine assay kit.

3. Measurement of FcγR Affinity for Human IgG1

The IgG1 antibody was immobilized to a single flow cell, utilizing a second non-derivatized cell as the blank reference. Immobilization of the IgG1 antibody was performed using an amine coupling kit (Biacore) and the standard Wizard Template for Surface Preparation, operated by the Biacore Control Software. Based on Wizard results for a pH scouting study, the IgG1 antibody solution was diluted to 11 μg/mL in sodium acetate, pH 5.0. The Wizard Template for amine coupling was used to immobilize the antibody to a single flow cell. The carboxyl groups on the sensor surfaces were then activated with an injection of a solution containing 0.2 M N-ethyl-N'-(3-diethylamino-propyl) carbodiimide (EDC) and 0.05 M N-hydroxysuccinimide (NHS). The antibody solution was then injected over the activated surface targeting a level of 150-200 RU. The immobilization procedure was completed by blocking remaining ester sites on the carboxymethyl dextran surface with 1 M ethanolamine hydrochloride.

The method for injection of the analyte solutions (soluble native FcγRIA or the soluble hybrid receptors, FcγRIIA/IA and FcγRIIIA/IA) was written using the Biacore Wizard Template for kinetic analysis. The method was run at 25° C. and the samples stored in the autosampler at ambient temperature. It is noted that in using the Wizard Template, certain parameters optimal for kinetics, such as injection modes, are pre-defined by the Wizard program.

The method for analysis of soluble FcγRIA was optimized for determination of kinetic rate constants, $k_a$ and $k_d$. The receptor was injected over both flow cells (i.e., 1 and 2, blank and antibody-derivatized, respectively) in series to allow for comparative analysis of binding of the FcγR to the human IgG1 antibody vs. binding of the FcγR to the non-modified control surface (binding to rabbit anti-OVA IgG not tested). The analyte was injected at a flow rate of 40 L/min for 3 minutes (association time). The dissociation time for each analyte injection was 3 minutes. The analyte dose response curve range was 0.16-10.3 nM. For each dose response curve point, N=2 replicate injections were run. The sequence included injections of buffer for subtraction of instrument noise and drift. Dose response curve samples were injected in random mode. For kinetic analysis of FcγR, each dose response curve cycle was followed by a single 30 second injection of glycine, pH 1.75 at 50 μL/minute to regenerate the IgG antibody surface.

Data analysis was performed using Biacore Control, Evaluation and Simulation software. Baseline stability was first assessed to ensure that the regeneration step provided a consistent binding surface throughout the sequence of injections. The level of non-specific binding of the FcγR analyte to the control surface was checked and confirmed to be minimal. Binding curves were processed by subtraction of the control surface curve (i.e., flow cell 1) from the specific binding surface curve (i.e., flow cell 2), as well as subtraction of instrument noise and drift using a buffer injection curve. The data was checked for reproducibility of analyte injections and the resulting corrected binding curves were then globally fitted to binding models and the resulting fit and equilibrium constants evaluated.

4. Cutaneous Reverse Passive Arthus Reaction in Mice

Ten-week old female C57BL/6 mice (n=8 mice per group) were anesthetized with isoflurane, their dorsal skin was shaved, and the back of each mouse was wiped with 70% alcohol. Each mouse received two intradermal injections of 0.02 mL each, at distinct sites in the dorsal skin. The injection solutions contained phosphate buffered saline (PBS) and either 40.0 μg of rabbit anti-ovalbumin (anti-OVA, heat-inactivated by incubation at 56° C. for 30-40 min) alone or 40.0 μg of anti-OVA and the indicated amount of soluble native FcγRIA or one of the soluble hybrid receptors, FcγRIIA/IA or FcγRIIIA/IA. Mice in the control groups received two intradermal injections of 40.0 μg non-immune rabbit IgG (heat-inactivated as described above). Antibody preparations were centrifuged at 14,000 rpm for 10 min to remove particulates prior to injection. Immediately following the intradermal injections, each mouse was injected in the tail vein with 100.0 μL of a solution containing 10.0 mg OVA/mL and 10.0 mg Evan's Blue/mL. In some instances, the tail vein injection solution also contained dexamethazone at a dose of 1.0 mg/kg. Four hours after the injections, the mice were euthanized by $CO_2$ gas. Cutaneous edema was evaluated by measuring the area of vascular leak of Evan's Blue dye ($mm^2$) and by measuring tissue weights (mg) of punch biopsies taken from the lesion sites. The tissue samples were then quickly frozen in liquid $N_2$ and stored at −80° C.

Neutrophil infiltration was assessed by measuring myeloperoxidase activity in the punch biopsy samples as described (see Bradley et al., *J. Invest. Dermatol.* 78:206-209, 1982) using the Myeloperoxidase Assay Kit from Cytostore (Calgary, Alberta Canada).

Results and Discussion

To evaluate the relative efficacy of native FcγRIA soluble receptor and the hybrid FcγR soluble receptors, FcγRIA/1A and FcγRIIIA/IA, on immune complex precipitation, an anti-OVA/OVA immune complex precipitation assay was established based on the methods of MØller (*Immunology* 38:631-640, 1979) and Gavin et al., (*Clin. Exp. Immunol.* 102:620-625, 1995). Incubation of anti-OVA and OVA at 37° C. produced a time-dependent increase in optical density of the solution mixture, an observation consistent with the formation of insoluble anti-OVA/OVA immune complexes. Addition of soluble native FcγRIA at the start of the assay produced a dose-dependent reduction in optical density of the mixtures indicating an inhibition of immune complex precipitation. Immune complex precipitation was completely abolished by 1500 nM soluble FcγRIA. Similarly, both soluble hybrid receptors, FcγRIIA/IA and FcγRIIIA/IA, blocked precipitation of OVA-anti-OVA immune complexes. The dose response curves were similar for all three FcγR, indicating that the receptors had equal potency. Since the precipitation of antigen:antibody immune complexes appears to be dependent on non-covalent interactions between the antibody Fc heavy chains (MØller, *Immunology* 38:631-640, 1979) and Fcγ receptors bind to the Fc portion of antibodies (Dijstelbloem et al., *Trends Immunol.* 22, 510-516, 2001), these data suggest that soluble native FcγRIA and the soluble hybrid receptors, FcγRIIA/IA and FcγIIIA/IA, disrupt immune complex precipitation by binding to the Fc portion of the anti-OVA antibodies.

To directly evaluate the interaction of native FcγRIA and each hybrid receptor with antibody Fc, the binding of FcγR to immobilized human IgG1 was assessed by surface plasmon resonance analyses. A monoclonal human IgG1 antibody was immobilized to the sensor surface in a single flow cell at an RU (resonance units) level of 485, a density level within optimal levels for kinetic analysis of FcγR, presuming a binding stoichiometry of one FcγR molecule with one IgG1 molecule (Woof and Burton, *Nature Rev. Immunol.* 4:1-11, 2004). Native FcγRIA soluble receptor rapidly bound to immobilized IgG1 with rates of association and dissociation of $2.8 \times 10^6$ $M^{-1}s^{-1}$ and $4.6 \times 10^{-4}$ $s^{-1}$, respectively, values which yield a calculated equilibrium dissociation constant of $1.7 \times 10^{-10}$ M. These data are similar to those reported previously (Paetz et al., *Biochem. Biophys. Res. Commun.* 338:1811-1817, 2005) and demonstrate that soluble native FcγRIA binds with high affinity to human IgG1. The soluble hybrid receptors, FcγRII/IA and FcγRIIIA/IA, rapidly bound to immobilized IgG1 with rates of association and dissociation similar to that of native FcγRIA. These data indicate that the hybrid receptors bound to immobilized human IgG1 with high affinity.

Mast cells are thought to mediate immune complex-mediated inflammation in a variety of immune disorders such as type III hypersensitivity reactions (Ravetch, *J. Clin. Invest.* 110:1759-1761, 2002; Sylvestre and Ravetch, *Immunity* 5:387-390, 1996; Jancar and Crespo, *Trends Immunology* 26:48-55, 2005). Binding of immune complexes to mast cell Fcγ receptors is thought to induce the secretion of pro-inflammatory cytokines, such as IL-6 and TNFα (Ravetch, supra; Jancar and Crespo, supra), which subsequently leads to neutrophil infiltration and tissue damage. To evaluate whether cytokine secretion from mast cells could be stimulated by immune complexes, the murine mast cell line MC/9 was incubated in the presence and absence of preformed rabbit anti-OVA/OVA immune complexes. Incubation with anti-OVA/OVA immune complexes produced a time and concentration dependent increase in the accumulation of the inflammatory cytokines IL-6, IL-13, TNFα, and MCP-1 within the MC/9 cell conditioned media. Cytokine production was not altered, in contrast, when MC/9 cells were incubated with an equivalent concentration of rabbit anti-OVA IgG alone. These data demonstrate that MC/9 cells respond to immune complexes by the production of inflammatory cytokines.

Incubation of MC/9 cells with anti-OVA/OVA immune complexes in the presence of increasing amounts of native FcγRIA soluble receptor or one of the hybrid soluble receptors, FcγRIIA/IA or FcγRIIIA/IA, produced dose-dependent reductions in the accumulation of IL-6, IL-13, TNFα, and MCP-1 (see FIG. 13). Little or no differences in the dose response curves for each receptor was noted, indicating identical potencies for each of the receptors. These data demonstrate that native FcγRIA and the hybrid soluble receptors can block the binding and signalling of immune complexes in mouse mast cells.

The findings described above demonstrate that soluble native FcγRIA and the soluble hybrid receptors, FcγRIIA/IA and FcγRIIIA/IA, can block the formation of immune complexes in vitro and can inhibit immune complex-mediated signaling in mast cells. These data suggest that the FcγR may be effective at blocking immune complex-mediated inflammation in an in vivo setting. To test this, the cutaneous reversed passive Arthus reaction was established in mice and the effects of each of the FcγR on immune complex-mediated edema and neutrophil infiltration were assessed.

Relative to intradermal injection of an equivalent concentration of nonimmune IgG, injection of anti-OVA antibodies produced a time and concentration increase in edema within the skin of treated mice. Edema was evident as both an increase in the area of extravasation of Evan's blue dye and in tissue weights. These effects were specific for immune complexes as no edema was observed in the absence of tail vein injection of OVA. Accumulation of neutrophils within the lesion site, measured by extractable activity of myeloperoxidase, was also increased.

Figure 14A:
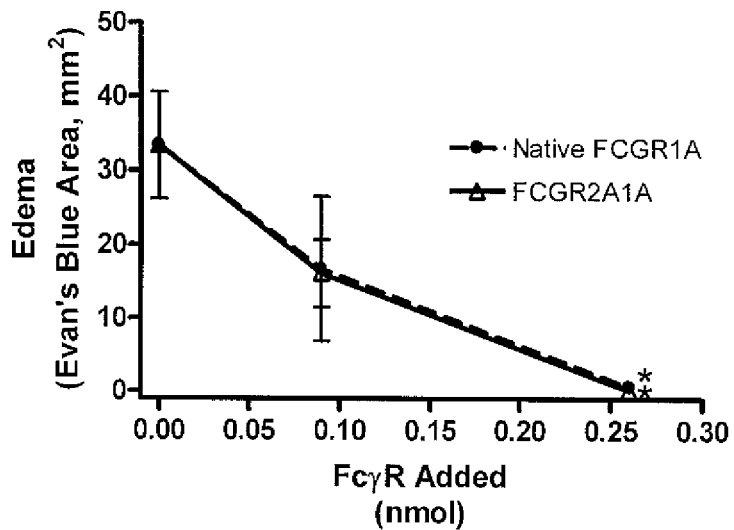
FIGS. 14A and 14B depict inhibition of immune complex-mediated edema in the murine Arthus reaction with soluble native FcγRIA and the soluble hybrid receptor, FcγRIIA/IA. The cutaneous reversed passive Arthus reaction was established in mice using intradermal delivery of rabbit anti-ovalbumin and tail vein injection of ovalbumin. (See Example 22, infra.) Animals received either anti-OVA alone or anti-OVA together with the indicated amount of soluble native FcγRIA ("Native FCGR1A"), or the soluble hybrid receptor, FcγRIIA/IA-CH6 ("FCGR2A1A"), and the effects of each soluble receptor on immune complex-mediated edema were assessed by measuring either a decrease in Evan's blue area (FIG. 14A) or a decrease in tissue weight of the lesion site (FIG. 14B). (See id.) Each point represents the mean±SD for n=6 animals per group. Differences significant relative to anti-OVA alone, *p<0.001 by ANOVA.
Figure 14B:
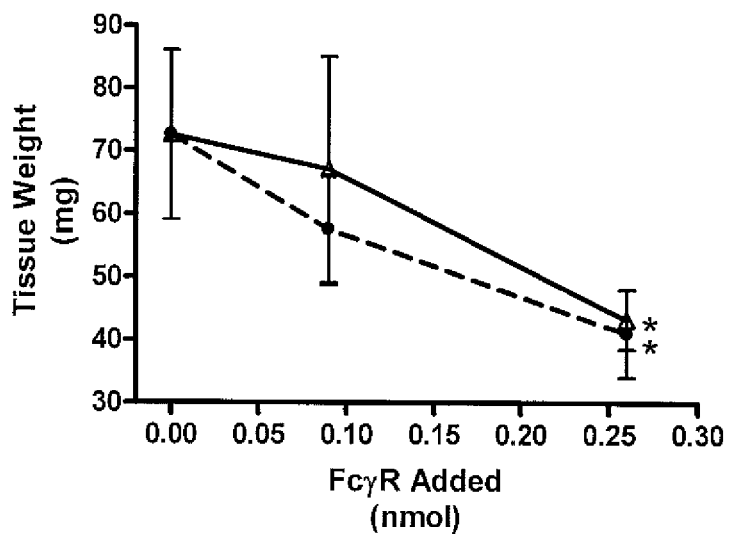
Figure 15A:
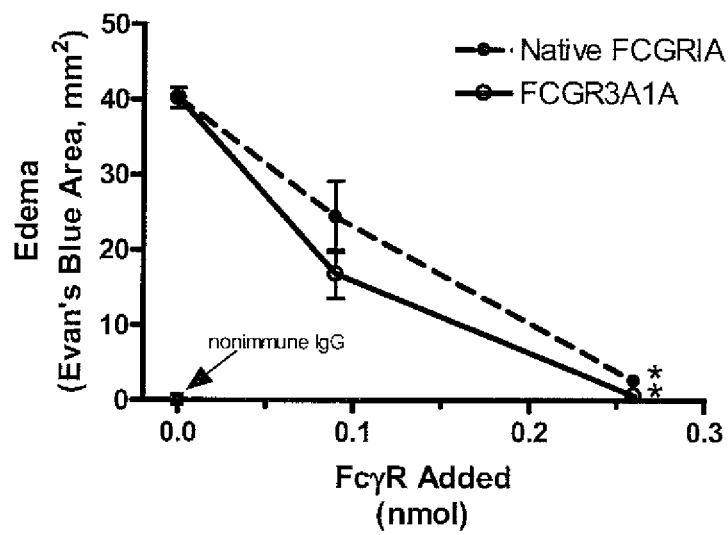
FIGS. 15A and 15B depict inhibition of immune complex-mediated edema in the cutaneous Arthus reaction in mice with soluble native FcγRIA and the soluble hybrid receptor, FcγRIIIA/IA. The cutaneous reversed passive Arthus reaction was established in mice using intradermal delivery of rabbit anti-ovalbumin and tail vein injection of ovalbumin. (See Example 22, infra.) Animals received either anti-OVA alone or anti-OVA together with the indicated amount of soluble native FcγRIA ("Native FCGR1A"), or the soluble hybrid receptor, FcγRIIIA/IA-CH6 ("FCGR3A1A"), and the effects of each soluble receptor on immune complex-mediated edema were assessed by measuring either a decrease in Evan's blue area (FIG. 15A) or a decrease in tissue weight of the lesion site (FIG. 15B). (See id.) Each point represents the mean±SD for n=6 animals per group. Difference significant, *p<0.001 by ANOVA.
Figure 15B:
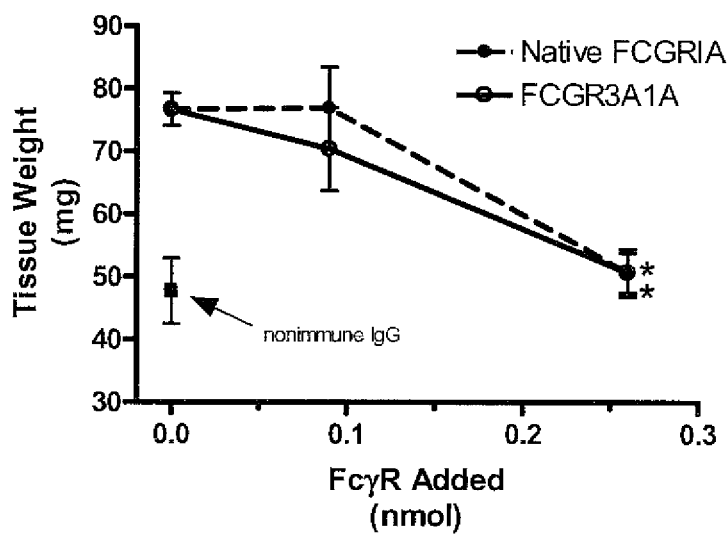

Intradermal delivery of anti-OVA antibodies with increasing amounts of soluble native FcγRIA produced a concentration-dependent reduction in edema, measured by either a decrease in Evan's blue area (FIGS. 14A and 15A) or a decrease in tissue weight of the lesion site (FIGS. 14B and 15B). Similar results were obtained using either of the soluble hybrid receptors, FcγRIIA/IA (FIGS. 14A and 14B) and FcγRIIIA/IA (FIGS. 15A and 15B).

Figure 16A:
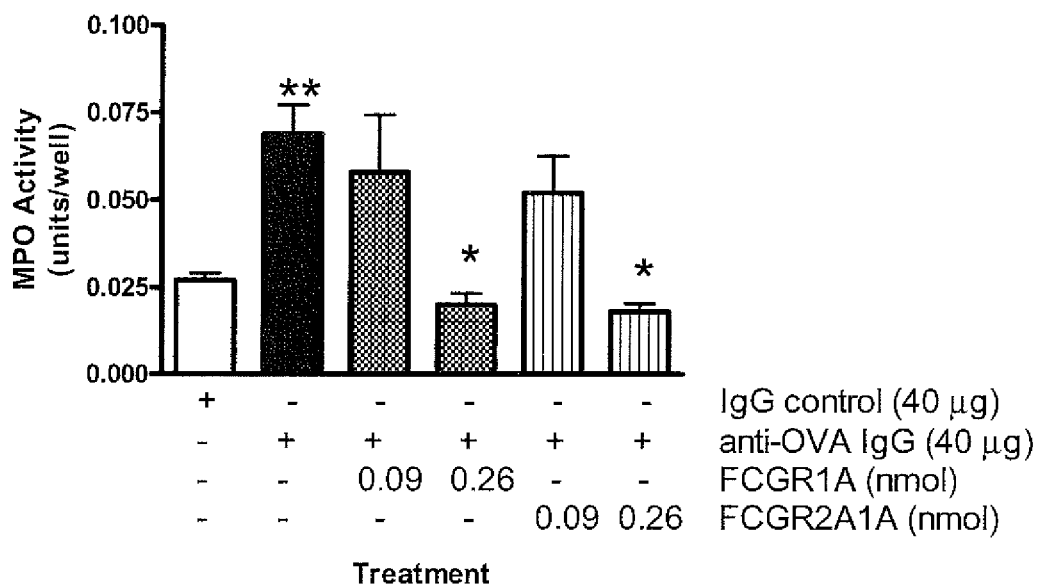
FIGS. 16A and 16B depict inhibition of neutrophil infiltration in the cutaneous Arthus reaction in mice with soluble native FcγRIA and the soluble hybrid receptors, FcγRIIA/IA-CH6 and FcγRIIIA/IA-CH6. The cutaneous reversed passive Arthus reaction was established in mice using intradermal delivery of rabbit anti-ovalbumin and tail vein injection of ovalbumin. (See Example 22, infra.) Animals received either anti-OVA alone or anti-OVA together with the indicated amount of soluble native FcγRIA ("FCGR1A"
Figure 16B:
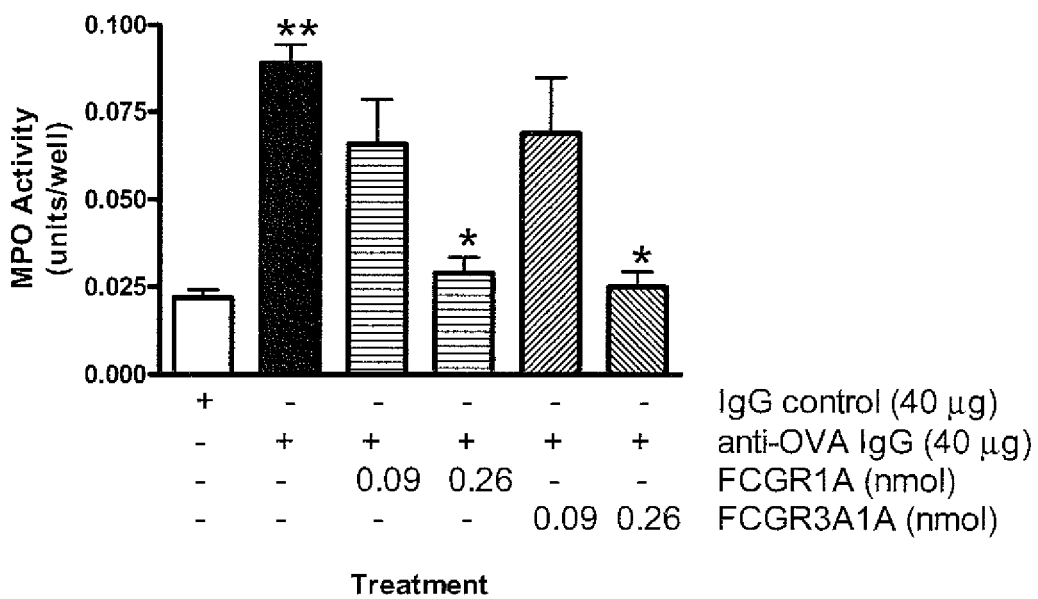

Both hybrid receptors reduced both measures of edema and were equipotent relative to native FcγRIA. Neutrophil infiltration, as measured by myeloperoxidase activity in the lesion biopsies, was also significantly decreased by soluble native FcγRIA and each soluble hybrid receptor with equivalent potencies (FIGS. 16A and 16B). These results show that soluble native FcγRIA and each soluble hybrid receptor, FcγRIIA/IA and FcγRIIIA/IA, can block edema and neutrophil infiltration in the reverse passive Arthus reaction in mice.

Although the foregoing invention has been described in detail for purposes of clarity of understanding, it will be appreciated that certain modifications may be practiced within the scope of the appended claims. All publications and patent documents cited herein are hereby incorporated by reference in their entirety for all purposes to the same extent as if each were so individually denoted.

What is claimed is:

1. An isolated, soluble polypeptide comprising an amino acid sequence selected from the group consisting of
    amino acid residues 43-310 of SEQ ID NO:42;
    amino acid residues 21-286 of SEQ ID NO:44; and
    amino acid residues 21-286 of SEQ ID NO:46;
    wherein said polypeptide is capable of specifically binding the Fc region of IgG.

2. The polypeptide of claim 1, further comprising a secretory signal sequence.

3. A composition comprising:
    an isolated polypeptide as in claim 1; and
    a pharmaceutically acceptable vehicle.

* * * * *

SEQUENCE LISTING

<160> NUMBER OF SEQ ID NOS: 66

<210> SEQ ID NO 1
<211> LENGTH: 2138
<212> TYPE: DNA
<213> ORGANISM: Homo sapien

<400> SEQUENCE: 1
cttggagaca acatgtggtt cttgacaact ctgctccttt gggttccagt tgatgggcaa    60
gtggacacca caaaggcagt gatcactttg cagcctccat gggtcagcgt gttccaagag    120

```
gaaaccgtaa ccttgcattg tgaggtgctc catctgcctg ggagcagctc tacacagtgg    180
tttctcaatg gcacagccac tcagacctcg accccccagct acagaatcac ctctgccagt   240
gtcaatgaca gtggtgaata caggtgccag agaggtctct cagggcgaag tgaccccata    300
cagctggaaa tccacagagg ctggctacta ctgcaggtct ccagcagagt cttcacggaa    360
ggagaacctc tggccttgag gtgtcatgcg tggaaggata agctggtgta caatgtgctt    420
tactatcgaa atggcaaagc ctttaagttt ttccactgga attctaacct caccattctg    480
aaaaccaaca taagtcacaa tggcacctac cattgctcag catgggaaa gcatcgctac     540 acatcagcag aatatctgt cactgtgaaa gagctatttc cagctccagt gctgaatgca    600
tctgtgacat ccccactcct ggaggggaat ctggtcaccc tgagctgtga acaaagttg    660 ctcttgcaga ggcctggttt gcagctttac ttctccttct acatgggcag caagaccctg    720
cgaggcagga acacatcctc tgaataccaa atactaactg ctagaagaga agactctggg    780
ttatactggt gcgaggctgc cacagaggat ggaaatgtcc ttaagcgcag ccctgagttg    840
gagcttcaag tgcttggcct ccagttacca actcctgtct ggtttcatgt cctttctat   900 ctggcagtgg gaataatgtt tttagtgaac actgttctct gggtgacaat acgtaaagaa   960
ctgaaaagaa agaaaaagtg ggatttagaa atctctttgg attctggtca tgagaagaag  1020
gtaatttcca gccttcaaga agacagacat ttagaagaag agctgaaatg tcaggaacaa  1080
aaagaagaac agctgcagga aggggtgcac cggaaggagc ccagggggc cacgtagcag   1140 cggctcagtg ggtggccatc gatctggacc gtcccctgcc cacttgctcc ccgtgagcac   1200
tgcgtacaaa catccaaaag ttcaacaaca ccagaactgt gtgtctcatg gtatgtaact   1260
cttaaagcaa ataaatgaac tgacttcaac tgggatacat ttggaaatgt ggtcatcaaa   1320
gatgacttga aatgaggcct actctaaaga attcttgaaa aacttacaag tcaagcctag   1380
cctgataatc ctattacata gtttgaaaaa tagtatttta tttctcagaa caaggtaaaa   1440
aggtgagtgg gtgcatatgt acagaagatt aagacagaga aacagacaga aagagacaca   1500
cacacagcca ggagtgggta gatttcaggg agacaagagg gaatagtata gacaataagg   1560
aaggaaatag tacttacaaa tgactcctaa gggactgtga gactgagagg gctcacgcct   1620
ctgtgttcag gatacttagt tcatggcttt tctctttgac tttactaaaa gagaatgtct   1680
ccatacgcgt tctaggcata caagggggta actcatgatg agaaatggat gtgttattct   1740
tgccctctct tttgaggctc tctcataacc cctctatttc tagagacaac aaaaatgctg   1800
ccagtcctag gcccctgccc tgtaggaagg cagaatgtaa ctgttctgtt tgtttaacga   1860
ttaagtccaa atctccaagt gcggcactgc aaagagacgc ttcaagtggg gagaagcggc   1920
gataccatag agtccagatc ttgcctccag agatttgctt taccttcctg attttctggt   1980
tactaattag cttcaggata cgctgctctc atacttgggc tgtagtttgg agacaaaata   2040
ttttcctgcc actgtgtaac atagctgagg taaaaactga actatgtaaa tgactctact   2100
aaaagtttag ggaaaaaaaa caggaggagt atgacaca                           2138
```

<210> SEQ ID NO 2  
<211> LENGTH: 374  
<212> TYPE: PRT  
<213> ORGANISM: Homo sapien

<400> SEQUENCE: 2

Met Trp Phe Leu Thr Thr Leu Leu Leu Trp Val Pro Val Asp Gly Gln  
1               5                   10                  15

```
Val Asp Thr Thr Lys Ala Val Ile Thr Leu Gln Pro Pro Trp Val Ser
         20                  25                  30

Val Phe Gln Glu Glu Thr Val Thr Leu His Cys Glu Val Leu His Leu
     35                  40                  45

Pro Gly Ser Ser Ser Thr Gln Trp Phe Leu Asn Gly Thr Ala Thr Gln
 50                  55                  60

Thr Ser Thr Pro Ser Tyr Arg Ile Thr Ser Ala Ser Val Asn Asp Ser
 65                  70                  75                  80

Gly Glu Tyr Arg Cys Gln Arg Gly Leu Ser Gly Arg Ser Asp Pro Ile
                 85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370

<210> SEQ ID NO 3
<211> LENGTH: 277
<212> TYPE: PRT
<213> ORGANISM: Homo sapien

<400> SEQUENCE: 3

Gln Val Asp Thr Thr Lys Ala Val Ile Thr Leu Gln Pro Pro Trp Val
1               5                   10                  15
```

```
Ser Val Phe Gln Glu Glu Thr Val Thr Leu His Cys Glu Val Leu His
             20                  25                  30

Leu Pro Gly Ser Ser Thr Gln Trp Phe Leu Asn Gly Thr Ala Thr
         35                  40                  45

Gln Thr Ser Thr Pro Ser Tyr Arg Ile Thr Ser Ala Ser Val Asn Asp
 50                  55                  60

Ser Gly Glu Tyr Arg Cys Gln Arg Gly Leu Ser Gly Arg Ser Asp Pro
 65                  70                  75                  80

Ile Gln Leu Glu Ile His Arg Gly Trp Leu Leu Leu Gln Val Ser Ser
             85                  90                  95

Arg Val Phe Thr Glu Gly Glu Pro Leu Ala Leu Arg Cys His Ala Trp
            100                 105                 110

Lys Asp Lys Leu Val Tyr Asn Val Leu Tyr Tyr Arg Asn Gly Lys Ala
            115                 120                 125

Phe Lys Phe Phe His Trp Asn Ser Asn Leu Thr Ile Leu Lys Thr Asn
130                 135                 140

Ile Ser His Asn Gly Thr Tyr His Cys Ser Gly Met Gly Lys His Arg
145                 150                 155                 160

Tyr Thr Ser Ala Gly Ile Ser Val Thr Val Lys Glu Leu Phe Pro Ala
                165                 170                 175

Pro Val Leu Asn Ala Ser Val Thr Ser Pro Leu Leu Glu Gly Asn Leu
                180                 185                 190

Val Thr Leu Ser Cys Glu Thr Lys Leu Leu Leu Gln Arg Pro Gly Leu
                195                 200                 205

Gln Leu Tyr Phe Ser Phe Tyr Met Gly Ser Lys Thr Leu Arg Gly Arg
            210                 215                 220

Asn Thr Ser Ser Glu Tyr Gln Ile Leu Thr Ala Arg Arg Glu Asp Ser
225                 230                 235                 240

Gly Leu Tyr Trp Cys Glu Ala Ala Thr Glu Asp Gly Asn Val Leu Lys
                245                 250                 255

Arg Ser Pro Glu Leu Glu Leu Gln Val Leu Gly Leu Gln Leu Pro Thr
                260                 265                 270

Pro Val Trp Phe His
            275

<210> SEQ ID NO 4
<211> LENGTH: 224
<212> TYPE: PRT
<213> ORGANISM: Homo sapien

<400> SEQUENCE: 4

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
             20                  25                  30

Val Phe Gln Glu Glu Thr Val Thr Leu His Cys Glu Val Leu His Leu
         35                  40                  45

Pro Gly Ser Ser Thr Gln Trp Phe Leu Asn Gly Thr Ala Thr Gln
 50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
             85                  90                  95

Gln Leu Glu Ile His Arg Gly Trp Leu Leu Leu Gln Val Ser Ser Arg
```

```
                    100                 105                 110
Val Phe Met Glu Gly Glu Pro Leu Ala Leu Arg Cys His Ala Trp Lys
            115                 120                 125

Asp Lys Leu Val Tyr Asn Val Leu Tyr Tyr Arg Asn Gly Lys Ala Phe
        130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Gln Tyr Thr Val Lys Glu Leu Phe Pro Ala
            180                 185                 190

Pro Val Leu Asn Ala Ser Val Thr Ser Pro Leu Leu Glu Gly Asn Leu
        195                 200                 205

Val Thr Leu Ser Cys Glu Thr Lys Leu Leu Leu Gln Arg Pro Gly Leu
    210                 215                 220

<210> SEQ ID NO 5
<211> LENGTH: 210
<212> TYPE: PRT
<213> ORGANISM: Homo sapien

<400> SEQUENCE: 5

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Pro Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Lys Gly Lys His Arg Tyr
                165                 170                 175

Thr Ser Ala Gly Ile Ser Gln Tyr Thr Val Lys Glu Leu Phe Pro Ala
            180                 185                 190

Pro Val Leu Asn Ala Ser Val Thr Ser Pro Leu Leu Gly Gly Ile Trp
        195                 200                 205

Ser Pro
    210

<210> SEQ ID NO 6
<211> LENGTH: 639
<212> TYPE: DNA
<213> ORGANISM: Homo sapien
```

<400> SEQUENCE: 6

```
atggctatgg agacccaaat gtctcagaat gtatgtccca gaaacctgtg gctgcttcaa    60
ccattgacag ttttgctgct gctggcttct gcagacagtc aagctgcagc tccccccaaag   120
gctgtgctga aacttgagcc cccgtggatc aacgtgctcc aggaggactc tgtgactctg   180
acatgccagg gggctcgcag ccctgagagc gactccattc agtggttcca caatgggaat   240
ctcattccca cccacacgca gcccagctac aggttcaagg ccaacaacaa tgacagcggg   300
gagtacacgt gccagactgg ccagaccagc ctcagcgacc ctgtgcatct gactgtgctt   360
tccgaatggc tggtgctcca gacccctcac ctggagttcc aggagggaga aaccatcatg   420
ctgaggtgcc acagctggaa ggacaagcct ctggtcaagg tcacattctt ccagaatgga   480
aaatcccaga aattctccca tttggatccc accttctcca tcccacaagc aaaccacagt   540
cacagtggtg attaccactg cacaggaaac ataggctaca cgctgttctc atccaagcct   600
gtgaccatca ctgtccaagt gcccagcatg ggcagcgga                          639
```

<210> SEQ ID NO 7
<211> LENGTH: 211
<212> TYPE: PRT
<213> ORGANISM: Homo sapien

<400> SEQUENCE: 7

```
Met Ala Met Glu Thr Gln Met Ser Gln Asn Val Cys Pro Arg Asn Leu
1               5                   10                  15

Trp Leu Gln Pro Leu Thr Val Leu Leu Leu Leu Ala Ser Ala Asp Ser
            20                  25                  30

Gln Ala Ala Ala Pro Pro Lys Ala Val Leu Lys Leu Glu Pro Pro Trp
        35                  40                  45

Ile Asn Leu Gln Glu Asp Ser Val Thr Leu Thr Cys Gln Gly Ala Arg
    50                  55                  60

Ser Pro Glu Ser Asp Ser Ile Gln Trp Phe His Asn Gly Asn Leu Ile
65                  70                  75                  80

Pro Thr His Thr Gln Pro Ser Tyr Arg Phe Lys Ala Asn Asn Asn Asp
                85                  90                  95

Ser Gly Glu Tyr Thr Cys Gln Thr Gly Gln Thr Ser Leu Ser Asp Pro
            100                 105                 110

Val His Leu Thr Val Leu Ser Glu Trp Leu Val Leu Gln Thr Pro His
        115                 120                 125

Leu Glu Phe Gln Glu Gly Glu Thr Ile Met Leu Arg Cys His Ser Trp
    130                 135                 140

Lys Asp Lys Pro Leu Val Lys Val Thr Phe Phe Gln Asn Gly Lys Ser
145                 150                 155                 160

Gln Lys Phe Ser His Leu Asp Pro Thr Phe Ser Ile Pro Gln Ala Asn
                165                 170                 175

His Ser His Ser Gly Asp Tyr His Cys Thr Gly Asn Ile Gly Tyr Thr
            180                 185                 190

Leu Phe Ser Ser Lys Pro Val Thr Ile Thr Val Gln Val Pro Ser Met
    195                 200                 205

Gly Ser
210
```

<210> SEQ ID NO 8
<211> LENGTH: 651
<212> TYPE: DNA
<213> ORGANISM: Homo sapien

<400> SEQUENCE: 8

```
atgggaatcc tgtcattctt acctgtcctt gccactgaga gtgactgggc tgactgcaag      60
tccccccagc cttggggtca tatgcttctg tggacagctg tgctattcct ggctcctgtt     120
gctgggacac ctgcagctcc cccaaaggct gtgctgaaac tcgaccccca gtggatcaac     180
gtgctccagg aggactctgt gactctgaca tgccggggga ctcacagccc tgagagcgac     240
tccattcagt ggttccacaa tgggaatctc attcccaccc acacgcagcc cagctacagg     300
ttcaaggcca acaacaatga cagcggggag tacacgtgcc agactggcca gaccagcctc     360
agcgaccctg tgcatctgac tgtgctttct gagtggctgg tgctccagac ccctcacctg     420
gagttccagg agggagaaac catcgtgctg aggtgccaca gctggaagga caagcctctg     480
gtcaaggtca cattcttcca gaatggaaaa tccaagaaat tttcccgttc ggatcccaac     540
ttctccatcc cacaagcaaa ccacagtcac agtggtgatt accactgcac aggaaacata     600
ggctacacgc tgtactcatc caagcctgtg accatcactg tccaagctgg a              651
```

<210> SEQ ID NO 9
<211> LENGTH: 216
<212> TYPE: PRT
<213> ORGANISM: Homo sapien

<400> SEQUENCE: 9

```
Met Gly Ile Leu Ser Phe Leu Pro Val Leu Ala Thr Glu Ser Asp Trp
1               5                   10                  15
Ala Asp Cys Lys Ser Pro Gln Pro Trp Gly His Met Leu Leu Trp Thr
            20                  25                  30
Ala Val Leu Phe Leu Ala Pro Val Ala Gly Thr Pro Ala Ala Pro Pro
        35                  40                  45
Lys Ala Val Leu Lys Leu Glu Pro Gln Trp Ile Asn Val Leu Gln Glu
    50                  55                  60
Asp Ser Val Thr Leu Thr Cys Arg Gly Thr His Ser Pro Glu Ser Asp
65                  70                  75                  80
Ser Ile Gln Trp Phe His Asn Gly Asn Leu Ile Pro Thr His Thr Gln
                85                  90                  95
Pro Ser Tyr Arg Phe Lys Ala Asn Asn Asn Asp Ser Gly Glu Tyr Thr
            100                 105                 110
Cys Gln Thr Gly Gln Thr Ser Leu Ser Asp Pro Val His Leu Thr Val
        115                 120                 125
Leu Ser Glu Trp Leu Val Leu Gln Thr Pro His Leu Glu Phe Gln Glu
    130                 135                 140
Gly Glu Thr Ile Val Leu Arg Cys His Ser Trp Lys Asp Lys Pro Leu
145                 150                 155                 160
Val Lys Val Thr Phe Phe Gln Asn Gly Lys Ser Lys Lys Phe Ser Arg
                165                 170                 175
Ser Asp Pro Asn Phe Ser Ile Pro Gln Ala Asn His Ser His Ser Gly
            180                 185                 190
Asp Tyr His Cys Thr Gly Asn Ile Gly Tyr Thr Leu Tyr Ser Ser Lys
        195                 200                 205
Pro Val Thr Ile Thr Val Gln Ala
    210                 215
```

<210> SEQ ID NO 10
<211> LENGTH: 588
<212> TYPE: DNA

<213> ORGANISM: Homo sapien

<400> SEQUENCE: 10

```
atgtggcagc tgctcctccc aactgctctg ctacttctag tttcagctgg catgcggact    60
gaagatctcc caaaggctgt ggtgttcctg gagcctcaat ggtacagggt gctcgagaag   120
gacagtgtga ctctgaagtg ccagggagcc tactcccctg aggacaattc cacacagtgg   180
tttcacaatg agagcctcat ctcaagccag gcctcgagct acttcattga cgctgccaca   240
gtcgacgaca gtggagagta caggtgccag acaaacctct ccaccctcag tgacccggtg   300
cagctagaag tccatatcgg ctggctgttg ctccaggccc ctcggtgggt gttcaaggag   360
gaagacccta ttcacctgag gtgtcacagc tggaagaaca ctgctctgca taaggtcaca   420
tatttacaga atggcaaagg caggaagtat tttcatcata attctgactt ctacattcca   480
aaagccacac tcaaagacag cggctcctac ttctgcaggg ggcttgttgg gagtaaaaat   540
gtgtcttcag agactgtgaa catcaccatc actcaaggtt tggcagga                588
```

<210> SEQ ID NO 11
<211> LENGTH: 195
<212> TYPE: PRT
<213> ORGANISM: Homo sapien

<400> SEQUENCE: 11

```
Met Trp Gln Leu Leu Leu Pro Thr Ala Leu Leu Leu Val Ser Ala
1               5                  10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala
        195
```

<210> SEQ ID NO 12
<211> LENGTH: 588
<212> TYPE: DNA
<213> ORGANISM: Homo sapien

<400> SEQUENCE: 12

```
atgtggcagc tgctcctccc aactgctctg ctacttctag tttcagctgg catgcggact    60
gaagatctcc caaaggctgt ggtgttcctg gagcctcaat ggtacagggt gctcgagaag   120
gacagtgtga ctctgaagtg ccagggagcc tactcccctg aggacaattc cacacagtgg   180
tttcacaatg agaacctcat ctcaagccag gcctcgagct acttcattga cgctgccaca   240
gtcgacgaca gtggagagta caggtgccag acaaaccttct ccaccctcag tgacccggtg   300
cagctagaag tccatgtcgg ctggctgttg ctccaggccc ctcggtgggt gttcaaggag   360
gaagacccta ttcacctgag gtgtcacagc tggaagaaca ctgctctgca taaggtcaca   420
tatttacaga atggcaaaga caggaagtat tttcatcata attctgactt ccacattcca   480
aaagccacac tcaaagatag cggctcctac ttctgcaggg ggcttgttgg gagtaaaaat   540
gtgtcttcag agactgtgaa catcaccatc actcaaggtt tggcagga                588

<210> SEQ ID NO 13
<211> LENGTH: 195
<212> TYPE: PRT
<213> ORGANISM: Homo sapein

<400> SEQUENCE: 13

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Asn Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Val Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala
        195

<210> SEQ ID NO 14
<211> LENGTH: 1125
<212> TYPE: DNA
<213> ORGANISM: Homo sapien

<400> SEQUENCE: 14
atgtggttct tgacaactct gctcctttgg gttccagttg atgggcaagt ggacaccaca    60
aaggcagtga tcactttgca gcctccatgg gtcagcgtgt tccaagagga aaccgtaacc   120
```

```
ttgcattgtg aggtgctcca tctgcctggg agcagctcta cacagtggtt tctcaatggc    180
acagccactc agacctcgac ccccagctac agaatcacct ctgccagtgt caatgacagt    240
ggtgaataca ggtgccagag aggtctctca gggcgaagtg acccc ataca gctggaaatc    300 cacagaggct ggctactact gcaggtctcc agcagagtct tcacggaagg agaacctctg    360
gccttgaggt gtcatgcgtg gaaggataag ctggtgtaca atgtgcttta ctatcgaaat    420
ggcaaagcct ttaagttttt ccactggaat tctaacctca ccattctgaa aaccaacata    480
agtcacaatg gcacctacca ttgctcaggc atgggaaagc atcgctacac atcagcagga    540
atatctgtca ctgtgaaaga gctatttcca gctccagtgc tgaatgcatc tgtgacatcc    600
ccactcctgg aggggaatct ggtcaccctg agctgtgaaa caaagttgct cttgcagagg    660 cctggttttgc agctttactt ctccttctac atgggcagca agaccctgcg aggcaggaac    720
acatcctctg aataccaaat actaactgct agaagagaag actctggggtt atactggtgc    780 gaggctgcca cagaggatgg aaatgtcctt aagcgcagcc ctgagttgga gcttcaagtg    840
cttggcctcc agttaccaac tcctgtctgg tttcatgtcc ttttctatct ggcagtggga    900
ataatgtttt tagtgaacac tgttctctgg gtgacaatac gtaaagaact gaaaagaaag    960
aaaaagtggg atttagaaat ctcttttggat tctggtcatg agaagaaggt aatttccagc   1020
cttcaagaag acagacattt agaagaagag ctgaaatgtc aggaacaaaa agaagaacag   1080
ctgcaggaag gggtgcaccg gaaggagccc caggggggcca cgtag                  1125
```

<210> SEQ ID NO 15
<211> LENGTH: 7
<212> TYPE: PRT
<213> ORGANISM: Artificial Sequence
<220> FEATURE:
<223> OTHER INFORMATION: Glu-Glu tag

<400> SEQUENCE: 15

Glu Glu Tyr Met Pro Met Glu
1               5

<210> SEQ ID NO 16
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 16
acaggtgtcc agggaattca tataggccgg ccaccatgtg gttcttgaca actctg      56

<210> SEQ ID NO 17
<211> LENGTH: 79
<212> TYPE: DNA
<213> ORGANISM: Artificial Sequence
<220> FEATURE:
<223> OTHER INFORMATION: oligonucleotide primer

<400> SEQUENCE: 17 caacccc aga gctgttttaa ggcgcgcctc tagattattc catgggcatg tattcttcca   60
cttgaagctc caactcagg                                                 79

<210> SEQ ID NO 18
<211> LENGTH: 10
<212> TYPE: PRT
<213> ORGANISM: Artificial Sequence
<220> FEATURE:

<223> OTHER INFORMATION: His tag

<400> SEQUENCE: 18

Gly Ser Gly Gly His His His His His His
1               5                   10

<210> SEQ ID NO 19
<211> LENGTH: 10
<212> TYPE: PRT
<213> ORGANISM: Artificial Sequence
<220> FEATURE:
<223> OTHER INFORMATION: FLAG tag

<400> SEQUENCE: 19

Gly Ser Asp Tyr Lys Asp Asp Asp Asp Lys
1               5                   10

<210> SEQ ID NO 20
<211> LENGTH: 88
<212> TYPE: DNA
<213> ORGANISM: Artificial Sequence
<220> FEATURE:
<223> OTHER INFORMATION: oligonucleotide primer

<400> SEQUENCE: 20 caacccaga gctgttttaa ggcgcgcctc tagattagtg atggtgatgg tgatgtccac    60
cagatcccac ttgaagctcc aactcagg                                      88

<210> SEQ ID NO 21
<211> LENGTH: 88
<212> TYPE: DNA
<213> ORGANISM: Artificial Sequence
<220> FEATURE:
<223> OTHER INFORMATION: oligonucleotide primer

<400> SEQUENCE: 21 caacccaga gctgttttaa ggcgcgcctc tagattactt atcatcatca tccttataat    60
cggatcccac ttgaagctcc aactcagg                                      88

<210> SEQ ID NO 22
<211> LENGTH: 876
<212> TYPE: DNA
<213> ORGANISM: Artificial Sequence
<220> FEATURE:
<223> OTHER INFORMATION: FcyRIA-CH6 coding sequence

<400> SEQUENCE: 22
atgtggttct tgacaactct gctcctttgg gttccagttg atgggcaagt ggacaccaca    60
aaggcagtga tcactttgca gcctccatgg gtcagcgtgt tccaagagga accgtaacc   120 ttgcattgtg aggtgctcca tctgcctggg agcagctcta cacagtggtt tctcaatggc   180
acagccactc agacctcgac ccccagctac agaatcacct ctgccagtgt caatgacagt   240
ggtgaataca ggtgccagag aggtctctca gggcgaagtg accccataca gctggaaatc   300
cacagaggct ggctactact gcaggtctcc agcagagtct tcacggaagg agaacctctg   360
gccttgaggt gtcatgcgtg gaaggataag ctggtgtaca atgtgcttta ctatcgaaat   420
ggcaaagcct ttaagttttt ccactggaat tctaacctca ccattctgaa accaacata   480 agtcacaatg gcacctacca ttgctcaggc atgggaaagc atcgctacac atcagcagga   540
atatctgtca ctgtgaaaga gctatttcca gctccagtgc tgaatgcatc tgtgacatcc   600
ccactcctgg aggggaatct ggtcaccctg agctgtgaaa caagttgct cttgcagagg   660

```
cctggtttgc agctttactt ctccttctac atgggcagca agaccctgcg aggcaggaac    720
acatcctctg aataccaaat actaactgct agaagagaag actctgggtt atactggtgc    780
gaggctgcca cagaggatgg aaatgtcctt aagcgcagcc ctgagttgga gcttcaagtg    840
cttggcggat ctggtggaca tcaccatcac catcac                              876
```

<210> SEQ ID NO 23
<211> LENGTH: 292
<212> TYPE: PRT
<213> ORGANISM: Artificial Sequence
<220> FEATURE:
<223> OTHER INFORMATION: FcγRIA-CH6

<400> SEQUENCE: 23

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Gly Ser Gly Gly His His
        275                 280                 285

His His His His
    290
```

<210> SEQ ID NO 24
<211> LENGTH: 666

<212> TYPE: DNA
<213> ORGANISM: Artificial Sequence
<220> FEATURE:
<223> OTHER INFORMATION: FcyRIIA-CH6 coding sequence

<400> SEQUENCE: 24

```
atggctatgg agacccaaat gtctcagaat gtatgtccca gaaacctgtg gctgcttcaa      60
ccattgacag ttttgctgct gctggcttct gcagacagtc aagctgcagc tccccccaaag   120
gctgtgctga acttgagcc cccgtggatc aacgtgctcc aggaggactc tgtgactctg     180
acatgccagg gggctcgcag ccctgagagc gactccattc agtggttcca caatgggaat   240
ctcattccca cccacacgca gcccagctac aggttcaagg ccaacaacaa tgacagcggg    300
gagtacacgt gccagactgg ccagaccagc ctcagcgacc ctgtgcatct gactgtgctt    360
tccgaatggc tggtgctcca gaccctcac ctggagttcc aggagggaga accatcatg      420
ctgaggtgcc acagctggaa ggacaagcct ctggtcaagg tcacattctt ccagaatgga    480
aaatcccaga aattctccca tttggatccc accttctcca tcccacaagc aaaccacagt    540
cacagtggtg attaccactg cacaggaaac ataggctaca cgctgttctc atccaagcct   600
gtgaccatca ctgtccaagt gcccagcatg ggcagcggat ctggtggaca tcaccatcac   660
catcac                                                               666
```

<210> SEQ ID NO 25
<211> LENGTH: 222
<212> TYPE: PRT
<213> ORGANISM: Artificial Sequence
<220> FEATURE:
<223> OTHER INFORMATION: FcyRIIA-CH6

<400> SEQUENCE: 25

```
Met Ala Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205
```

```
Ser Met Gly Ser Gly Ser Gly Gly His His His His His His
    210                 215                 220
```

<210> SEQ ID NO 26
<211> LENGTH: 615
<212> TYPE: DNA
<213> ORGANISM: Artificial Sequence
<220> FEATURE:
<223> OTHER INFORMATION: FcyRIIIA-CH6 coding sequence

<400> SEQUENCE: 26

```
atgtggcagc tgctcctccc aactgctctg ctacttctag tttcagctgg catgcggact    60
gaagatctcc caaaggctgt ggtgttcctg gagcctcaat ggtacagggt gctcgagaag   120
gacagtgtga ctctgaagtg ccagggagcc tactccnctg aggacaattc cacacagtgg   180
tttcacaatg agagcctcat ctcaagccag gcctcgagct acttcattga cgctgccaca   240
gtcgacgaca gtggagagta caggtgccag acaaacctct ccaccctcag tgacccggtg   300
cagctagaag tccatatcgg ctggctgttg ctccaggccc ctcggtgggt gttcaaggag   360
gaagacccta ttcacctgag gtgtcacagc tggaagaaca ctgctctgca taaggtcaca   420
tatttacaga atggcaaagg caggaagtat tttcatcata attctgactt ctacattcca   480
aaagccacac tcaaagacag cggctcctac ttctgcaggg ggcttgttgg gagtaaaaat   540
gtgtcttcag agactgtgaa catcaccatc actcaaggtt tggcaggatc tggtggacat   600
caccatcacc atcac                                                    615
```

<210> SEQ ID NO 27
<211> LENGTH: 205
<212> TYPE: PRT
<213> ORGANISM: Artificial Sequence
<220> FEATURE:
<223> OTHER INFORMATION: FcyRIIIA-CH6

<400> SEQUENCE: 27

```
Met Trp Gln Leu Leu Leu Pro Thr Ala Leu Leu Leu Val Ser Ala
1               5                  10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175
```

```
Gly Ser Lys Asn Val Ser Ser Glu Thr Val Asn Ile Thr Ile Thr Gln
            180                 185                 190

Gly Leu Ala Gly Ser Gly Gly His His His His His His
        195                 200                 205

<210> SEQ ID NO 28
<211> LENGTH: 70
<212> TYPE: DNA
<213> ORGANISM: Artificial Sequence
<220> FEATURE:
<223> OTHER INFORMATION: oligonucleotide primer

<400> SEQUENCE: 28
actttgcctt tctctccaca ggtgtccagg gaattcatat aggccggcca ccatgtggtt      60
cttgacaact                                                              70

<210> SEQ ID NO 29
<211> LENGTH: 63
<212> TYPE: DNA
<213> ORGANISM: Artificial Sequence
<220> FEATURE:
<223> OTHER INFORMATION: oligonucleotide primer

<400> SEQUENCE: 29
tggggtgggt acaaccccag agctgtttta aggcgcgcct ttagccaagc acttgaagct      60
cca                                                                    63

<210> SEQ ID NO 30
<211> LENGTH: 61
<212> TYPE: DNA
<213> ORGANISM: Artificial Sequence
<220> FEATURE:
<223> OTHER INFORMATION: oligonucleotide primer

<400> SEQUENCE: 30
tggggtgggt acaaccccag agctgtttta aggcgcgcct ttaatgaaac cagacaggag      60
t                                                                      61

<210> SEQ ID NO 31
<211> LENGTH: 846
<212> TYPE: DNA
<213> ORGANISM: Homo sapien

<400> SEQUENCE: 31
atgtggttct tgacaactct gctcctttgg gttccagttg atgggcaagt ggacaccaca      60
aaggcagtga tcactttgca gcctccatgg gtcagcgtgt tccaagagga aaccgtaacc     120
ttgcattgtg aggtgctcca tctgcctggg agcagctcta cacagtggtt tctcaatggc     180
acagccactc agacctcgac ccccagctac agaatcacct ctgccagtgt caatgacagt     240
ggtgaataca ggtgccagag aggtctctca gggcgaagtg accccataca gctggaaatc     300
cacagaggct ggctactact gcaggtctcc agcagagtct tcacggaagg agaacctctg     360 gcccttgaggt gtcatgcgtg gaaggataag ctggtgtaca atgtgcttta ctatcgaaat     420
ggcaaagcct ttaagttttt ccactggaat tctaacctca ccattctgaa accaacata     480 agtcacaatg cacctacca ttgctcaggc atgggaaagc atcgctacac atcagcagga     540
atatctgtca ctgtgaaaga gctatttcca gctccagtgc tgaatgcatc tgtgacatcc     600
ccactcctgg aggggaatct ggtcaccctg agctgtgaaa caagttgct cttgcagagg     660 cctggttttg cagctttactt ctccttctac atgggcagca agaccctgcg aggcaggaac     720
```

```
acatcctctg aataccaaat actaactgct agaagagaag actctgggtt atactggtgc      780
gaggctgcca cagaggatgg aaatgtcctt aagcgcagcc ctgagttgga gcttcaagtg      840
cttggc                                                                  846
```

<210> SEQ ID NO 32
<211> LENGTH: 282
<212> TYPE: PRT
<213> ORGANISM: Homo sapien

<400> SEQUENCE: 32

```
Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly
        275                 280
```

<210> SEQ ID NO 33
<211> LENGTH: 876
<212> TYPE: DNA
<213> ORGANISM: Homo sapiens

<400> SEQUENCE: 33

```
atgtggttct tgacaactct gctcctttgg gttccagttg atgggcaagt ggacaccaca      60
```

```
aaggcagtga tcactttgca gcctccatgg gtcagcgtgt tccaagagga aaccgtaacc    120
ttgcattgtg aggtgctcca tctgcctggg agcagctcta cacagtggtt tctcaatggc    180
acagccactc agacctcgac ccccagctac agaatcacct ctgccagtgt caatgacagt    240
ggtgaataca ggtgccagag aggtctctca gggcgaagtg acccccatac agctgaaatc    300
cacagaggct ggctactact gcaggtctcc agcagagtct tcacggaagg agaacctctg    360
gccttgaggt gtcatgcgtg aaggataag ctggtgtaca atgtgcttta ctatcgaaat     420
ggcaaagcct ttaagttttt ccactggaat tctaacctca ccattctgaa aaccaacata    480
agtcacaatg gcacctacca ttgctcaggc atgggaaagc atcgctacac atcagcagga    540
atatctgtca ctgtgaaaga gctatttcca gctccagtgc tgaatgcatc tgtgacatcc    600
ccactcctgg aggggaatct ggtcaccctg agctgtgaaa caaagttgct cttgcagagg    660
cctggtttgc agctttactt ctccttctac atgggcagca agaccctgcg aggcaggaac    720
acatcctctg aataccaaat actaactgct agaagagaag actctgggtt atactggtgc    780
gaggctgcca cagaggatgg aaatgtcctt aagcgcagcc ctgagttgga gcttcaagtg    840
cttggcctcc agttaccaac tcctgtctgg tttcat                              876
```

<210> SEQ ID NO 34
<211> LENGTH: 292
<212> TYPE: PRT
<213> ORGANISM: Homo sapien

<400> SEQUENCE: 34

```
Met Trp Phe Leu Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
```

```
       225                 230                 235                 240
Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
                260                 265                 270

Ser Pro Glu Leu Glu Leu Gln Val Leu Gly Leu Gln Leu Pro Thr Pro
                275                 280                 285

Val Trp Phe His
    290
```

<210> SEQ ID NO 35
<211> LENGTH: 1392
<212> TYPE: DNA
<213> ORGANISM: Artificial Sequence
<220> FEATURE:
<223> OTHER INFORMATION: FcyRIIA-Fc5 coding sequence

<400> SEQUENCE: 35

```
atggctatgg agacccaaat gtctcagaat gtatgtccca gaaacctgtg gctgcttcaa      60
ccattgacag ttttgctgct gctggcttct gcagacagtc aagctgcagc tcccccaaag     120
gctgtgctga acttgagcc cccgtggatc aacgtgctcc aggaggactc tgtgactctg     180
acatgccagg gggctcgcag ccctgagagc gactccattc agtggttcca caatgggaat     240
ctcattccca cccacacgca gcccagctac aggttcaagg ccaacaacaa tgacagcggg     300
gagtacacgt gccagactgg ccagaccagc ctcagcgacc ctgtgcatct gactgtgctt     360
tccgaatggc tggtgctcca gaccctcac ctggagttcc aggagggaga accatcatg     420
ctgaggtgcc acagctggaa ggacaagcct ctggtcaagg tcacattctt ccagaatgga     480
aaatcccaga aattctccca tttggatccc accttctcca tcccacaagc aaaccacagt     540
cacagtggtg attaccactg cacaggaaac ataggctaca cgctgttctc atccaagcct     600
gtgaccatca ctgtccaagt gcccagcatg ggcagcggag tgggggctc cggcgggggt     660
ggaagcggtg gaggcgggtc ggggggcgga ggtagtgagc ccaaatcttc agacaaaact     720
cacacatgcc caccgtgccc agcacctgaa gccgaggggg gaccgtcagt cttcctcttc     780
ccccaaaaac ccaaggacac cctcatgatc tcccggaccc ctgaggtcac atgcgtggtg     840
gtggacgtga gccacgaaga ccctgaggtc aagttcaact ggtacgtgga cggcgtggag     900
gtgcataatg ccaagacaaa gccgcgggag gagcagtaca acagcacgta ccgtgtggtc     960
agcgtcctca ccgtcctgca ccaggactgg ctgaatggca aggagtacaa gtgcaaggtc    1020
tccaacaaag ccctcccatc ctccatcgag aaaaccatct ccaaagccaa agggcagccc    1080
cgagaaccac aggtgtacac cctgcccca tcccgggatg agctgaccaa gaaccaggtc    1140
agcctgacct gcctggtcaa aggcttctat cccagcgaca tcgccgtgga gtgggagagc    1200
aatgggcagc cggagaacaa ctacaagacc acgcctcccg tgctggactc cgacggctcc    1260
ttcttcctct acagcaagct caccgtggac aagagcaggt ggcagcaggg gaacgtcttc    1320
tcatgctccg tgatgcatga ggctctgcac aaccactaca cgcagaagag cctctccctg    1380
tctccgggta aa                                                       1392
```

<210> SEQ ID NO 36
<211> LENGTH: 464
<212> TYPE: PRT
<213> ORGANISM: Artificial Sequence
<220> FEATURE:
<223> OTHER INFORMATION: FcyRIIA-Fc5

<400> SEQUENCE: 36

```
Met Ala Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp
            20                  25                  30

Ser Gln Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
                100                 105                 110

Asp Pro Val His Leu Thr Val Leu Ser Glu Trp Leu Val Leu Gln Thr
            115                 120                 125

Pro His Leu Glu Phe Gln Glu Gly Glu Thr Ile Met Leu Arg Cys His
        130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
                180                 185                 190

Tyr Thr Leu Phe Ser Ser Lys Pro Val Thr Ile Thr Val Gln Val Pro
            195                 200                 205

Ser Met Gly Ser Gly Gly Gly Ser Gly Gly Gly Ser Gly Gly
        210                 215                 220

Gly Gly Ser Gly Gly Gly Ser Glu Pro Lys Ser Ser Asp Lys Thr
225                 230                 235                 240

His Thr Cys Pro Pro Cys Pro Ala Pro Glu Ala Glu Gly Ala Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ser Ser Ile Glu Lys Thr
                340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
        370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
```

<210> SEQ ID NO 37
<211> LENGTH: 1341
<212> TYPE: DNA
<213> ORGANISM: Artificial Sequence
<220> FEATURE:
<223> OTHER INFORMATION: FcyRIIIA-Fc5 coding sequence

<400> SEQUENCE: 37

```
atgtggcagc tgctcctccc aactgctctg ctacttctag tttcagctgg catgcggact      60
gaagatctcc caaaggctgt ggtgttcctg gagcctcaat ggtacagggt gctcgagaag     120
acagtgtga ctctgaagtg ccagggagcc tactcccctg aggacaattc cacacagtgg     180
tttcacaatg agagcctcat ctcaagccag gcctcgagct acttcattga cgctgccaca     240
gtcgacgaca gtggagagta caggtgccag acaaacctct ccaccctcag tgacccggtg     300
cagctagaag tccatatcgg ctggctgttg ctccaggccc ctcggtgggt gttcaaggag     360
gaagacccta ttcacctgag gtgtcacagc tggaagaaca ctgctctgca taaggtcaca     420
tatttacaga atggcaaagg caggaagtat tttcatcata attctgactt ctacattcca     480
aaagccacac tcaaagacag cggctcctac ttctgcaggg ggcttgttgg gagtaaaaat     540
gtgtcttcag agactgtgaa catcaccatc actcaaggtt tggcaggagg tgggggctcc     600
ggcggggtg gaagcggtgg aggcgggtcg ggggcggag gtagtgagcc caaatcttca     660
gacaaaactc acacatgccc accgtgccca gcacctgaag ccgaggggc accgtcagtc     720
ttcctcttcc cccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccatcc tccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctcctgt ctccgggtaa a                                              1341
```

<210> SEQ ID NO 38
<211> LENGTH: 447
<212> TYPE: PRT
<213> ORGANISM: Artificial Sequence
<220> FEATURE:
<223> OTHER INFORMATION: FcyRIIA-Fc5

<400> SEQUENCE: 38

Met Trp Gln Leu Leu Leu Pro Thr Ala Leu Leu Leu Leu Val Ser Ala
1               5                   10                  15

-continued

```
Gly Met Arg Thr Glu Asp Leu Pro Lys Ala Val Val Phe Leu Glu Pro
             20                  25                  30

Gln Trp Tyr Arg Val Leu Glu Lys Asp Ser Val Thr Leu Lys Cys Gln
         35                  40                  45

Gly Ala Tyr Ser Pro Glu Asp Asn Ser Thr Gln Trp Phe His Asn Glu
 50                  55                  60

Ser Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
             100                 105                 110

Ala Pro Arg Trp Val Phe Lys Glu Glu Asp Pro Ile His Leu Arg Cys
         115                 120                 125

His Ser Trp Lys Asn Thr Ala Leu His Lys Val Thr Tyr Leu Gln Asn
 130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                 165                 170                 175

Gly Ser Lys Asn Val Ser Ser Glu Thr Val Asn Ile Thr Ile Thr Gln
             180                 185                 190

Gly Leu Ala Gly Gly Gly Gly Ser Gly Gly Gly Ser Gly Gly Gly
         195                 200                 205

Gly Ser Gly Gly Gly Ser Glu Pro Lys Ser Ser Asp Lys Thr His
 210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser His Glu Asp Pro Glu
             260                 265                 270

Val Lys Phe Asn Trp Tyr Val Asp Gly Val Glu Val His Asn Ala Lys
         275                 280                 285

Thr Lys Pro Arg Glu Glu Gln Tyr Asn Ser Thr Tyr Arg Val Val Ser
 290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ser Ser Ile Glu Lys Thr Ile
                 325                 330                 335

Ser Lys Ala Lys Gly Gln Pro Arg Glu Pro Gln Val Tyr Thr Leu Pro
             340                 345                 350

Pro Ser Arg Asp Glu Leu Thr Lys Asn Gln Val Ser Leu Thr Cys Leu
         355                 360                 365

Val Lys Gly Phe Tyr Pro Ser Asp Ile Ala Val Glu Trp Glu Ser Asn
 370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                 405                 410                 415

Trp Gln Gln Gly Asn Val Phe Ser Cys Ser Val Met His Glu Ala Leu
             420                 425                 430
```

His Asn His Tyr Thr Gln Lys Ser Leu Ser Leu Ser Pro Gly Lys
            435                 440                 445

<210> SEQ ID NO 39
<211> LENGTH: 936
<212> TYPE: DNA
<213> ORGANISM: Artificial Sequence
<220> FEATURE:
<223> OTHER INFORMATION: FcyRIIA/IA-CH6 coding sequence

<400> SEQUENCE: 39

```
atggctatgg agacccaaat gtctcagaat gtatgtccca gaaacctgtg gctgcttcaa      60
ccattgacag ttttgctgct gctggcttct gcagacagtc aagctgcagc tcccccaaag     120
gctgtgctga acttgagcc cccgtggatc aacgtgctcc aggaggactc tgtgactctg     180
acatgccagg gggctcgcag ccctgagagc gactccattc agtggttcca caatgggaat     240
ctcattccca cccacacgca gcccagctac aggttcaagg ccaacaacaa tgacagcggg     300
gagtacacgt gccagactgg ccagaccagc ctcagcgacc ctgtgcatct gactgtgctt     360
tccgaatggc tactactgca ggtctccagc agagtcttca cggaaggaga acctctggcc     420
ttgaggtgtc atgcgtggaa ggataagctg gtgtacaatg tgctttacta tcgaaatggc     480
aaagccttta gttttttcca ctggaattct aacctcacca ttctgaaaac caacataagt     540
cacaatggca cctaccattg ctcaggcatg ggaaagcatc gctacacatc agcaggaata     600
tctgtcactg tgaaagagct atttccagct ccagtgctga atgcatctgt gacatcccca     660
ctcctggagg ggaatctggt caccctgagc tgtgaaacaa agttgctctt gcagaggcct     720
ggtttgcagc tttacttctc cttctacatg ggcagcaaga cctgcgagg caggaacaca     780
tcctctgaat accaaatact aactgctaga agagaagact ctgggttata ctggtgcgag     840
gctgccacag aggatggaaa tgtccttaag cgcagccctg agttggagct tcaagtgctt     900
ggcggatctg gtggacatca ccatcaccat cactaa                               936
```

<210> SEQ ID NO 40
<211> LENGTH: 311
<212> TYPE: PRT
<213> ORGANISM: Artificial Sequence
<220> FEATURE:
<223> OTHER INFORMATION: FcyRIIA/IA-CH6

<400> SEQUENCE: 40

Met Ala Met Glu Thr Gln Met Ser Gln Asn Val Cys Pro Arg Asn Leu
1               5                   10                  15

Trp Leu Leu Gln Pro Leu Thr Val Leu Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Leu Leu Gln Val
        115                 120                 125

```
Ser Ser Arg Val Phe Thr Glu Gly Glu Pro Leu Ala Leu Arg Cys His
    130                 135                 140

Ala Trp Lys Asp Lys Leu Val Tyr Asn Val Leu Tyr Tyr Arg Asn Gly
145                 150                 155                 160

Lys Ala Phe Lys Phe His Trp Asn Ser Asn Leu Thr Ile Leu Lys
            165                 170                 175

Thr Asn Ile Ser His Asn Gly Thr Tyr His Cys Ser Gly Met Gly Lys
            180                 185                 190

His Arg Tyr Thr Ser Ala Gly Ile Ser Val Thr Val Lys Glu Leu Phe
        195                 200                 205

Pro Ala Pro Val Leu Asn Ala Ser Val Thr Ser Pro Leu Leu Glu Gly
210                 215                 220

Asn Leu Val Thr Leu Ser Cys Glu Thr Lys Leu Leu Leu Gln Arg Pro
225                 230                 235                 240

Gly Leu Gln Leu Tyr Phe Ser Phe Tyr Met Gly Ser Lys Thr Leu Arg
                245                 250                 255

Gly Arg Asn Thr Ser Ser Glu Tyr Gln Ile Leu Thr Ala Arg Arg Glu
            260                 265                 270

Asp Ser Gly Leu Tyr Trp Cys Glu Ala Ala Thr Glu Asp Gly Asn Val
        275                 280                 285

Leu Lys Arg Ser Pro Glu Leu Glu Leu Gln Val Leu Gly Gly Ser Gly
290                 295                 300

Gly His His His His His His
305                 310

<210> SEQ ID NO 41
<211> LENGTH: 963
<212> TYPE: DNA
<213> ORGANISM: Artificial Sequence
<220> FEATURE:
<223> OTHER INFORMATION: FcγRIIB/IA-CH6 coding sequence

<400> SEQUENCE: 41
atgggaatcc tgtcattctt acctgtcctt gccactgaga gtgactgggc tgactgcaag    60
tcccccagc cttggggtca tatgcttctg tggacagctg tgctattcct ggctcctgtt    120
gctgggacac ctgcagctcc cccaaaggct gtgctgaaac tcgagcccca gtggatcaac    180
gtgctccagg aggactctgt gactctgaca tgccggggga ctcacagccc tgagagcgac    240
tccattcagt ggttccacaa tgggaatctc attccaccc acacgcagcc cagctacagg    300
ttcaaggcca caacaatga cagcggggag tacacgtgcc agactggcca gaccagcctc    360
agcgaccctg tgcatctgac tgtgctttct gagtggctac tactgcaggt ctccagagac    420
gtcttcacgg aaggagaacc tctggcctttg aggtgtcatg cgtggaagga taagctggtg    480
tacaatgtgc tttactatcg aaatggcaaa gcctttaagt ttttccactg gaattctaac    540
ctcaccattc tgaaaaccaa cataagtcac aatggcacct accattgctc aggcatggga    600
aagcatcgct acacatcagc aggaatatct gtcactgtga agagctatt tccagctcca    660
gtgctgaatg catctgtgac atccccactc ctggagggga atctggtcac cctgagctgt    720
gaaacaaagt tgctcttgca gaggcctggt ttgcagcttt acttctcctt ctacatgggc    780
agcaagaccc tgcgaggcag gaacacatcc tctgaatacc aaatactaac tgctagaaga    840
gaagactctg ggttatactg gtgcgaggct gccacagagg atggaaatgt ccttaagcgc    900
agccctgagt tggagcttca agtgcttggc ggatctggtg gacatcacca tcaccatcac    960
taa                                                                  963
```

<210> SEQ ID NO 42
<211> LENGTH: 320
<212> TYPE: PRT
<213> ORGANISM: Artificial Sequence
<220> FEATURE:
<223> OTHER INFORMATION: FcyRIIB/IA-CH6

<400> SEQUENCE: 42

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Leu Leu Gln Val Ser Ser Arg Val Phe Thr Glu
    130                 135                 140

Gly Glu Pro Leu Ala Leu Arg Cys His Ala Trp Lys Asp Lys Leu Val
145                 150                 155                 160

Tyr Asn Val Leu Tyr Tyr Arg Asn Gly Lys Ala Phe Lys Phe Phe His
                165                 170                 175

Trp Asn Ser Asn Leu Thr Ile Leu Lys Thr Asn Ile Ser His Asn Gly
            180                 185                 190

Thr Tyr His Cys Ser Gly Met Gly Lys His Arg Tyr Thr Ser Ala Gly
        195                 200                 205

Ile Ser Val Thr Val Lys Glu Leu Phe Pro Ala Pro Val Leu Asn Ala
    210                 215                 220

Ser Val Thr Ser Pro Leu Leu Glu Gly Asn Leu Val Thr Leu Ser Cys
225                 230                 235                 240

Glu Thr Lys Leu Leu Leu Gln Arg Pro Gly Leu Gln Leu Tyr Phe Ser
                245                 250                 255

Phe Tyr Met Gly Ser Lys Thr Leu Arg Gly Arg Asn Thr Ser Ser Glu
            260                 265                 270

Tyr Gln Ile Leu Thr Ala Arg Arg Glu Asp Ser Gly Leu Tyr Trp Cys
        275                 280                 285

Glu Ala Ala Thr Glu Asp Gly Asn Val Leu Lys Arg Ser Pro Glu Leu
    290                 295                 300

Glu Leu Gln Val Leu Gly Gly Ser Gly Gly His His His His His His
305                 310                 315                 320
```

<210> SEQ ID NO 43
<211> LENGTH: 891
<212> TYPE: DNA
<213> ORGANISM: Artificial Sequence
<220> FEATURE:
<223> OTHER INFORMATION: FcyRIIIA/IA-CH6 coding sequence

<400> SEQUENCE: 43

```
atgtggcagc tgctcctccc aactgctctg ctacttctag tttcagctgg catgcggact      60
gaagatctcc caaaggctgt ggtgttcctg gagcctcaat ggtacagggt gctcgagaag     120
gacagtgtga ctctgaagtg ccagggagcc tactccctg aggacaattc acacagtgg      180
tttcacaatg agagcctcat ctcaagccag gcctcgagct acttcattga cgctgccaca     240
gtcgacgaca gtggagagta caggtgccag acaaacctct ccaccctcag tgacccggtg     300
cagctagaag tccatatcgg ctggctacta ctgcaggtct ccagcagagt cttcacggaa     360
ggagaacctc tggccttgag gtgtcatgcg tggaaggata agctggtgta caatgtgctt     420
tactatcgaa atggcaaagc ctttaagttt ttccactgga attctaacct caccattctg     480
aaaaccaaca taagtcacaa tggcacctac cattgctcag gcatgggaaa gcatcgctac     540
acatcagcag gaatatctgt cactgtgaaa gagctatttc cagctccagt gctgaatgca     600
tctgtgacat ccccactcct ggagggaat ctggtcaccc tgagctgtga acaaagttg      660
ctcttgcaga ggcctggttt gcagctttac ttctccttct acatgggcag caagaccctg     720
cgaggcagga acacatcctc tgaataccaa atactaactg ctagaagaga agactctggg     780
ttatactggt gcgaggctgc cacagaggat ggaaatgtcc ttaagcgcag ccctgagttg     840
gagcttcaag tgcttggcgg atctggtgga catcaccatc accatcacta a            891
```

<210> SEQ ID NO 44
<211> LENGTH: 296
<212> TYPE: PRT
<213> ORGANISM: Artificial Sequence
<220> FEATURE:
<223> OTHER INFORMATION: FcγRIIIA/IA-CH6

<400> SEQUENCE: 44

```
Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Val Ser Ser Arg Val Phe Thr Glu Gly Glu Pro Leu Ala Leu Arg Cys
        115                 120                 125

His Ala Trp Lys Asp Lys Leu Val Tyr Asn Val Leu Tyr Tyr Arg Asn
    130                 135                 140

Gly Lys Ala Phe Lys Phe Phe His Trp Asn Ser Asn Leu Thr Ile Leu
145                 150                 155                 160

Lys Thr Asn Ile Ser His Asn Gly Thr Tyr His Cys Ser Gly Met Gly
                165                 170                 175

Lys His Arg Tyr Thr Ser Ala Gly Ile Ser Val Thr Val Lys Glu Leu
            180                 185                 190

Phe Pro Ala Pro Val Leu Asn Ala Ser Val Thr Ser Pro Leu Leu Glu
```

```
                    195                 200                 205
Gly Asn Leu Val Thr Leu Ser Cys Glu Thr Lys Leu Leu Gln Arg
    210                 215                 220

Pro Gly Leu Gln Leu Tyr Phe Ser Phe Tyr Met Gly Ser Lys Thr Leu
225                 230                 235                 240

Arg Gly Arg Asn Thr Ser Ser Glu Tyr Gln Ile Leu Thr Ala Arg Arg
                245                 250                 255

Glu Asp Ser Gly Leu Tyr Trp Cys Glu Ala Ala Thr Glu Asp Gly Asn
                260                 265                 270

Val Leu Lys Arg Ser Pro Glu Leu Glu Leu Gln Val Leu Gly Gly Ser
            275                 280                 285

Gly Gly His His His His His His
        290                 295

<210> SEQ ID NO 45
<211> LENGTH: 891
<212> TYPE: DNA
<213> ORGANISM: Artificial Sequence
<220> FEATURE:
<223> OTHER INFORMATION: FcyRIIIB/IA-CH6 coding sequence

<400> SEQUENCE: 45
atgtggcagc tgctcctccc aactgctctg ctacttctag tttcagctgg catgcggact      60
gaagatctcc caaaggctgt ggtgttcctg gagcctcaat ggtacagggt gctcgagaag     120
gacagtgtga ctctgaagtg ccagggagcc tactcccctg aggacaattc cacacagtgg    180
tttcacaatg agaacctcat ctcaagccag gcctcgagct acttcattga cgctgccaca    240
gtcgacgaca gtggagagta caggtgccag acaaacctct ccaccctcag tgacccggtg    300
cagctagaag tccatgtcgg ctggctacta ctgcaggtct ccagcagagt cttcacggaa    360
ggagaacctc tggccttgag gtgtcatgcg tggaaggata agctggtgta caatgtgctt    420
tactatcgaa atggcaaagc ctttaagttt ttccactgga attctaacct caccattctg    480
aaaaccaaca taagtcacaa tggcacctac cattgctcag catgggaaa gcatcgctac    540
acatcagcag gaatatctgt cactgtgaaa gagctatttc cagctccagt gctgaatgca    600
tctgtgacat ccccactcct ggagggaat ctggtcaccc tgagctgtga aacaaagttg    660
ctcttgcaga ggcctggttt gcagctttac ttctccttct acatgggcag caagaccctg    720
cgaggcagga acacatcctc tgaataccaa atactaactg ctagaagaga agactctggg    780
ttatactggt gcgaggctgc cacagaggat ggaaatgtcc ttaagcgcag ccctgagttg    840
gagcttcaag tgcttggcgg atctggtgga catcaccatc accatcacta a             891

<210> SEQ ID NO 46
<211> LENGTH: 296
<212> TYPE: PRT
<213> ORGANISM: Artificial Sequence
<220> FEATURE:
<223> OTHER INFORMATION: FcyRIIIB/IA-CH6

<400> SEQUENCE: 46

Met Trp Gln Leu Leu Leu Pro Thr Ala Leu Leu Leu Val Ser Ala
1                5                  10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45
```

Gly Ala Tyr Ser Pro Glu Asp Asn Ser Thr Gln Trp Phe His Asn Glu
        50                  55                  60

Asn Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Val Gly Trp Leu Leu Leu Gln
            100                 105                 110

Val Ser Ser Arg Val Phe Thr Glu Gly Glu Pro Leu Ala Leu Arg Cys
        115                 120                 125

His Ala Trp Lys Asp Lys Leu Val Tyr Asn Val Leu Tyr Tyr Arg Asn
130                 135                 140

Gly Lys Ala Phe Lys Phe Phe His Trp Asn Ser Asn Leu Thr Ile Leu
145                 150                 155                 160

Lys Thr Asn Ile Ser His Asn Gly Thr Tyr His Cys Ser Gly Met Gly
                165                 170                 175

Lys His Arg Tyr Thr Ser Ala Gly Ile Ser Val Thr Val Lys Glu Leu
            180                 185                 190

Phe Pro Ala Pro Val Leu Asn Ala Ser Val Thr Ser Pro Leu Leu Glu
        195                 200                 205

Gly Asn Leu Val Thr Leu Ser Cys Glu Thr Lys Leu Leu Leu Gln Arg
210                 215                 220

Pro Gly Leu Gln Leu Tyr Phe Ser Phe Tyr Met Gly Ser Lys Thr Leu
225                 230                 235                 240

Arg Gly Arg Asn Thr Ser Ser Glu Tyr Gln Ile Leu Thr Ala Arg Arg
                245                 250                 255

Glu Asp Ser Gly Leu Tyr Trp Cys Glu Ala Ala Thr Glu Asp Gly Asn
            260                 265                 270

Val Leu Lys Arg Ser Pro Glu Leu Glu Leu Gln Val Leu Gly Gly Ser
        275                 280                 285

Gly Gly His His His His His His
    290                 295

<210> SEQ ID NO 47
<211> LENGTH: 59
<212> TYPE: DNA
<213> ORGANISM: Artificial Sequence
<220> FEATURE:
<223> OTHER INFORMATION: forward primer specific for FcyRIIA leader
      sequence

<400> SEQUENCE: 47
tccacaggtg tccagggaat tcatataggc cggccatggc tatggagacc caaatgtct      59

<210> SEQ ID NO 48
<211> LENGTH: 58
<212> TYPE: DNA
<213> ORGANISM: Artificial Sequence
<220> FEATURE:
<223> OTHER INFORMATION: forward primer specific for FcyRIIB leader
      sequence

<400> SEQUENCE: 48
tccacaggtg tccagggaat tcatataggc cggccatggg aatcctgtca ttcttacc       58

<210> SEQ ID NO 49
<211> LENGTH: 59
<212> TYPE: DNA
<213> ORGANISM: Artificial Sequence

```
<220> FEATURE:
<223> OTHER INFORMATION: forward primer specific for FcyRIIIA leader
      sequences

<400> SEQUENCE: 49
tccacaggtg tccagggaat tcatataggc cggccatgtg gcagctgctc ctcccaact        59

<210> SEQ ID NO 50
<211> LENGTH: 60
<212> TYPE: DNA
<213> ORGANISM: Artificial Sequence
<220> FEATURE:
<223> OTHER INFORMATION: reverse primer specific for first Ig domain of
      FcyRIIA and FcyRIIB and which includes sequence overlap with
      second Ig domain of FcgRIA

<400> SEQUENCE: 50
cgtgaagact ctgctggaga cctgcagtag tagccattcg gaaagcacag tcagatgcac       60

<210> SEQ ID NO 51
<211> LENGTH: 60
<212> TYPE: DNA
<213> ORGANISM: Artificial Sequence
<220> FEATURE:
<223> OTHER INFORMATION: reverse primer specific for first Ig domain of
      FcyRIIIA and which includes sequence overlap with second Ig domain
      of FcgRIA

<400> SEQUENCE: 51
cgtgaagact ctgctggaga cctgcagtag tagccagccg atatggactt ctagctgcac       60

<210> SEQ ID NO 52
<211> LENGTH: 60
<212> TYPE: DNA
<213> ORGANISM: Artificial Sequence
<220> FEATURE:
<223> OTHER INFORMATION: reverse primer specific for first Ig domain of
      FcyRIIIB and which includes sequence overlap with second Ig domain
      of FcgRIA

<400> SEQUENCE: 52
cgtgaagact ctgctggaga cctgcagtag tagccagccg acatggactt ctagctgcac       60

<210> SEQ ID NO 53
<211> LENGTH: 60
<212> TYPE: DNA
<213> ORGANISM: Artificial Sequence
<220> FEATURE:
<223> OTHER INFORMATION: forward primer specific for second Ig domain of
      FcyRIA and which includes sequence overlap with the first Ig
      domain of FcyRIIA and FcyRIIB

<400> SEQUENCE: 53
ctcagcgacc ctgtgcatct gactgtgctt tccgaatggc tactactgca ggtctccagc       60

<210> SEQ ID NO 54
<211> LENGTH: 60
<212> TYPE: DNA
<213> ORGANISM: Artificial Sequence
<220> FEATURE:
<223> OTHER INFORMATION: forward primer specific for second Ig domain of
      FcyRIA and which includes sequence overlap with the first Ig
      domain of FcyRIIIB

<400> SEQUENCE: 54
ctcagtgacc cggtgcagct agaagtccat atcggctggc tactactgca ggtctccagc       60
```

```
<210> SEQ ID NO 55
<211> LENGTH: 60
<212> TYPE: DNA
<213> ORGANISM: Artificial Sequence
<220> FEATURE:
<223> OTHER INFORMATION: forward primer specific for second Ig domain of
      FcyRIA and which includes sequence overlap with the first Ig
      domain of FcyRIIIB

<400> SEQUENCE: 55
ctcagtgacc cggtgcagct agaagtccat gtcggctggc tactactgca ggtctccagc    60

<210> SEQ ID NO 56
<211> LENGTH: 60
<212> TYPE: DNA
<213> ORGANISM: Artificial Sequence
<220> FEATURE:
<223> OTHER INFORMATION: reverse primer specific for the C-terminus of
      the FcyRIA extracellular domain and which includes a six His tag
      and stop codon sequence

<400> SEQUENCE: 56
tacaacccca gagctgtttt aaggcgcgcc tctagattag tgatggtgat ggtgatgtcc    60

<210> SEQ ID NO 57
<211> LENGTH: 59
<212> TYPE: DNA
<213> ORGANISM: Artificial Sequence
<220> FEATURE:
<223> OTHER INFORMATION: forward primer specific for FcgRIA leader
      sequence

<400> SEQUENCE: 57
tccacaggtg tccagggaat tcatataggc cggccatgtg gttcttgaca actctgctc     59

<210> SEQ ID NO 58
<211> LENGTH: 60
<212> TYPE: DNA
<213> ORGANISM: Artificial Sequence
<220> FEATURE:
<223> OTHER INFORMATION: reverse primer specific for C-terminus of the
      FcyRIA extracellular domain and which includes a 6 His tag and
      stop codon sequence

<400> SEQUENCE: 58
tacaacccca gagctgtttt aaggcgcgcc tctagattag tgatggtgat ggtgatgtcc    60

<210> SEQ ID NO 59
<211> LENGTH: 906
<212> TYPE: DNA
<213> ORGANISM: Artificial Sequence
<220> FEATURE:
<223> OTHER INFORMATION: Coding sequence for FcyRIIIA/IA with otPA
      leader

<400> SEQUENCE: 59
atggatgcaa tgaagagagg gctctgctgt gtgctgctgc tgtgtggcgc cgtcttcgtt    60
tcgctcagcc aggaaatcca tgccgagttg agacgcttcc gtagagaaga tctcccaaag   120
gctgtggtgt tcctggagcc tcaatggtac agggtgctcg agaaggacag tgtgactctg   180
aagtgccagg agcctactcc cctgaggac aattccacac agtggtttca caatgagagc   240
ctcatctcaa gccaggcctc gagctacttc attgacgctg ccacagtcga cgacagtgga   300
gagtacaggt gccagacaaa cctctccacc ctcagtgacc cggtgcagct agaagtccat   360
atcggctggc tactactgca ggtctccagc agagtcttca cggaaggaga acctctggcc   420
```

```
ttgaggtgtc atgcgtggaa ggataagctg gtgtacaatg tgctttacta tcgaaatggc    480
aaagccttta agttttttcca ctggaattct aacctcacca ttctgaaaac caacataagt   540
cacaatggca cctaccattg ctcaggcatg ggaaagcatc gctacacatc agcaggaata    600
tctgtcactg tgaaagagct atttccagct ccagtgctga atgcatctgt gacatcccca    660
ctcctggagg ggaatctggt caccctgagc tgtgaaacaa agttgctctt gcagaggcct    720
ggtttgcagc tttacttctc cttctacatg ggcagcaaga ccctgcgagg caggaacaca   780
tcctctgaat accaaatact aactgctaga agagaagact ctgggttata ctggtgcgag    840
gctgccacag aggatggaaa tgtccttaag cgcagccctg agttggagct tcaagtgctt    900
ggctaa                                                               906
```

<210> SEQ ID NO 60
<211> LENGTH: 301
<212> TYPE: PRT
<213> ORGANISM: Artificial Sequence
<220> FEATURE:
<223> OTHER INFORMATION: FcyRIIIA/IA with otPA leader

<400> SEQUENCE: 60

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Glu Asp Leu Pro Lys Ala Val Val Phe Leu Glu Pro Gln
        35                  40                  45

Trp Tyr Arg Val Leu Glu Lys Asp Ser Val Thr Leu Lys Cys Gln Gly
    50                  55                  60

Ala Tyr Ser Pro Glu Asp Asn Ser Thr Gln Trp Phe His Asn Glu Ser
65                  70                  75                  80

Leu Ile Ser Ser Gln Ala Ser Ser Tyr Phe Ile Asp Ala Ala Thr Val
                85                  90                  95

Asp Asp Ser Gly Glu Tyr Arg Cys Gln Thr Asn Leu Ser Thr Leu Ser
            100                 105                 110

Asp Pro Val Gln Leu Glu Val His Ile Gly Trp Leu Leu Leu Gln Val
        115                 120                 125

Ser Ser Arg Val Phe Thr Glu Gly Glu Pro Leu Ala Leu Arg Cys His
    130                 135                 140

Ala Trp Lys Asp Lys Leu Val Tyr Asn Val Leu Tyr Tyr Arg Asn Gly
145                 150                 155                 160

Lys Ala Phe Lys Phe Phe His Trp Asn Ser Asn Leu Thr Ile Leu Lys
                165                 170                 175

Thr Asn Ile Ser His Asn Gly Thr Tyr His Cys Ser Gly Met Gly Lys
            180                 185                 190

His Arg Tyr Thr Ser Ala Gly Ile Ser Val Thr Val Lys Glu Leu Phe
        195                 200                 205

Pro Ala Pro Val Leu Asn Ala Ser Val Thr Ser Pro Leu Leu Glu Gly
    210                 215                 220

Asn Leu Val Thr Leu Ser Cys Glu Thr Lys Leu Leu Leu Gln Arg Pro
225                 230                 235                 240

Gly Leu Gln Leu Tyr Phe Ser Phe Tyr Met Gly Ser Lys Thr Leu Arg
                245                 250                 255

Gly Arg Asn Thr Ser Ser Glu Tyr Gln Ile Leu Thr Ala Arg Arg Glu
            260                 265                 270
```

```
Asp Ser Gly Leu Tyr Trp Cys Glu Ala Ala Thr Glu Asp Gly Asn Val
        275                 280                 285

Leu Lys Arg Ser Pro Glu Leu Glu Leu Gln Val Leu Gly
        290                 295                 300

<210> SEQ ID NO 61
<211> LENGTH: 48
<212> TYPE: DNA
<213> ORGANISM: Homo sapiens

<400> SEQUENCE: 61
atgccgctgc tgctcctgct gcccctgctg tgggcagggg ccctggct        48

<210> SEQ ID NO 62
<211> LENGTH: 16
<212> TYPE: PRT
<213> ORGANISM: Homo sapiens

<400> SEQUENCE: 62

Met Pro Leu Leu Leu Leu Leu Pro Leu Leu Trp Ala Gly Ala Leu Ala
1               5                   10                  15

<210> SEQ ID NO 63
<211> LENGTH: 57
<212> TYPE: DNA
<213> ORGANISM: Artificial Sequence
<220> FEATURE:
<223> OTHER INFORMATION: Coding sequence for modified VH5 alpha leader

<400> SEQUENCE: 63
atggggtcaa ccgccatcct tggcctcctc ctggctgttc tccaaggagt ctggccg        57

<210> SEQ ID NO 64
<211> LENGTH: 19
<212> TYPE: PRT
<213> ORGANISM: Artificial Sequence
<220> FEATURE:
<223> OTHER INFORMATION: Modified VH5 alpha leader

<400> SEQUENCE: 64

Met Gly Ser Thr Ala Ile Leu Gly Leu Leu Leu Ala Val Leu Gln Gly
1               5                   10                  15

Val Trp Pro

<210> SEQ ID NO 65
<211> LENGTH: 870
<212> TYPE: DNA
<213> ORGANISM: Artificial Sequence
<220> FEATURE:
<223> OTHER INFORMATION: Coding sequence for FcyRIIIA/IA with modified
      TPA leader

<400> SEQUENCE: 65
atggatgcaa tgaagagagg ctctgctgt gtgctgctgc tgtgtggcgc cgtcttcgtt        60
tcgctcagcg aagatctccc aaaggctgtg gtgttcctgg agcctcaatg gtacagggtg       120
ctcgagaagg acagtgtgac tctgaagtgc cagggagcct actcccctga ggacaattcc       180
acacagtggt tcacaatga gagcctcatc tcaagccagg cctcgagcta cttcattgac       240
```

```
gctgccacag tcgacgacag tggagagtac aggtgccaga caaacctctc caccctcagt    300
gacccggtgc agctagaagt ccatatcggc tggctactac tgcaggtctc cagcagagtc    360
ttcacggaag gagaacctct ggccttgagg tgtcatgcgt ggaaggataa gctggtgtac    420
aatgtgcttt actatcgaaa tggcaaagcc tttaagtttt tccactggaa ttctaacctc    480
accattctga aaccaacata agtcacaatg gcacctacca ttgctcagg catgggaaag    540 catcgctaca tcagcagg aatatctgtc actgtgaaag agctatttcc agctccagtg    600
ctgaatgcat ctgtgacatc cccactcctg gagggaatc tggtcaccct gagctgtgaa    660
acaaagttgc tcttgcagag gcctggtttg cagctttact tctccttcta catgggcagc    720
aagaccctgc gaggcaggaa cacatcctct gaataccaaa tactaactgc tagaagagaa    780
gactctgggt tatactggtg cgaggctgcc acagaggatg gaaatgtcct taagcgcagc    840
cctgagttgg agcttcaagt gcttggctaa                                     870
```

<210> SEQ ID NO 66
<211> LENGTH: 289
<212> TYPE: PRT
<213> ORGANISM: Artificial Sequence
<220> FEATURE:
<223> OTHER INFORMATION: FcyRIIIA/IA with modified TPA leader

<400> SEQUENCE: 66

```
Met Asp Ala Met Lys Arg Gly Leu Cys Cys Val Leu Leu Cys Gly
1               5                   10                  15

Ala Val Phe Val Ser Leu Ser Glu Asp Leu Pro Lys Ala Val Phe
                20                  25                  30

Leu Glu Pro Gln Trp Tyr Arg Val Leu Glu Lys Asp Ser Val Thr Leu
            35                  40                  45

Lys Cys Gln Gly Ala Tyr Ser Pro Glu Asp Asn Ser Thr Gln Trp Phe
    50                  55                  60

His Asn Glu Ser Leu Ile Ser Ser Gln Ala Ser Ser Tyr Phe Ile Asp
65                  70                  75                  80

Ala Ala Thr Val Asp Asp Ser Gly Glu Tyr Arg Cys Gln Thr Asn Leu
                85                  90                  95

Ser Thr Leu Ser Asp Pro Val Gln Leu Glu Val His Ile Gly Trp Leu
            100                 105                 110

Leu Leu Gln Val Ser Ser Arg Val Phe Thr Glu Gly Glu Pro Leu Ala
        115                 120                 125

Leu Arg Cys His Ala Trp Lys Asp Lys Leu Val Tyr Asn Val Leu Tyr
    130                 135                 140

Tyr Arg Asn Gly Lys Ala Phe Lys Phe Phe His Trp Asn Ser Asn Leu
145                 150                 155                 160

Thr Ile Leu Lys Thr Asn Ile Ser His Asn Gly Thr Tyr His Cys Ser
                165                 170                 175

Gly Met Gly Lys His Arg Tyr Thr Ser Ala Gly Ile Ser Val Thr Val
            180                 185                 190

Lys Glu Leu Phe Pro Ala Pro Val Leu Asn Ala Ser Val Thr Ser Pro
        195                 200                 205

Leu Leu Glu Gly Asn Leu Val Thr Leu Ser Cys Glu Thr Lys Leu Leu
    210                 215                 220

Leu Gln Arg Pro Gly Leu Gln Leu Tyr Phe Ser Phe Tyr Met Gly Ser
225                 230                 235                 240

Lys Thr Leu Arg Gly Arg Asn Thr Ser Ser Glu Tyr Gln Ile Leu Thr
                245                 250                 255
```

```
Ala Arg Arg Glu Asp Ser Gly Leu Tyr Trp Cys Glu Ala Ala Thr Glu
            260                 265                 270

Asp Gly Asn Val Leu Lys Arg Ser Pro Glu Leu Glu Leu Gln Val Leu
        275                 280                 285

Gly
```